(12) United States Patent
Brain

(10) Patent No.: US 7,159,589 B2
(45) Date of Patent: *Jan. 9, 2007

(54) DISPOSABLE LARYNGEAL MASK AIRWAY DEVICE

(75) Inventor: Archibald I. J. Brain, Les Bons Villers (BE)

(73) Assignee: Indian Ocean Medical Inc., Mahe (SC)

( * ) Notice: Subject to any disclaimer, the term of this patent is extended or adjusted under 35 U.S.C. 154(b) by 103 days.

This patent is subject to a terminal disclaimer.

(21) Appl. No.: 10/138,806

(22) Filed: May 3, 2002

(65) Prior Publication Data

US 2003/0037790 A1    Feb. 27, 2003

Related U.S. Application Data

(60) Provisional application No. 60/314,438, filed on Aug. 23, 2001.

(51) Int. Cl.
*A61M 16/00* (2006.01)

(52) U.S. Cl. .............................. 128/207.14; 128/207.15

(58) Field of Classification Search ........... 128/207.14, 128/207.15, 200.26, 912, 206.29, DIG. 26
See application file for complete search history.

(56) References Cited

U.S. PATENT DOCUMENTS

| | | | |
|---|---|---|---|
| 2,862,498 A | 12/1958 | Weekes ....................... | 128/351 |
| 3,554,673 A | 1/1971 | Schwartz et al. ........... | 417/412 |
| 3,683,908 A | 8/1972 | Michael et al. | |
| 3,931,822 A | 1/1976 | Marici | |
| 4,104,357 A | 8/1978 | Blair | |
| 4,231,365 A | 11/1980 | Scarberry .............. | 128/207.15 |
| 4,256,099 A | 3/1981 | Dryden | |
| 4,509,514 A | 4/1985 | Brain ...................... | 128/207.15 |
| 4,553,540 A | 11/1985 | Straith .................... | 128/200.26 |
| 4,793,327 A | 12/1988 | Frankel | |
| 4,832,020 A | 5/1989 | Augustine | |
| 4,872,483 A | 10/1989 | Shah .......................... | 137/557 |
| 4,953,547 A | 9/1990 | Poole, Jr. ............... | 128/203.12 |
| 4,995,388 A | 2/1991 | Brain ..................... | 128/207.15 |
| 5,038,766 A | 8/1991 | Parker ................... | 128/200.26 |
| 5,042,469 A | 8/1991 | Augustine | |
| 5,203,320 A | 4/1993 | Augustine | |
| 5,235,973 A | 8/1993 | Levinson | |

(Continued)

FOREIGN PATENT DOCUMENTS

CA    2067782    6/1999

(Continued)

OTHER PUBLICATIONS

Brain, "The laryngeal mask airway—a possible new solution to airway problems in the emergency situation," *Archives of Emergency Medicine*, 1984, 1, 229-232.

(Continued)

*Primary Examiner*—Anhtuan T. Nguyen
*Assistant Examiner*—Darwin P Erezo
(74) *Attorney, Agent, or Firm*—Wilmer Cutler Pickering Hale and Dorr LLP

(57) ABSTRACT

The disclosed laryngeal mask airway device includes a mask portion and an airway tube. The mask portion includes an inflatable cuff, which defines a central opening when the cuff is inflated. The airway tube defines an internal passage extending from a proximal end of the tube to a distal end of the tube. The airway tube further defines two or more tabs disposed near the distal end of the tube. The mask portion is coupled to the airway tube near the distal end of the airway tube, and the tabs extend from the airway tube into the central opening defined by the cuff when the cuff is inflated.

7 Claims, 45 Drawing Sheets

U.S. PATENT DOCUMENTS

| | | | |
|---|---|---|---|
| 5,241,956 A | 9/1993 | Brain | 128/207.15 |
| 5,249,571 A | 10/1993 | Brain | 128/207.14 |
| 5,277,178 A | 1/1994 | Dingley et al. | |
| 5,282,464 A | 2/1994 | Brain | 128/207.15 |
| 5,297,547 A | 3/1994 | Brain | 128/207.15 |
| 5,303,697 A | 4/1994 | Brain | 128/200.26 |
| 5,305,743 A | 4/1994 | Brain | |
| 5,339,805 A | 8/1994 | Parker | 128/200.26 |
| 5,339,808 A | 8/1994 | Don Michael | 128/207.015 |
| 5,355,879 A | 10/1994 | Brain | 128/207.15 |
| 5,391,248 A | 2/1995 | Brain | 156/242 |
| 5,487,383 A | 1/1996 | Levinson | |
| 5,529,582 A | 6/1996 | Fukuhara | 606/205 |
| 5,569,219 A | 10/1996 | Hakki et al. | 604/282 |
| 5,582,167 A | 12/1996 | Joseph | |
| 5,584,290 A | 12/1996 | Brain | 128/207.15 |
| 5,599,301 A | 2/1997 | Jacobs et al. | 604/65 |
| 5,623,921 A | 4/1997 | Kinsinger et al. | 128/200.26 |
| 5,632,271 A | 5/1997 | Brain | 128/207.15 |
| RE35,531 E | 6/1997 | Callaghan et al. | 128/207.15 |
| 5,653,229 A | 8/1997 | Greenberg | 128/207.15 |
| 5,655,528 A | 8/1997 | Pagan | 128/207.14 |
| 5,682,880 A | 11/1997 | Brain | 128/207.15 |
| 5,694,929 A | 12/1997 | Christopher | |
| 5,711,293 A | 1/1998 | Brain | 128/200.24 |
| 5,738,094 A | 4/1998 | Hoftman | |
| 5,743,254 A | 4/1998 | Parker | 128/200.26 |
| 5,743,258 A | 4/1998 | Sato et al. | |
| 5,746,202 A | 5/1998 | Pagan | 128/207.14 |
| 5,771,889 A | 6/1998 | Pagan | 128/207.15 |
| 5,791,341 A | 8/1998 | Bullard | 128/207.15 |
| 5,850,832 A | 12/1998 | Chu | 128/200.26 |
| 5,865,176 A | 2/1999 | O'Neil | 128/207.15 |
| 5,878,745 A | 3/1999 | Brain | 128/207.15 |
| 5,881,726 A | 3/1999 | Neame | 128/207.15 |
| 5,896,858 A | 4/1999 | Brain | 128/207.15 |
| 5,915,383 A | 6/1999 | Pagan | 128/207.15 |
| 5,937,860 A | 8/1999 | Cook | 128/207.15 |
| 5,979,445 A | 11/1999 | Neame et al. | 128/207.15 |
| 5,983,897 A | 11/1999 | Pagen | |
| 5,988,167 A | 11/1999 | Kamen | 128/207.15 |
| 5,996,582 A | 12/1999 | Turnbull | |
| 6,003,510 A | 12/1999 | Anunta | 128/200.26 |
| 6,003,514 A | 12/1999 | Pagan | 128/207.15 |
| 6,012,452 A | 1/2000 | Pagan | 128/200.26 |
| 6,021,779 A | 2/2000 | Pagan | 128/207.15 |
| 6,050,264 A | 4/2000 | Greenfield | 128/207.15 |
| 6,070,581 A | 6/2000 | Augustine et al. | 128/207.15 |
| 6,079,409 A | 6/2000 | Brain | 128/200.26 |
| D429,811 S | 8/2000 | Bermudez | D24/110.5 |
| 6,095,144 A | 8/2000 | Pagan | 128/207.15 |
| 6,116,243 A | 9/2000 | Pagan | 128/207.15 |
| 6,119,695 A | 9/2000 | Augustine et al. | 128/207.15 |
| 6,240,922 B1 * | 6/2001 | Pagan | 128/207.15 |
| 6,390,093 B1 | 5/2002 | Mongeon | 128/207.15 |
| 6,427,686 B1 * | 8/2002 | Augustine et al. | 128/200.26 |
| 6,439,232 B1 | 8/2002 | Brain | |
| 6,631,720 B1 | 10/2003 | Brain et al. | |
| 6,705,318 B1 * | 3/2004 | Brain | 128/207.14 |
| 7,004,169 B1 | 2/2006 | Brain et al. | |
| 2003/0051734 A1 | 3/2003 | Brain | |
| 2003/0131845 A1 | 7/2003 | Lin | |

FOREIGN PATENT DOCUMENTS

| | | |
|---|---|---|
| CA | 2012750 | 8/1999 |
| DE | 100 42 172 | 4/2001 |
| EP | 0 294 200 | 12/1988 |
| EP | 0 389 272 | 9/1990 |
| EP | 0 402 872 | 12/1990 |
| EP | 0 294 200 | 4/1992 |
| EP | 0 580 385 | 5/1996 |
| EP | 0 712 638 | 5/1996 |
| EP | 0 732 116 | 9/1996 |
| EP | 0 796 631 | 9/1997 |
| EP | 0 845 276 | 6/1998 |
| EP | 0 865 798 | 9/1998 |
| EP | 0 922 465 | 6/1999 |
| EP | 1 125 595 | 8/2001 |
| EP | 1119386 B1 | 9/2005 |
| GB | 2111394 | 12/1982 |
| GB | 2205499 | 6/1987 |
| GB | 2298797 A | 9/1996 |
| GB | 2317342 | 8/1997 |
| GB | 2317830 | 9/1997 |
| GB | 2318735 | 10/1997 |
| GB | 2319478 | 10/1997 |
| GB | 2321854 | 1/1998 |
| GB | 2323289 | 2/1998 |
| GB | 2323290 | 3/1998 |
| GB | 2323291 | 3/1998 |
| GB | 2323292 | 3/1998 |
| GB | 2359996 | 9/2001 |
| JP | 10118182 | 5/1998 |
| JP | 10216233 | 8/1998 |
| JP | 10263086 | 10/1998 |
| JP | 10277156 | 10/1998 |
| JP | 10314308 | 12/1998 |
| JP | 10323391 | 12/1998 |
| JP | 10328303 | 12/1998 |
| JP | 11128349 | 5/1999 |
| JP | 11192304 | 7/1999 |
| JP | 11206885 | 8/1999 |
| WO | WO 91/03207 | 3/1991 |
| WO | WO 91/07201 | 5/1991 |
| WO | WO 91/12845 | 9/1991 |
| WO | WO 92/13587 | 8/1992 |
| WO | WO 95/33506 | 12/1995 |
| WO | WO 97/12640 | 4/1997 |
| WO | WO 97/12641 | 4/1997 |
| WO | WO 98/16273 | 4/1998 |
| WO | WO 99/06093 | 2/1999 |
| WO | WO 00/09189 * | 2/2000 |
| WO | WO 00/22985 | 4/2000 |
| WO | WO 00/23135 | 4/2000 |
| WO | WO 00/61212 | 10/2000 |
| WO | WO 00/61213 | 10/2000 |

OTHER PUBLICATIONS

Brain, "The laryngeal mask airway," *Anaesthesia*, 1985, vol. 40, pp. 356-361.

Brain, "Three cases of difficult intubation overcome by the laryngeal mask airway," *Anaesthesia*, 1985, vol. 40, pp. 353-355.

Hickey, et al., "Cardiovascular response to insertion of Brain's laryngeal mark," *Anesth. Corresp.* 1990, vol. 45 pp. 629-633.

Davies, et al., "Laryngeal mask airway and tracheal tube insertion by unskilled personnel," *The Lancet*, vol. 336, pp. 977-979.

Brain, "The Laryngeal Mask—A New Concept in Airway Management," *Br. J. Anesth.* (1983), vol. 55, pp. 801-805.

Broderick, "The laryngeal mask airway," (1989) *Anaesthesia*, vol. 44, pp. 238-241.

Inomata, et al., "Transient Bilateral Vocal Cord Paralysis after Insertion of a Laryngeal Mask Airway," *Anesthesiology*, 82:787-788, 1995.

Majumder, et al., "Bilateral Lingual Nerve Injury Following the Use of the Laryngeal Mask Airway," *Anaesthesia*, 1998, vol. 53, pp. 184-186.

Wynn, et al., "Tongue Cyanosis after Laryngeal Mask Airway Insertion," *Anesthesiology*, V. 80, No. 6, Jun. 1994, p. 1403.

Nagai, "Unilateral hypoglossal nerve paralysis following the use of the laryngeal amsk airway," *Anaesthesia*, 1994, vol. 49, pp. 603-604.

Brain, et al., "A new laryngeal mask prototype," *Anaesthesia*, 1995, vol. 50, pp. 42-48.

Burgard, et a., The Effect of Laryngeal Mask Cuff Pressure on Postoperative Sore Throat Incidence, *J. of Clinical Anesthesia* 8:198-201, 1996.

Benumof, "Laryngeal Mask Airway and the ASA Difficult Airway Algorithm," *Anesthesiology* 1996:v84 No. 3:686-99.

Pennant, "Comparison of the Endotracheal Tube and Laryngeal Mask in Airway Management by Paramedical Personnel," *Anesth Analg* 1992:74:531-4.

Brimacombe, "The split laryngeal mask airway," p. 639.

Worthington, et al., "Proceedings of the Anaesthetic Research Society," *Br. J. Anaesthesia* 1995 75:228P-229P.

Health, "Endotracheal intubation through the Laryngeal Mask—helpful when laryngoscopy is difficult or dangerous," *European Journal of Anaesthesiology* 1991, Suppl. 4, 41-45.

Kambic, et al., "Intubation Lesions of the Larynx," *Br. J. Anasth.* 1978, 50, 587-590.

Abdelatti, "A cuff pressure controller for tracheal tubes and laryngeal mask airway," *Anaesthesia*, 1999, 54 pp. 981-986.

Muthuswamy, et al., "The Use of Fuzzy Integrals and Bispectral Analysis of the Electroencephalogram to Predict Movement Under Anesthesia," *IEEE Transactions on Biomedical Engineering*, vol. 46, No. 3, Mar. 1999, pp. 290-299.

Glen, "The development of 'Diprifusor': a TCI system for propofol," *Anaesthesia* 1998, 53, Suppl. 1, pp. 13-21.

Gray et al., "Development of the technology for 'Diprifusor' TCI systems," *Anaesthesia* 1998, 53, Suppl. 1, pp. 22-27.

Engbers, "Practical use of 'Diprofusor' systems", *Anaesthesia* 1998, 53, Suppl. 1, pp. 28-34.

Doyle et al., "Intraoperative Awareness: A Continuing Clinical Problem," http://doyle.ibme.utoronto.ca/anesthesia/aware.htm.

Eriksson, et al., "Functional Assessment of the Pharynx at Rest and during Swallowing in Partially Paralyzed Humans," *Anesthesiology* vol. 87, No. 5, Nov. 1997, pp. 1035-1042.

Cuff-Pressure-Control CDR 2000, LogoMed.

Seegobin, et al., "Endotracheal cuff pressure and tracheal mucosal blood flow: endoscopic study of effects of four large volume cuffs," *British Medical Journal*, vol. 288, Mar. 31, 1984.

Raeder, et al., "Tracheal tube cuff pressures," *Anaesthesia*, 1985, vol. 40, pp. 444-447.

Jacobson et al., A Study of Intracuff Pressure Measurements, Trends and Behaviours in Patients During Prolonged Periods of Tracheal Intubation, *Br. J. Anaesth.* 1981, 53, 97.

Willis, et al., "Tracheal tube cuff pressure," *Anaesthesia*, 1988, vol. 43, pp. 312-314.

Miller, "A pressure regulatory for the cuff of a tracheal tube," *Anaesthesia*, 1992, vol. 47, pp. 594-596.

Patel, et al, "Tracheal tube cuff pressure," *Anaesthesia*, 1984, vol. 39, pp. 862-864.

Pippin, et al., "Long-term tracheal intubation practice in the United Kingdom", *Anaesthesia*, 1983, vol. 38, pp. 791-795.

Bernhard, et al., "Adjustment of Intracuff Pressure to Prevent Aspiration," *Anesthesiology* v. 50 No. 4:363-366, 1979.

Bernhard, et al., "Physical Characteristics of and Rates of Nitrous Oxide Diffusion into Tracheal Tube Cuffs," *Anesthesiology* 48:413-417 1978.

Craven, "Prevention of Hospital-Acquired Pneumonia: Measuring Effect in Ounces, Pounds, and Tons, " *Annals of Internal Medicine*, vol. 122, No. 3, pp. 229-231 Feb. 1, 1995.

Lindholm,"Prolonged Endotracheal Intubation," *ACTA Anaesthesiologica Scandanavica* 1969 vol. 33 32-46.

Caplan R.A., Posner K.L., Wend R.J., Cheney F.W., "Adverse respiratory events in anesthesia: a closed claims analysis", *Anesthesiol.* 1990. 72:828-833.

Benumof J.L., "Management of the difficult airway with special emphasis on awake tracheal intubation," *Anesthsiol.* 1991. 75;6:1087.

Kapila A., Addy E.V., Verghese C., Brain A.J., "Intubating LMA: a preliminary assessment of performance". *British Journal of Anaesthesia*, 1995; 75:228-229 (Abstract).

Communication of a notice of opposition, European Patent Office, Feb. 15, 2006 (cover page and pp. 1-4).

DeMello et al., "The Use of the Laryngeal Mask Airway in Primary Anaesth. Corresp.," 1990, vol. 45, pp. 793-794.

Observations by Third Party Concerning European Patent Application No. 99 947 765.6-2318, European Patent Office, Munich, Germany, Jan. 18, 2005 (3 Pages).

Response to Complaint Matter No. 4b 440-05, In Matter of: LMA Deutschland GmbH versus Ambu (Deutschland) GmbH, Feb. 10, 2006, pp. 1-47.

\* cited by examiner

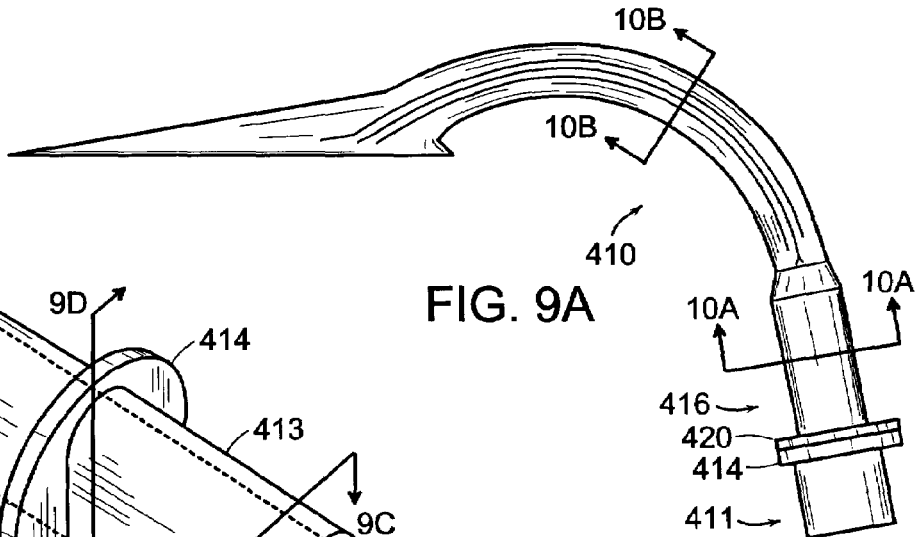
FIG. 9A
FIG. 9B
FIG. 9C
FIG. 9D
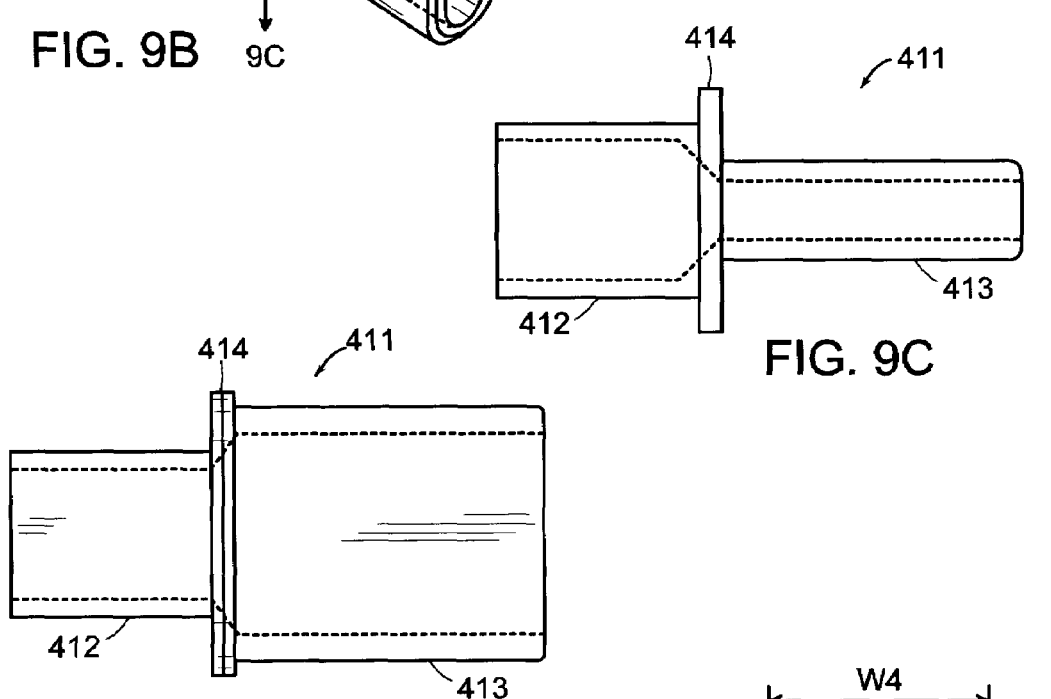
FIG. 10A
FIG. 10B

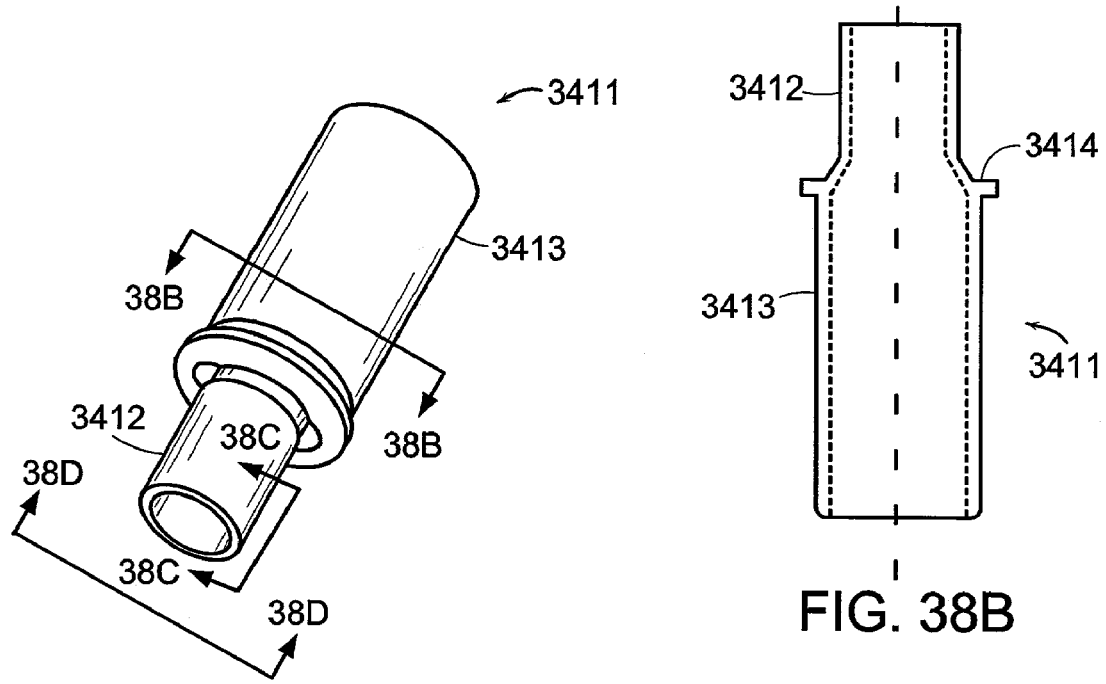
FIG. 38A
FIG. 38B
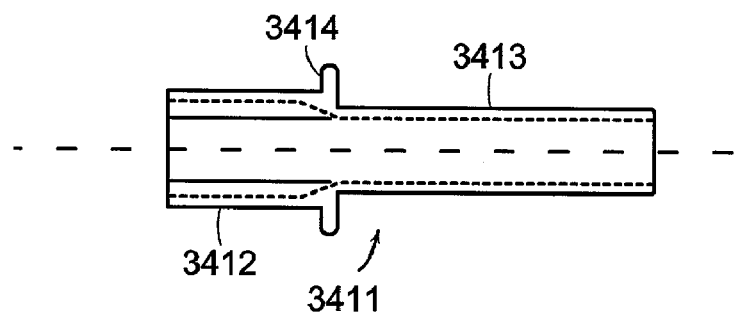
FIG. 38C
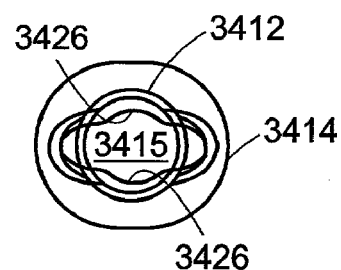
FIG. 38D

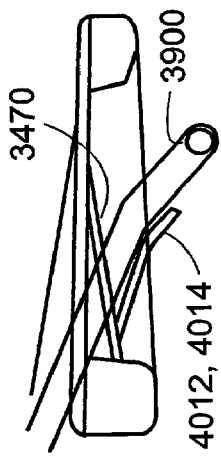
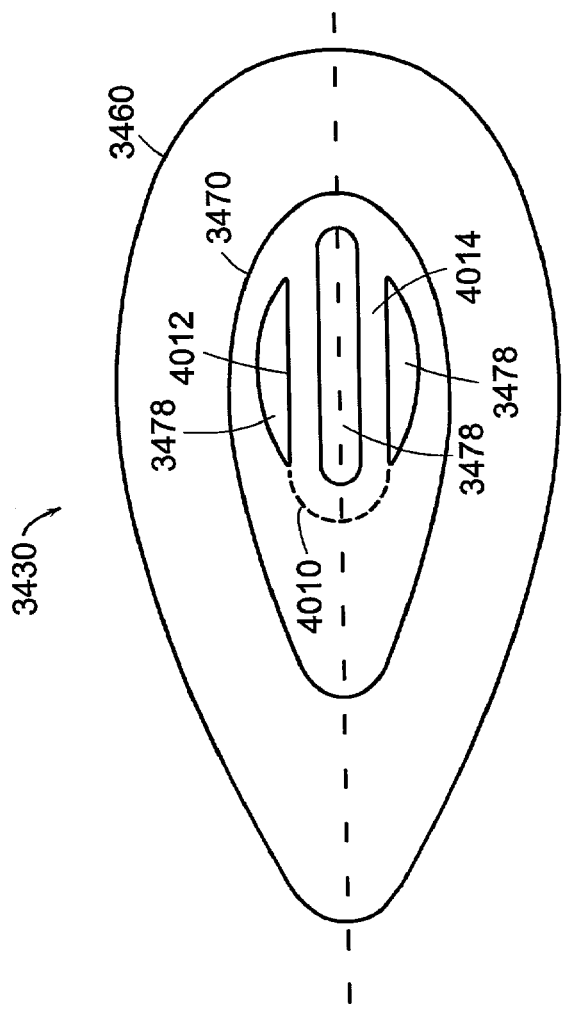
FIG. 40B
FIG. 40A

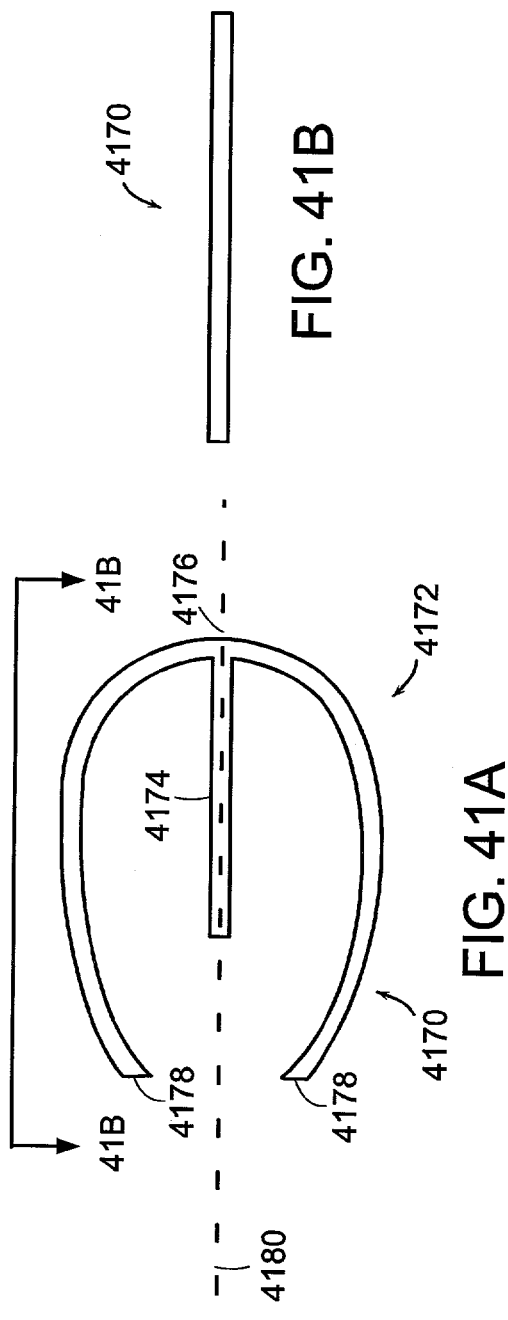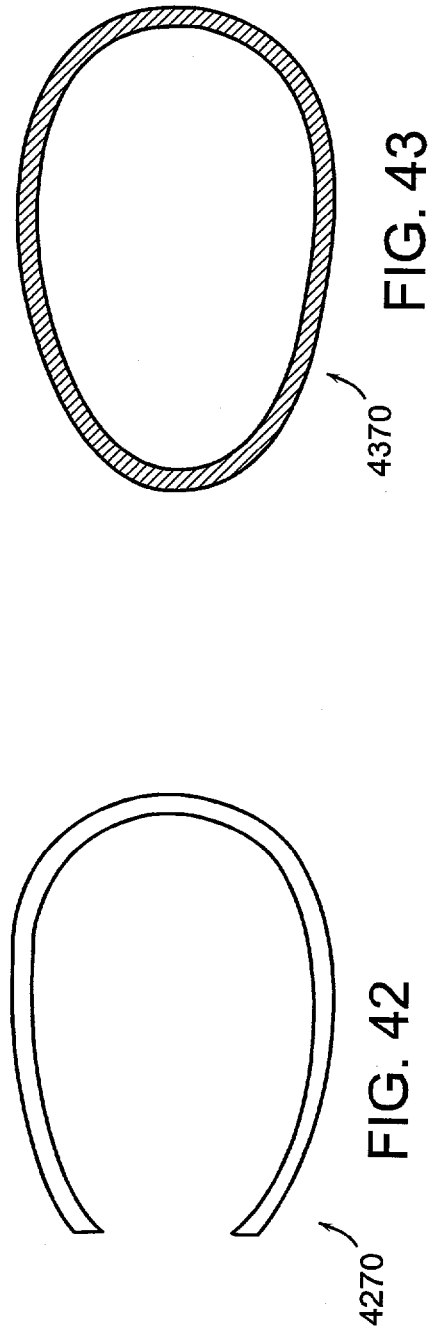

DISPOSABLE LARYNGEAL MASK AIRWAY DEVICE

REFERENCE TO RELATED APPLICATIONS

This application claims priority of U.S. Provisional Patent Application No. 60/314,438, entitled "Disposable LMA," which was filed Aug. 23, 2001, and which is expressly incorporated herein by reference in its entirety. This application is related to copending U.S. patent application Ser. No. 09/544,681, entitled "Disposable LMA," which was filed on Apr. 7, 2000.

BACKGROUND OF THE INVENTION

The present invention relates to a laryngeal mask airway device. More specifically, the present invention relates to reduced cost laryngeal masks, improved geometric configurations for laryngeal masks, and to methods of inexpensively fabricating such masks.

The laryngeal mask airway device is a well known device that is useful for establishing airways in unconscious patients. Such devices have been in use for about twelve years and offer an alternative to the older, even better known, endotracheal tube. For at least seventy years, endotracheal tubes comprising a long slender tube with an inflatable balloon disposed at the tube's distal end have been used for establishing airways in unconscious patients. In operation, the endotracheal tube's distal end is inserted through the mouth of the patient, past the patient's laryngeal inlet (or glottic opening), and into the patient's trachea. Once so positioned, the balloon is inflated so as to form a seal with the interior lining of the trachea. After this seal is established, positive pressure may be applied to the tube's proximal end to ventilate the patient's lungs. Also, the seal between the balloon and the inner lining of the trachea protects the lungs from aspiration (e.g., the seal prevents material regurgitated from the stomach from being aspirated into the patient's lungs).

Although they have been enormously successful, endotracheal tubes suffer from several major disadvantages. The principal disadvantage of the endotracheal tube relates to the difficulty of properly inserting the tube. Inserting an endotracheal tube into a patient is a procedure that requires a high degree of skill. Also, even for skilled practitioners, insertion of an endotracheal tube is sometimes difficult or not possible. In many instances, the difficulty of inserting endotracheal tubes has tragically led to the death of a patient because it was not possible to establish an airway in the patient with sufficient rapidity.

In addition to this principal disadvantage, there are also other disadvantages associated with endotracheal tubes. For example, intubation with an endotracheal tube often causes patients to suffer from severe "sore throats." The "sore throat" is principally caused by friction between the tube and the notch between the patient's arytenoid cartilages. Another disadvantage is that patients can not cough effectively while intubated with an endotracheal tube. Yet another problem with endotracheal tubes relates to the manner in which they are inserted. Inserting an endotracheal tube normally requires manipulations of the patient's head and neck and further requires the patient's jaw to be forcibly opened widely. These necessary manipulations make it difficult, or undesirable, to insert an endotracheal tube into a patient who may be suffering from a neck injury. Still another disadvantage is that endotracheal tubes provide an airway that is relatively small or narrow. The size of the airway must be relatively narrow because the distal end of the tube must be sufficiently small to fit into the trachea.

In contrast to the endotracheal tube, it is relatively easy to insert a laryngeal mask airway device into a patient and thereby establish an airway. Also, the laryngeal mask airway device is a "forgiving" device in that even if it is inserted improperly, it still tends to establish an airway. Accordingly, the laryngeal mask airway device is often thought of as a "life saving" device. Also, the laryngeal mask airway device may be inserted with only relatively minor manipulations of the patient's head, neck, and jaw. Further, the laryngeal mask airway device provides for ventilation of the patient's lungs without requiring contact with the sensitive inner lining of the trachea and the size of the airway established is typically significantly larger than the size of the airway established with an endotracheal tube. Also, the laryngeal mask airway device does not interfere with coughing to the same extent as endotracheal tubes. Largely due to these advantages, the laryngeal mask airway device has enjoyed increasing popularity over the last twelve years.

FIG. 1 shows a perspective view of a prior art laryngeal mask airway device 100 and FIG. 2 illustrates a device 100 that has been inserted into a patient. Laryngeal mask airway devices such as device 100 are described for example in U.S. Pat. No. 4,509,514. Device 100 includes a flexible cylindrical tube 110 and a mask portion 130. Tube 110 extends from a proximal end 112 to a distal end 114 and mask portion 130 is coupled to the tube's distal end 114. Mask portion 130 includes a proximal end 132 and a generally elliptical inflatable cuff 134. Mask portion 130 also defines a central passageway extending from proximal end 132 to an open end 136 of cuff 134. The distal end 114 of tube 110 is telescopically fit into the proximal end 132 of mask portion 130, and device 100 provides a continuous, sealed, airway extending from proximal end 112 of tube 110 to the open end 136 of cuff 134. Device 100 also includes an inflation tube 138 for selectively inflating or deflating cuff 134.

In operation, the cuff 134 is deflated, and then the mask portion is inserted through the patient's mouth into the patient's pharynx. The mask portion is preferably positioned so that a distal end 140 of cuff 134 rests against the patient's normally closed esophagus and so that the open end 136 of the cuff 134 is aligned with the entryway of the patient's trachea (i.e., the patient's glottic opening). After the mask portion is so positioned, the cuff is inflated thereby forming a seal around the patient's glottic opening and this establishes a sealed airway extending from the proximal end 112 of the tube 110 to the patient's trachea.

For convenience of exposition, the term "fully inserted configuration" shall be used herein to refer to a laryngeal mask airway device that has been inserted into a patient and has the following characteristics: (1) the mask portion is disposed around the patient's glottic opening; (2) the cuff is inflated forming a seal around the patient's glottic opening; and (3) the airway tube extends from a proximal end located outside the patient's mouth to a distal end that is coupled to the mask portion, the tube extending through the patient's mouth and the patient's natural upper airway so that the device provides a sealed airway extending from the tube's proximal end to the patient's lungs. FIG. 2 shows a laryngeal mask airway device in the fully inserted configuration.

When device 100 is in the fully inserted configuration, device 100 advantageously does not contact the interior lining of the trachea. Rather, the seal is established by contact between the tissues surrounding the patient's laryngeal inlet and the inflatable cuff 134. Unlike the delicate interior lining of the trachea, the tissues at the laryngeal inlet are accustomed to contact with foreign matter. For example, during the act of swallowing food, the food is normally squeezed against these tissues on its way to the esophagus. These tissues are accordingly less sensitive and less susceptible to being damaged by contact with the inflatable cuff.

FIG. 3 shows a sectional side view of the mask portion 230 of another prior art laryngeal mask airway device. The illustrated mask portion 230, which is described more fully in U.S. Pat. No. 5,355,879, includes an inflatable cuff 234 and a backplate 250. Backplate 250 defines a proximal end 232 for receiving, or coupling to, a cylindrical airway tube (not shown). Mask portion 230 defines a sealed passageway, or airway, that extends from proximal end 232 through to the open end 236 of cuff 234. This mask portion 230 also includes an inflatable back cushion that, when inflated, expands to the contour illustrated by phantom outline 252. As shown in FIG. 3, the cross sections of prior art cuffs are generally circular. The thickness T1 of the material used to form the cuff (i.e., the thickness of the cuff wall) is normally about 0.7–0.8 millimeters.

U.S. Pat. No. 5,303,697 describes an example of another type of prior art device that may be referred to as an "intubating laryngeal mask airway device." The intubating device is useful for facilitating insertion of an endotracheal tube. After an intubating laryngeal mask airway device has been located in the fully inserted configuration, the device can act as a guide for a subsequently inserted endotracheal tube. Use of the laryngeal mask airway device in this fashion facilitates what is commonly known as "blind insertion" of the endotracheal tube. Only minor movements of the patient's head, neck, and jaw are required to insert the intubating laryngeal mask airway device, and once the device has been located in the fully inserted configuration, the endotracheal tube may be inserted with virtually no additional movements of the patient. This stands in contrast to the relatively large motions of the patient's head, neck, and jaw that would be required if the endotracheal tube were inserted without the assistance of the intubating laryngeal mask airway device.

U.S. Pat. No. 5,632,271 describes an example of yet another type of prior art laryngeal mask airway device. In addition to providing an airway tube for ventilating a patient's lungs, this device also provides a second tube, a drainage tube, used for draining or removing regurgitated material. The distal end of the drainage tube is disposed proximal to the normally closed entrance to the patient's esophagus. In addition to providing drainage, the drainage tube may also be used to guide insertion of a gastric tube.

In general, prior art laryngeal mask airway devices have been manufactured by molding elastomeric materials such as silicone to desired shapes. One advantage of these materials is that they are durable enough to permit the devices to be sterilized in an autoclave and reused. For example, laryngeal mask airway devices sold by LMA International SA of Henley, England are guaranteed to survive forty sterilizations, and in practice these devices may generally be sterilized (and reused) more than forty times before becoming too worn for reuse. However, one disadvantage of these materials is that they are relatively expensive. Accordingly, it would be advantageous to develop a reduced cost laryngeal mask airway device.

Several attempts have been made in the prior art to provide reduced cost laryngeal mask airway devices. For example, U.S. Pat. No. 6,012,452 discloses a laryngeal mask airway device in which the mask portion is formed by adhering a foam material to both sides of a backplate. The foam forms an inflatable cuff that is attached to both sides of the plate. U.S. Pat. No. 5,983,897 discloses another laryngeal mask airway device in which the mask portion is formed by attaching cuff members to the top and bottom of a backplate. The cuff members may be formed from flexible, resilient plastics material, such as PVC. One disadvantage of the devices disclosed in the '897 and '452 patents is that the assembly of the disclosed mask portions necessarily involves two steps: a first step of fabricating the backplate and then a second step of adhering the cuff to the top and bottom of the plate. It would therefore be advantageous to develop a process for simultaneously forming all parts of the mask portion of a laryngeal mask airway device.

In addition to cost, another disadvantage of prior art laryngeal mask airway devices relates to the quality of the seal established between the patient and the device. The device 100 shown in FIG. 1 generally maintains a seal up to about twenty cm $H_2O$. That is, when the device is in the fully inserted configuration, the seal between the device and the patient will be maintained as long as the pressure applied to the proximal end of the airway tube is less than approximately twenty cm $H_2O$. However, if greater pressures are applied to the proximal end of the airway tube, the seal tends to be lost thereby causing loss of some fraction of the delivered gas volume, so that positive pressure ventilation may be less effective. This stands in contrast to the endotracheal tube, which can normally maintain a seal up to fifty cm $H_2O$. Accordingly, it would be advantageous to provide a laryngeal mask airway device that provides improved seals.

Still another disadvantage of prior art laryngeal mask airway devices relates to the profile, or geometric configuration, of the deflated device. When the cuff of a laryngeal mask airway device is deflated, the device would ideally, automatically, assume a shape that was optimized for facilitating insertion. However, prior art devices do not tend to automatically form such shapes when the cuff is deflated. Accordingly, several "forming tools" have been provided for affecting the shape of the deflated device. U.S. Pat. No. 5,711,293 discloses one such forming tool. However, it would be advantageous to provide a device that automatically assumes a profile that facilitated insertion when the cuff was deflated.

Yet another disadvantage of prior art laryngeal mask airway devices relates to the manner in which they are inserted into a patient. Anesthesiologists or other practitioners insert many types of prior art laryngeal mask airway devices by pushing one of their fingers against the proximal end of the cuff. Unfortunately, this procedure requires the practitioner to insert their finger into the patient's mouth and guide the device past the patient's throat. Since many practitioners prefer to avoid inserting their fingers into patient's mouths, several insertion tools have been developed for facilitating insertion of various laryngeal mask airway devices. However, it would be advantageous to provide a laryngeal mask airway device that could be inserted without an insertion tool and without requiring insertion of a finger into the patient's mouth.

SUMMARY OF THE INVENTION

These and other objects are provided by laryngeal mask airway devices that are characterized by improved geometric configurations and by methods of making such a devices. As will be discussed below, a reduced cost process for making a laryngeal mask airway device according to the invention includes a process known as rotational molding. The improved device includes two principal components: (1) a mask portion and (2) an airway tube. The device is fabricated by attaching the backplate portion of the airway tube to the mask portion. As will be discussed in greater detail below, the configuration of the two principal components (1) reduces the cost of fabricating the device and (2) improves the performance of the device.

In another aspect, the invention provides methods and structures for resisting compressive forces that can be generated within a patient so as to maintain an open airway passage in a laryngeal mask airway device.

Still other objects and advantages of the present invention will become readily apparent to those skilled in the art from the following detailed description wherein several embodiments are shown and described, simply by way of illustration of the best mode of the invention. As will be realized, the invention is capable of other and different embodiments, and its several details are capable of modifications in various respects, all without departing from the invention. Accordingly, the drawings and description are to be regarded as illustrative in nature, and not in a restrictive or limiting sense, with the scope of the application being indicated in the claims.

BRIEF DESCRIPTION OF THE FIGURES

For a fuller understanding of the nature and objects of the present invention, reference should be made to the following detailed description taken in connection with the accompanying drawings in which the same reference numerals are used to indicate the same or similar parts wherein:

FIG. 9A shows a side view of the airway tube of the device shown in FIGS. 4A, 4B, and 4C.

FIG. 9B shows a perspective view of the proximal section of the airway tube shown in FIG. 9A.

FIGS. 9C and 9D show views of the proximal section taken in the direction of lines 9C—9C and 9D—9D, respectively, as shown in FIG. 9B.

FIG. 10A shows a sectional view of the proximal section inserted into the integral tube and backplate section taken in the direction of the line 10A—10A as shown in FIG. 9A.

FIG. 10B shows a sectional view of the curved portion of the integral tube and backplate section taken in the direction of line 10B—10B as shown in FIG. 9A.

FIG. 35C shows a perspective view of the anterior surface of the mask portion shown in FIG. 35A.

FIG. 38A shows a perspective view of the connector section of the airway tube of the laryngeal mask airway device shown in FIGS. 34A–34C.

FIGS. 38B, 38C, and 38D show views of the connector section shown in FIG. 38A taken in the direction of lines 38B—38B, 38C—38C, and 38D—38D, respectively, as shown in FIG. 38A.

FIG. 40A shows an anterior view of another embodiment of a mask portion constructed according to the invention in which the support defines a fenestration for facilitating insertion of an endotracheal tube.

FIG. 40B shows a side view of an endotracheal tube being inserted through the mask portion shown in FIG. 40A.

FIG. 41A shows a top view of another support designed according to the invention.

FIG. 41B shows a side view of the support shown in FIG. 41A taken in the direction of the line 41B—41B as shown in FIG. 41A.

FIGS. 42 and 43 show top views of other supports constructed according to the invention.

DETAILED DESCRIPTION OF EXEMPLARY EMBODIMENTS

Figure 4A:
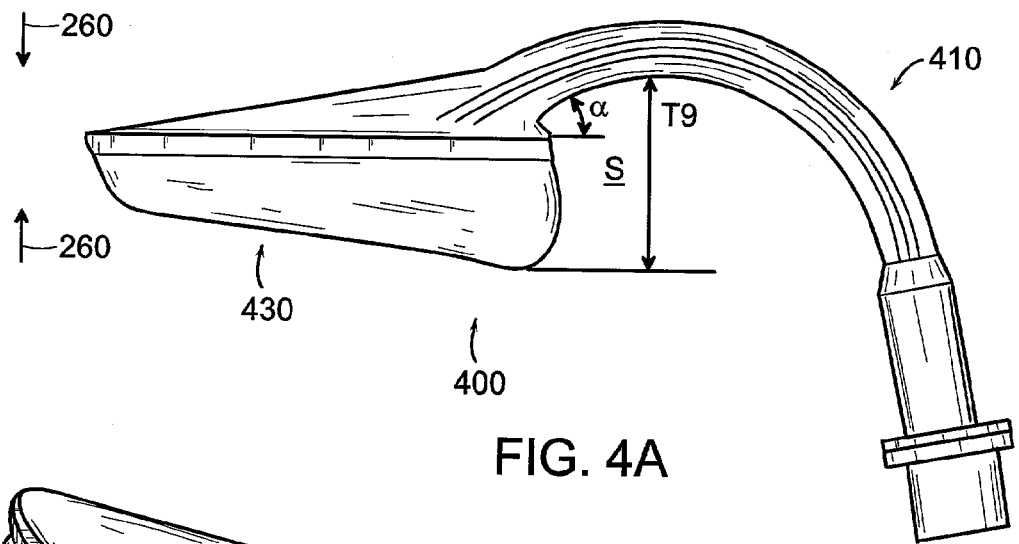
FIG. 4A shows a side view of a laryngeal mask airway device constructed according to the invention, the mask portion of the device being in an inflated condition.
Figure 4B:
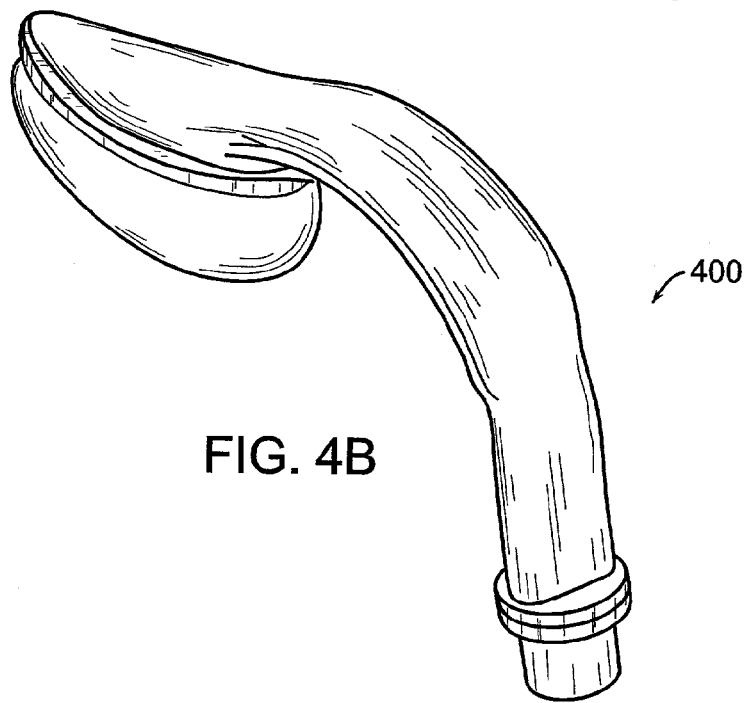
FIGS. 4B and 4C show two perspective views of the device shown in FIG. 4A.
Figure 4C:
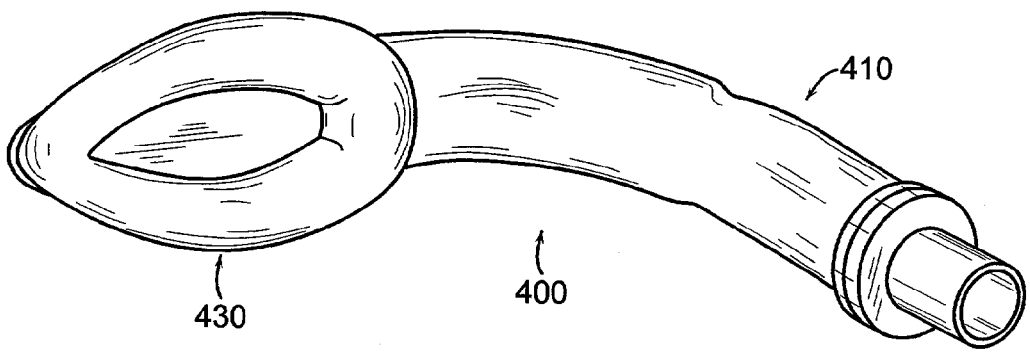

FIG. 4A shows a side view of one embodiment of a laryngeal mask airway device 400 constructed according to one aspect of the invention. FIGS. 4B and 4C show two perspective views of device 400. Device 400 is preferably constructed from two separate pieces that are bonded, or adhered, together. The first piece is an airway tube 410 and the second piece is a mask portion 430. In FIGS. 4A, 4B, and 4C, the mask portion 430 is shown in an inflated condition. As will be discussed in greater detail below, mask portion 430 may advantageously be formed by a process called rotational molding. The airway tube 410 may also be produced by rotational molding, or alternatively, could be produced using injection or other types of molding.

Figure 5A:
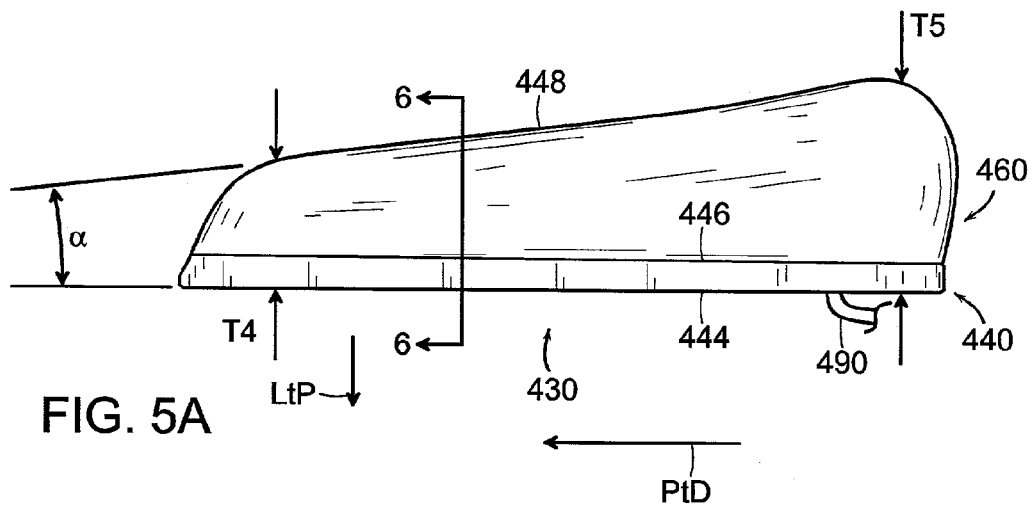
FIG. 5A shows a side view of the inflated mask portion of the device shown in FIGS. 4A, 4B, and 4C.
Figure 5B:
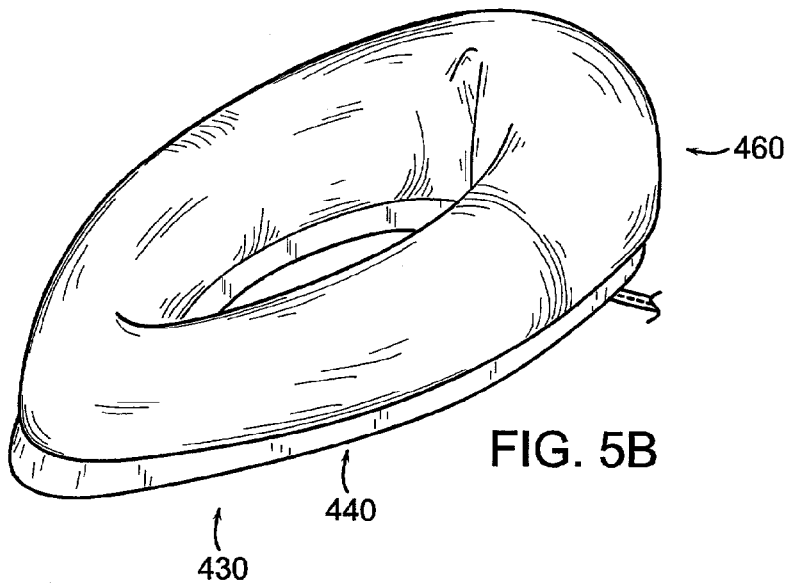
FIGS. 5B and 5C show two perspective views of the anterior portion of the mask portion shown in FIG. 5A.
Figure 5C:
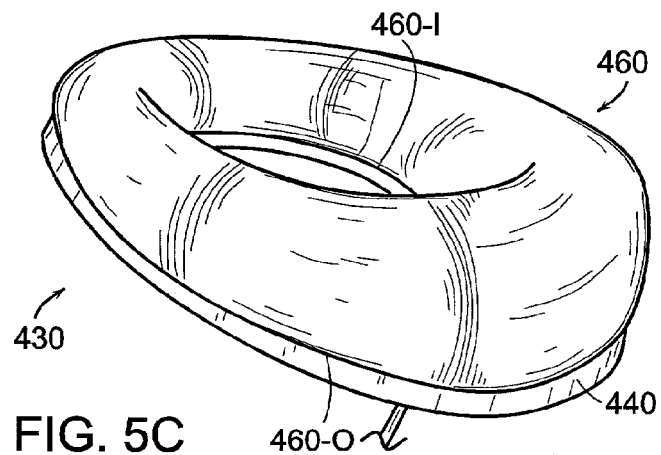
Figure 5D:
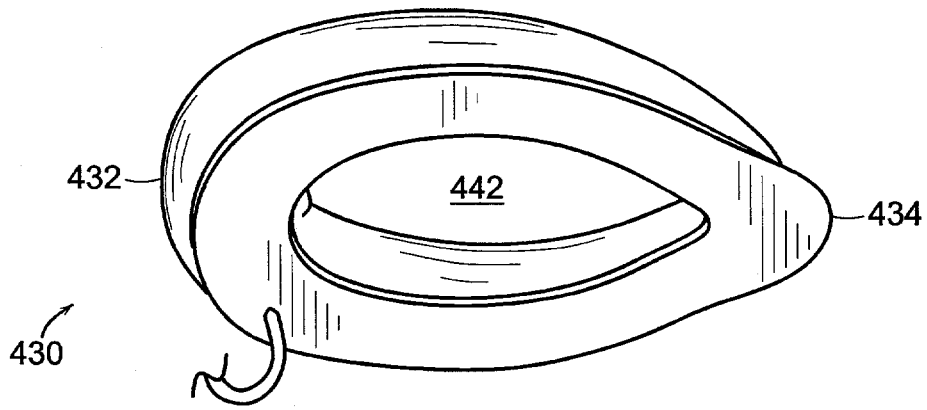
FIG. 5D shows a perspective view of the posterior portion of the mask portion shown in FIG. 5A.
Figure 5E:
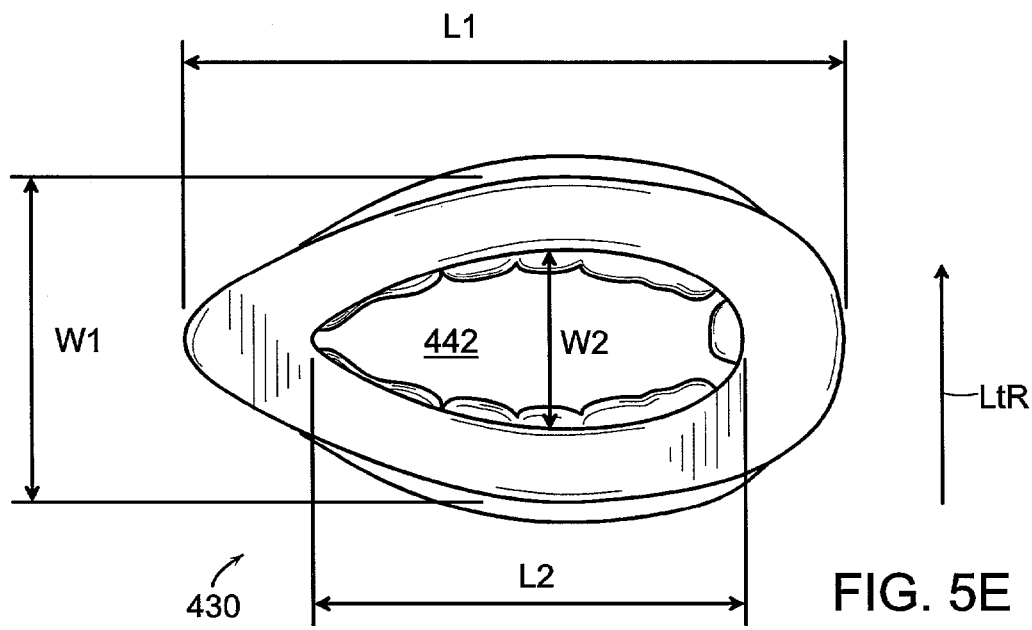
FIG. 5E shows a posterior view of the mask portion shown in FIG. 5A.
Figure 6:
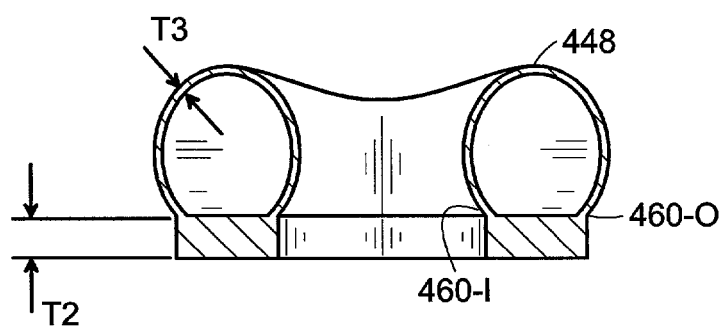
FIG. 6 shows a sectional view of the mask portion taken in the direction of line 6—6 as shown in FIG. 5A.
Figure 7A:
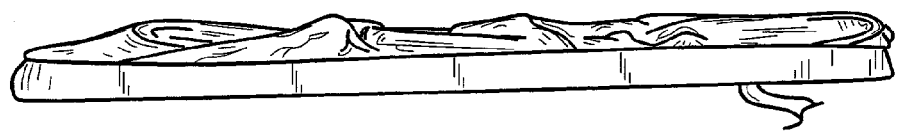
FIG. 7A shows a side view of the mask portion shown in FIG. 5A when the mask portion is deflated.
Figure 7B:
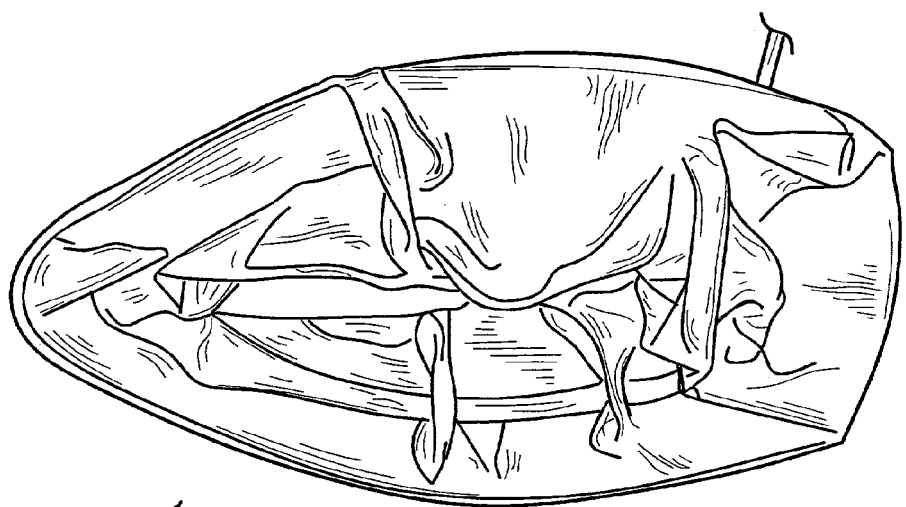
FIG. 7B shows an anterior view of the deflated mask portion shown in FIG. 7A.

FIG. 5A shows a side view of mask portion 430 when inflated. FIGS. 5B and 5C show two perspective views of the anterior side of mask portion 430 when inflated. FIG. 5D shows a perspective view of the posterior side of mask portion 430 when inflated, and FIG. 5E shows a view of the posterior side of mask portion 430 when inflated. The terms anterior and posterior as used above in connection with FIGS. 5B–5E are made with reference to the fully inserted configuration. That is, when the device 400 is in the fully inserted configuration, the portion of the mask portion 430 shown in FIGS. 5B and 5C will be located forward of, or anterior to, the portion shown in FIGS. 5D and 5E. Also, when device 400 is in the fully inserted configuration, the portion of mask portion 430 shown in FIGS. 5D and 5E will be disposed proximal to the patient's pharyngeal wall, posterior to the portions shown in FIGS. 5B and 5C. FIG. 6 shows a sectional view of mask portion 430 taken in the direction of line 6—6 as shown in FIG. 5A. FIGS. 7A and 7B show side and anterior views, respectively, of mask portion 430 when deflated.

Mask portion 430 includes a plate 440, an inflatable cuff 460, and an inflation tube 490. Mask portion 430 also defines a proximal end 432 and a distal end 434 (shown for example in FIG. 5D). Plate 440 is characterized by a generally elliptical shape and defines a central aperture or through hole 442 (shown best in FIG. 5E). For convenience of exposition, the shape of plate 440 may be referred to as that of an elliptical annulus. A classic annulus has circular symmetry, however, the elliptical annulus of plate 442 follows the elliptical profile illustrated in FIG. 5E. Plate 440 also defines a pharyngeal side 444 and a laryngeal side 446 (shown for example in FIG. 5A). The pharyngeal side 444 of plate 440 is so named because, as will be discussed below, the pharyngeal side 444 is disposed proximal to the pharyngeal wall of a patient when device 400 is in the fully inserted configuration. The central aperture 442 of plate 440 extends through the entire plate from the pharyngeal side 444 to the laryngeal side 446. The distance between the pharyngeal side 444 and the laryngeal side 446 of plate 440, or the thickness of the plate, shall be referred to as T2, as shown in FIG. 6. In some embodiments, the plate is substantially flat in that the thickness T2 is substantially uniform throughout the plate. One preferred value for the thickness T2 of the substantially flat plate 440 is about two millimeters plus or minus one millimeter. Even more preferably, the thickness T2 of the substantially flat plate 440 is two millimeters plus or minus 0.5 millimeters. Even more preferably, the thickness T2 of the substantially flat plate 440 is substantially equal to two millimeters. In other embodiments, it may be advantageous for the plate to have a tapering thickness so that the plate is thicker at the proximal end than at the distal end. For example, the thickness of the plate T2 may be about two millimeters at the proximal end and may smoothly taper to about one and a half millimeters at the distal end.

Inflatable cuff 460 is formed from a very thin, flexible, sheet of material that is attached to the laryngeal side 446 of plate 440. As shown best in FIG. 6, the cross-section of cuff 460, when inflated, is generally U-shaped (or has the shape of an inverted "U"). The generally elliptical inner periphery 460-I of cuff 460 is sealed, or attached, to plate 440 proximal to the generally elliptical periphery of aperture 442, and the generally elliptical outer periphery 460-O of cuff 460 is sealed, or attached, to plate 440 proximal to the generally elliptical outer periphery of the plate 440. The thickness of the cuff (i.e., the cuff wall), as shown in FIG. 6, shall be referred to as T3. One preferred value for the thickness T3 of the cuff is about 0.04 to 0.24 millimeters. More preferably, the thickness T3 is in the range 0.08 to 0.20 millimeters (or 0.14 plus or minus 0.06 millimeters). Even more preferably, the thickness T3 of the cuff is 0.14 plus or minus 0.03 millimeters.

For convenience of exposition, the shape of the inflated cuff 460 shall be referred to as "generally toroidal". The shape of the cuff is not strictly a torus for several reasons. For example, the cross section of the cuff is U-shaped rather than circular (as shown in FIG. 6). Also, a classic torus has a ring-like, or doughnut, shape (and is formed by rotating a circle about an axis in the plane of the circle that does not intersect the circle), whereas the cuff 460 follows the generally elliptical shape of the plate 440. Also, the thickness of the inflated cuff is not constant from the proximal end to the distal end (as shown for example in FIG. 5A by the angle alpha). However, despite these variations from the classic torus, the inflated cuff may be described as having a generally toroidal configuration (since it is essentially formed by sweeping the U-shaped cross section of the inflated cuff along the elliptical contour defined by the plate 440).

Plate 440 and cuff 460 of mask portion 430 cooperate to define a generally toroidal interior volume. Inflation tube 490 extends from the pharyngeal side 444 of plate 440 through the plate and into the interior volume to permit selective inflation and deflation of cuff 460.

Like plate 440, mask portion 430 defines a pharyngeal side and a laryngeal side. The pharyngeal side of mask portion 430 is coincident with the pharyngeal side 444 of plate 440. The laryngeal side 448 of mask portion 430 is defined by inflatable cuff 460. As shown best in FIGS. 5A and 6, when the cuff 460 is inflated, the laryngeal side 448 of mask portion 430 is defined by the exterior surface of cuff 460 at the portion of the cuff 460 that is disposed opposite to plate 440, or furthest from plate 440. When device 400 is in the fully inserted configuration, the laryngeal side 448 of mask portion 430 is in physical contact with the tissues surrounding the patient's laryngeal inlet. As shown best in FIGS. 5D and 5E, when cuff 460 is inflated, the aperture 442 extends entirely through the mask portion so that the mask portion 430 defines a passage 442 that extends from the laryngeal side to the pharyngeal side.

For convenience of exposition, three directions shall be defined with respect to mask portion 430. The arrow PtD shown in FIG. 5A extends in a proximal-to-distal direction. Mask portion 430 extends in the proximal-to-distal direction from the proximal end 432 to the distal end 434. It will be appreciated that a distal-to-proximal direction extends opposite to, or is rotated 180 degrees from, the proximal-to-distal direction. The arrow LtP shown in FIG. 5A extends in a laryngeal-to-pharyngeal direction. Mask portion 430 extends in the laryngeal-to-pharyngeal direction from laryngeal side 448 to pharyngeal side 444. It will be appreciated that a pharyngeal-to-laryngeal direction extends opposite to, or is rotated 180 degrees from, the laryngeal-to-pharyngeal direction. (The laryngeal-to-pharyngeal direction could also be referred to as the "antero-posterior" direction.) The arrow LtR shown in FIG. 5E extends in the left-to-right direction. It will be appreciated that a right-to-left direction extends opposite to, or is rotated 180 degrees from, the left-to-right direction. These directions are so named because when the device 400 is inserted into a patient, the device will extend from a left side to a right side within the patient. These right-to-left and left-to-right directions could also be referred to as "lateral" directions. The proximal-to-distal, laryngeal-to-pharyngeal, and left-to-right directions are mutually orthogonal and provide a convenient reference coordinate system for describing the device.

As shown in FIG. 5A, the thickness of the inflated mask portion at the distal end 434 (i.e., the distance between the pharyngeal side 444 and the laryngeal side 448 of mask portion 430 as measured in the laryngeal-to-pharyngeal direction) shall be referred to as T4, and the thickness of the inflated mask portion at the proximal end 432, as measured in the laryngeal-to-pharyngeal direction, shall be referred to as T5. Preferred values for T4 and T5 in female adult sizes are about 12.7 and 25.4 millimeters, respectively. (It will be appreciated that external dimensions such as T4 and T5 would be about thirteen percent larger in an adult male size of the laryngeal mask airway device. Unless otherwise stated, dimensions discussed herein will be for the female adult size.) The profile of cuff 460 is preferably smoothly tapered as shown in FIG. 5A so that the thickness of the mask portion 430 smoothly decreases from the proximal end 432 to the distal end 434. This tapering can be described in terms of the angle alpha between the pharyngeal side 444 and the laryngeal side 448 of mask portion 430, as shown in FIG. 5A. One preferred value for the angle alpha is about ten degrees plus or minus one degree. More preferably, the angle alpha is ten degrees plus or minus half a degree. Most preferably, the angle alpha is substantially equal to ten degrees. As will be discussed below, this angle alpha is selected to match the human anatomy to allow all portions of the inflated cuff to contact the tissues surrounding the laryngeal inlet and to thereby provide improved seals.

The plate 440 shown in FIG. 5A is characterized by a substantially constant thickness. That is, the thickness T2 (as shown in FIG. 6) of plate 440 is substantially constant from the proximal end of the mask portion to the distal end of the mask portion and the variation in the mask portion's thickness is entirely provided by the cuff 460. However, as mentioned above, in some embodiments, it may be advantageous to provide plate 440 with a tapering thickness so that the distal end of the plate is thinner than the proximal end.

As shown in FIG. 5E, the length of the plate 440, or the distance between the proximal end 432 and the distal end 434 as measured in the proximal-to-distal direction, shall be referred to as L1, and the length of aperture 442 as measured in the proximal-to-distal direction shall be referred to as L2. The width of the plate 440, as measured in the left-to-right direction, shall be referred to as W1, and the width of the aperture 442 as measured in the left-to-right direction shall be referred to as W2. In adult sizes of device 400, preferred values for L1, L2, W1, and W2, are 90, 59, 47, and 26 millimeters, respectively.

Figure 8A:
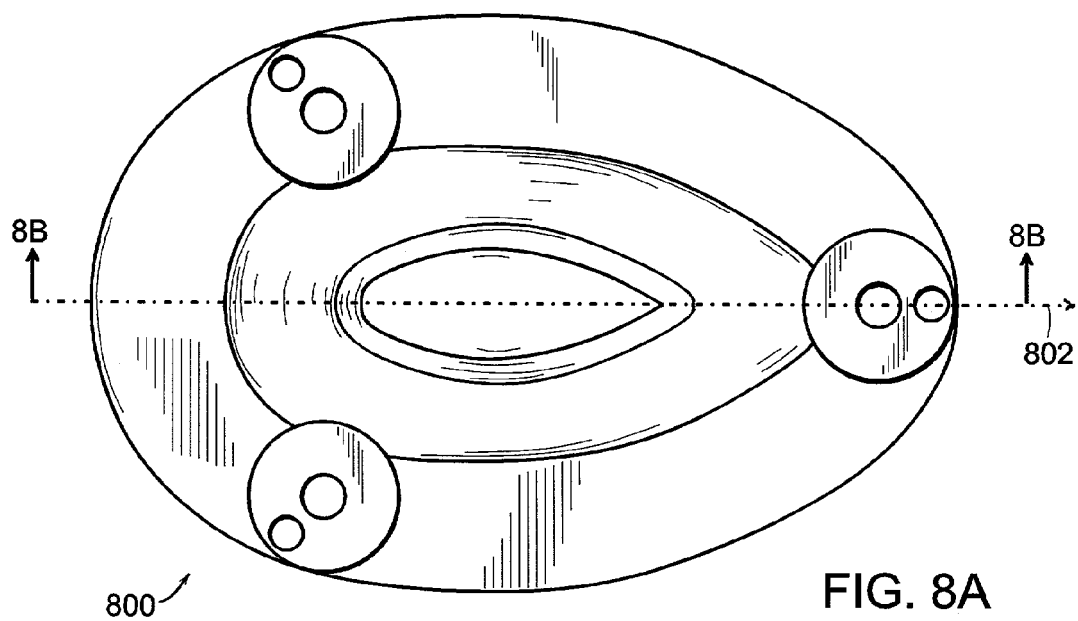
FIG. 8A shows a top view of a mold that may be used to make the mask portion shown in FIGS. 5–7.
Figure 8B:
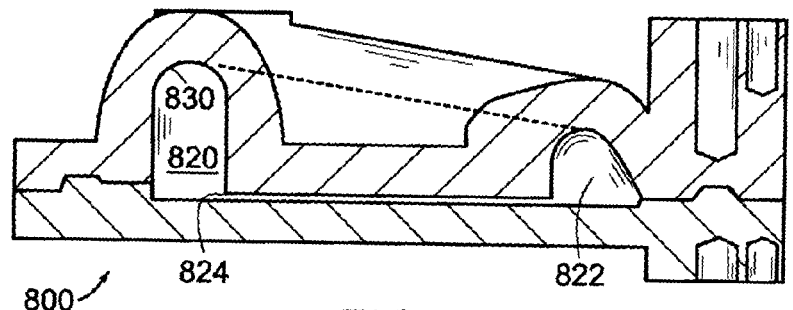
FIG. 8B shows a sectional view of the mold taken in the direction of line 8B—8B as shown in FIG. 8A.
Figure 8C:
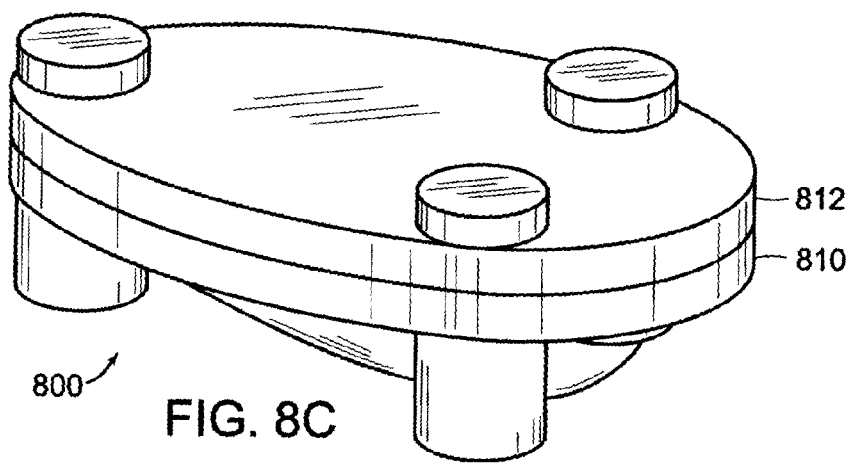
FIGS. 8C and 8D show perspective views of the mold shown in FIG. 8A.
Figure 8D:
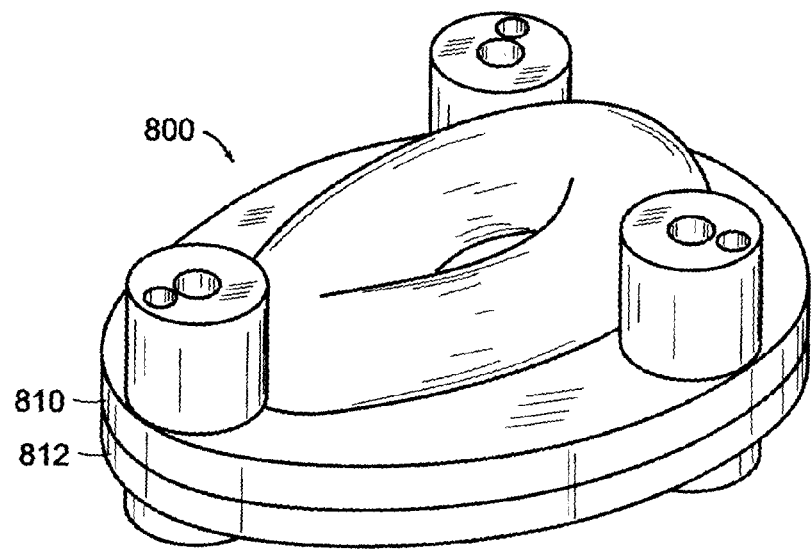

As stated above, mask portion 430 may be formed by a process called rotational molding. FIG. 8A shows a top view of a mold 800 that may be used to produce mask portion 430 by rotational molding. FIG. 8B shows a sectional view of mold 800 taken along the line 8B—8B as indicated in FIG. 8A. FIGS. 8C and 8D show perspective views of mold 800. As shown in FIG. 8A, the mold 800 is symmetric about an axis 802. As shown best in FIGS. 8C and 8D, mold 800 includes a top piece 810 and a bottom piece 812. When the top piece 810 and bottom piece 812 are bolted or clamped together, they cooperatively define a hollow interior volume 820 as shown in FIG. 8B. Interior walls 830 of the mold 800 define the boundaries of hollow interior volume 820.

One portion 822 of the interior volume 820 has a generally toroidal shape corresponding to the generally toroidal shape of the inflated cuff 460. Another portion 824 of the interior volume 820 has a generally elliptical shape corresponding to the shape of plate 440. That is, portion 824 defines a hollow volume, the shape of which is substantially identical to the flat, elliptical shape of plate 440. Similarly, the portion 822 defines a hollow volume, the shape of which is substantially identical to the shape of the inflated cuff 460.

In operation, mask portion 430 may be formed by adding or injecting a liquid plastic material (e.g., polyvinyl chloride or "PVC") into the interior volume 820 of mold 800 and by then rotating or otherwise moving mold 800 so as to coat the interior walls 830 with the liquid plastic material. Preferably, the mold 800 is simultaneously rotated about two axes that are at ninety degrees to each other (e.g., axis 802 and another axis that is perpendicular to axis 802). While the mold 800 is rotating, centrifugal forces cause the liquid plastic material to coat all portions of the interior walls 830 of mold 800. After all portions of the interior walls 830 have been so coated, the mold is then preferably held stationary in the position illustrated in FIG. 8B. That is, the mold 800 is preferably oriented so that the portion 824 of the hollow interior 820 is at the bottom of the mold (i.e., so that portion 824 is parallel to the ground and is closer to the ground, or lower, than any other portion of the hollow interior 820) while the mold 800 is held stationary. While the mold 800 is held in this stationary position, most of the liquid plastic material drains, or flows, down along the interior walls 830 into the portion 824. However, all of the liquid plastic material does not flow into portion 824. Rather, surface tension or other forces cause a thin coating of the liquid plastic material to remain in contact with the interior walls 830 that define the portion 822. The mold 800 is preferably held stationary long enough for the plastic material to cure and solidify before the mold is opened by separating the top and bottom pieces 810, 812.

The material that filled portion 824 forms the plate 440 of the mask portion 430. The thin coating of plastic material that lined the interior walls 830 of portion 822 forms a cuff 460 that is integrally attached to the plate 440. Air trapped within the interior volume 820 while the mask portion 430 is being formed becomes trapped within the cuff 460. So, when the mask portion 430 is removed from mold 800, the cuff 460 is partially inflated. The cuff 460 is only partially inflated (rather than fully inflated) when the mask portion 430 is removed from mold 800 because, as the mold cools, the trapped air shrinks in volume and accordingly only partially fills the interior volume defined by the cuff 460.

It will be appreciated that a variety of materials may be introduced into the mold 800 and used to form mask portion 430. The term liquid plastic material as used herein to refers to any material that is capable of curing from a liquid or fluid state to a solid, flexible or plastic, state. Due to its flexibility, resistance to stretching, and ability to define complex shapes such as that of inflated cuff 460, polyvinyl chloride is a preferred material to use as the liquid plastic material that forms mask portion 430. However, it will be appreciated that other materials could also be used.

Once the mold 800 has been opened and the cured plastic plate and cuff have been removed, fabrication of mask portion 430 may be completed by adding inflation tube 490. It will be appreciated that adding inflation tube 490 is a relatively simple step and is accomplished by forming an aperture in plate 440 that extends from the pharyngeal side 444 through the plate and into the interior volume defined by cuff 460, and then fixing inflation tube 490 to that aperture. Alternatively, as will be discussed below, it may sometimes be advantageous to provide a mask portion 430 that does not include an inflation tube. In these cases, fabrication of the mask portion is complete as soon as the cured, integrally formed, plate 440 and cuff 460 have been removed from the mold 800.

The cured mask portion is preferably relatively soft and flexible. In one exemplary embodiment, the durometer of the cured mask portion 430 is fifty five plus or minus ten on the Shore A scale of hardness. More preferably, the durometer of the cured mask portion 430 is fifty five plus or minus five on the Shore A scale of hardness. Most preferably, the durometer of the cured mask portion 430 is substantially equal to fifty five on the Shore A scale of hardness.

Figure 9E:
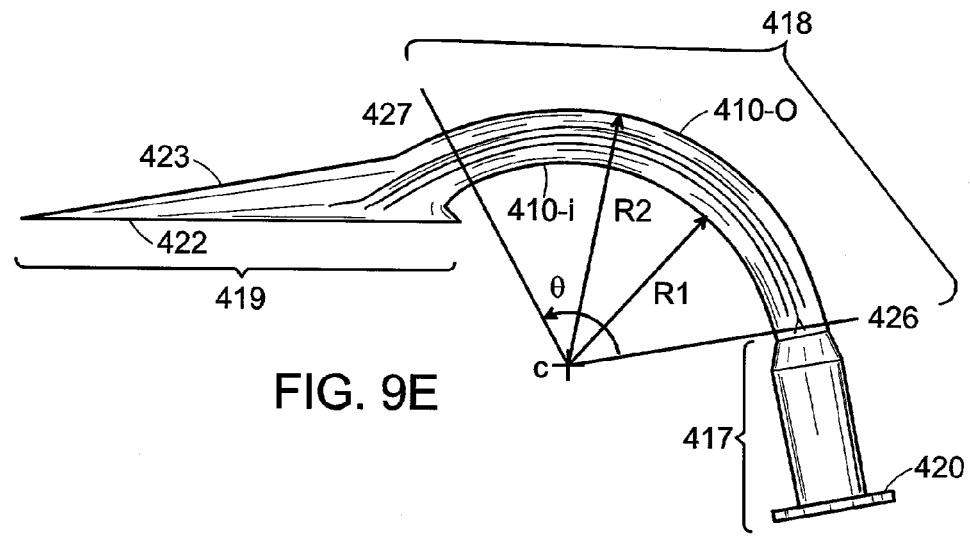
FIG. 9E shows a side view of the integral tube and backplate section of the airway tube shown in FIG. 9A.
Figure 9F:
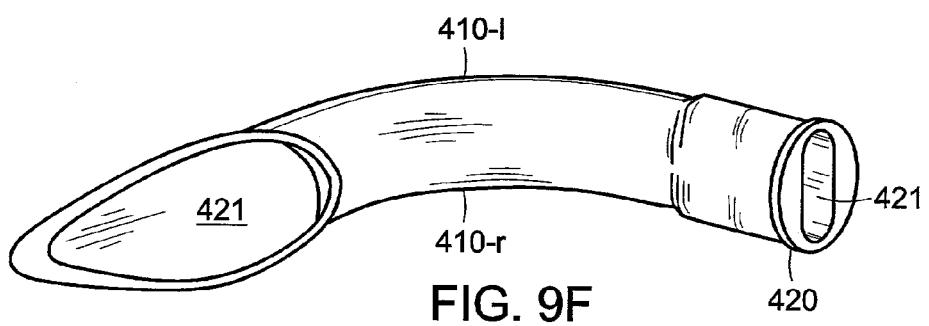
FIGS. 9F and 9G show two perspective views of the integral tube and backplate section shown in FIG. 9E.
Figure 9G:
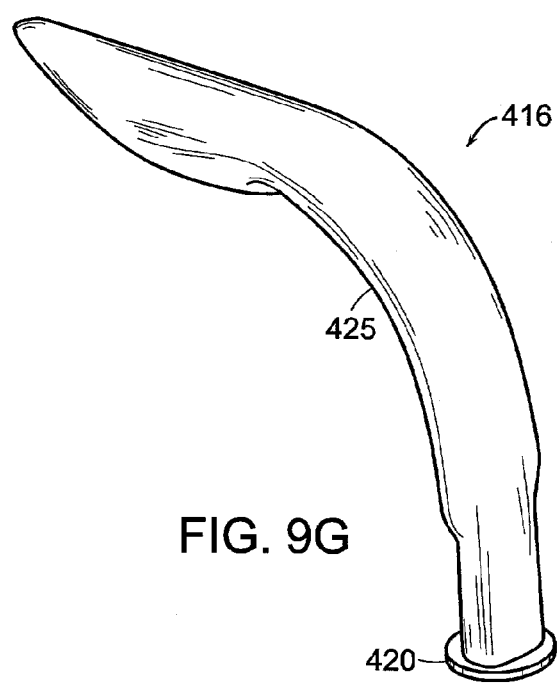

FIG. 9A shows a side view of airway tube 410, which includes a connector section 411 and an integral tube and backplate section 416. FIG. 9B shows a perspective view of connector section 411. FIGS. 9C and 9D show views of connector section 411 taken in the directions indicated by lines 9C—9C and 9D—9D, respectively, as shown in FIG. 9B. FIG. 9E shows a side view of integral tube and backplate section 416. FIGS. 9F and 9G show two perspective views of integral tube and backplate section 416.

Referring to FIGS. 9B, 9C, and 9D, connector section 411 includes a proximal portion 412 and a distal portion 413. Proximal portion 412 is preferably cylindrical and configured to couple to standard medical ventilating, or anaesthetic devices. Distal portion 413 is preferably oblong as shown best in the perspective view of FIG. 9B. Connector section 411 further includes a disk shaped plate, or flange, 414 that extends around the junction of proximal portion 412 and distal portion 413. Connector section 411 also defines a sealed internal airway passage 415 that extends entirely through the proximal portion 412 and the distal portion 413. In the proximal portion 412, the cross section of the passage 415 is circular, and in the distal portion 413, the cross section of the passage 415 is oblong.

Referring to FIGS. 9E, 9F, and 9G, integral airway tube and backplate section 416 includes a proximal portion 417, a central or curved portion 418, and a backplate portion 419. A disk shaped plate, or flange, 420 is integrally attached to the proximal end of proximal portion 417. Section 416 defines a hollow internal passage 421 that extends entirely through the proximal, curved, and backplate portions 417, 418, 419.

Airway tube 410 is assembled by coupling the connector section 411 and the integral airway tube and backplate section 416 together. As shown in FIG. 9A, when the parts are so coupled, the flange 414 of connector section 411 abuts the flange 420 of section 416. Also, the distal portion 413 of connector section 411 extends telescopically into the portion of internal passage 421 that is defined by proximal portion 417 of section 416. Also, the internal passage 415 of connector section 411 communicates with the internal passage 421 of section 416 so that the airway tube 410 defines a continuous sealed internal passage 424 (shown for example in FIGS. 10A and 10B) that extends from the tube's proximal end to the tube's distal end. Airway tube 410 also defines a left side 410-*l*, a right side 410-*r* (shown for example in FIG. 9F), an inner side 410-*i*, and an outer side 410-*o* (shown for example in FIG. 9E). Note that the left and right sides are defined with respect to a person (e.g., a physician) that is inserting the laryngeal mask airway device into a patient and that the left side 410-*l* of the tube will actually be disposed on the right side of the patient's natural airway when the device is in the fully inserted configuration.

Backplate portion 419 defines a laryngeal side 422 and a pharyngeal side 423. When the device 400 is assembled, the laryngeal side 422 of backplate portion 419 is attached or fixed to the pharyngeal side 444 of mask portion 430. Also, when the assembled device 400 is in the fully inserted configuration, the pharyngeal side 423 of the backplate portion 419 contacts the pharyngeal wall of the patient. When device 400 is assembled, the internal passage 424 of tube 410 communicates with the passage defined by mask portion 430 and the device 400 defines a sealed airway passage that extends from the proximal end of the tube 410 to the central aperture 442 of mask portion 430.

The airway tube 410 is sized so that when the laryngeal mask airway device is in the fully inserted configuration, the proximal portion 417 of the airway tube will be disposed between the patient's upper and lower teeth. FIG. 10A shows a cross-sectional view of the proximal section 417 into which the connector section 411 has been inserted taken along the line 10A—10A as shown in FIG. 9A. The airway tube 410 is also sized so that when the device is in the fully inserted configuration, the central portion 418 will extend through the patient's natural upper airway between the laryngeal inlet and the patient's teeth. FIG. 10B shows a cross sectional view of the central portion 418 taken along the line 10B—10B as shown in FIG. 9A. As shown in FIG. 10B (as well as FIGS. 9A and 9E), airway tube 410 defines longitudinal folds 425 that extend along the left and right sides of the central and backplate portions 418, 419.

Connector section 411 and integral tube and backplate section 416 of airway tube 410 are preferably formed using molding techniques such as injection or rotational molding. In one exemplary embodiment, connector section 411 is formed from polycarbonate and the material of section 411 is characterized by a durometer of 95 Shore A. Integral tube and backplate section 416 is preferably formed from a flexible plastic material (e.g., PVC) and is characterized by a durometer of 86 plus or minus 15 or 20 Shore A. More preferably, the material of integral tube and backplate section 416 is characterized by a durometer of 86 plus or minus 7 (or plus or minus ten percent) Shore A. Still more preferably, the material of integral tube and backplate section 416 is characterized by a durometer of 86 plus or minus 3.5 (or plus or minus 5 percent) Shore A. Most preferably, the material of integral tube and backplate section 416 is characterized by a durometer that is substantially equal to 86 Shore A.

Connector section 411 is preferably relatively hard so that (1) it is easy to reliably attach the proximal portion 412 of section 411 to standard breathing apparatus and (2) patient's can bite down on the distal portion 413 without causing collapse or shrinkage of the internal airway passage provided by section 411. Note that when the device is in the fully inserted configuration, the patient's teeth will contact proximal portion 417 of the integral tube and backplate section rather than section 411, because the distal portion of section 411 extends into the proximal portion 417 as illustrated in FIG. 9A. However, pressure applied by the patient's teeth will be transferred to section 411, and section 411 is preferably sufficiently hard to resist this pressure without allowing the internal passage 415 to collapse.

Section 416 is preferably softer than section 411 to facilitate bending the section 416 as necessary to insert the device into a patient and to permit unhindered flexion and extension of the patient's neck while device 400 is in the fully inserted configuration. However, as will be discussed below, section 416 is preferably stiff enough, at least at room temperature, so that laryngeal mask airway devices constructed according to the invention may be inserted by applying pressure to section 416 without requiring insertion of a finger into the patient's mouth.

Returning to FIGS. 4A–4C, it can be seen that device 400 may be formed by fixing or attaching the airway tube 410 to the mask portion 430. More specifically, the laryngeal side of the backplate portion of the airway tube is attached to the pharyngeal side of the mask portion so that the outer perimeter of the laryngeal side 422 of the backplate portion surrounds the central aperture 442 of the plate 440. The airway tube 410 may be attached to the mask portion 430 by heat sealing, gluing, or otherwise bonding or fixing the two components together.

As shown for example in FIG. 9F, the backplate portion 419 defines a "dome shaped" or "bowl shaped" interior volume. When the backplate portion 419 is attached to the mask portion 430, the backplate portion 419 and mask portion 430 cooperatively define a hollow bowl shaped interior volume as shown for example in FIG. 4C. As will be discussed below, portions of the larynx extend into this bowl shaped volume when the device is in the fully inserted configuration.

One advantage of device 400 is that it is relatively simple and inexpensive to produce. As discussed above, both the mask portion 430 and the airway tube 410 may be produced using a rotational molding process. The airway tube 410 may alternatively be produced using injection molding. Each of these steps (i.e., producing the mask portion 430 and producing the airway tube 410) is relatively simple and inexpensive. Fabrication of the device 400 may be completed by adding an inflation tube to mask portion 430 (in embodiments that use inflation tubes) and by attaching the airway tube 410 to the mask portion 430. Accordingly, devices 400 may be fabricated at very low cost. This low cost of fabrication enables laryngeal mask airway devices constructed according to the invention to be used as disposable devices. That is, the economics of constructing laryngeal mask airway devices according to the invention, such as device 400, enable them to be used once and then discarded.

Figure 3:
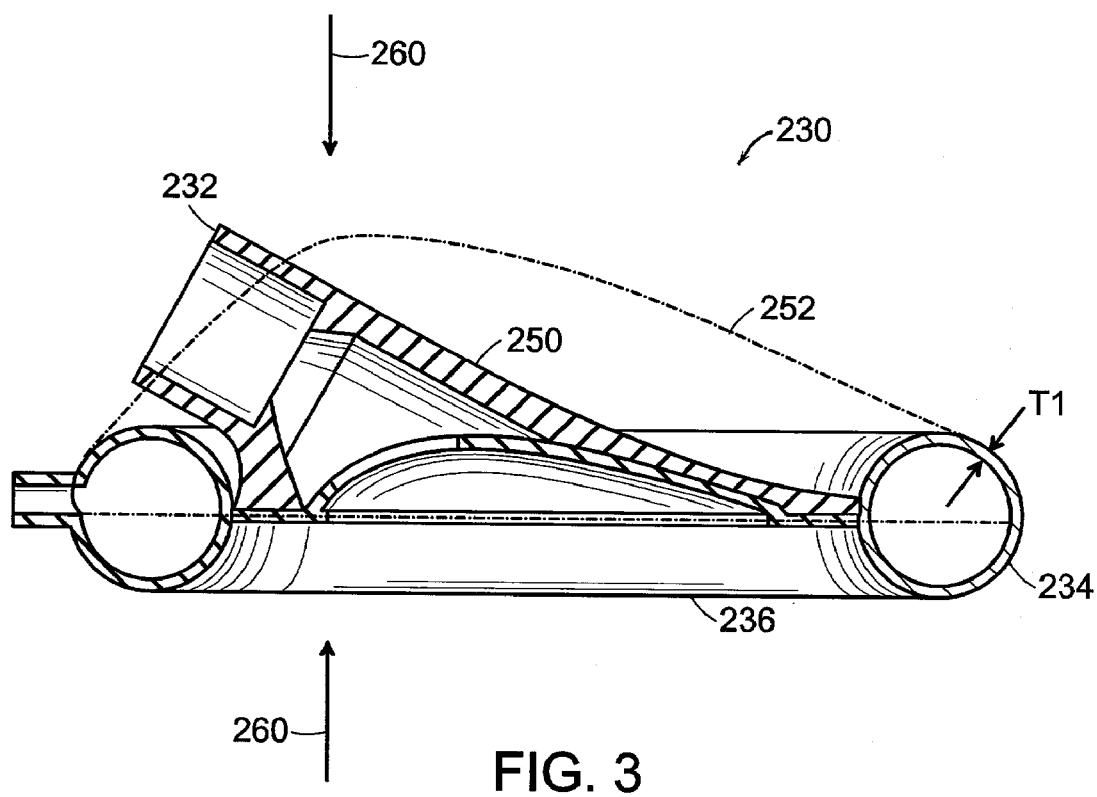
FIG. 3 shows a sectional view of another prior art laryngeal mask airway device.

Several structural advantages of laryngeal mask airway devices constructed according to the invention will now be discussed. As shown for example in FIGS. 4A–4C and 9A, the backplate portion 419 essentially forms a backplate of the device 400. In most prior art laryngeal mask airway device constructions (e.g., as shown in FIG. 3), the mask portion includes a backplate and defines a cylindrical aperture for receiving, or connecting with, a cylindrical airway tube. Forming the mask portion with an added backplate disadvantageously increases (1) the mechanical complexity of the mask portion and (2) the cost of fabricating the mask portion. Also, the junction, which is found in prior art laryngeal mask airway devices, of a cylindrical airway tube and a cylindrical aperture in a backplate tends to form a relatively stiff construction. For example, in the device illustrated in FIG. 3, it is relatively difficult to compress the junction of the cylindrical airway tube and the backplate in the direction indicated by arrows 260. Accordingly, this portion of prior art laryngeal mask airway device constructions disadvantageously forms a relatively thick, incompressible, structure that must be pushed between the patient's upper and lower teeth and past the patient's throat to insert the device. In contrast to those prior art constructions, the mask portions of laryngeal mask airway devices constructed according to the invention are formed without backplates (e.g., as shown in mask portion 430 in FIGS. 5A–5D) and the backplate of the device is provided by the airway tube. It is less complex, and less expensive, to provide the backplate as part of the airway tube. Also, eliminating the telescopic junction of two cylindrical components that characterized the prior art make laryngeal mask airway devices constructed according to the invention more compressible and easier to insert into patients. For example, referring to FIG. 4A, the backplate of device 400 compresses in the direction indicated by arrows 260 more easily than prior art laryngeal mask airway devices. This facilitates pushing laryngeal mask airway devices constructed according to the invention between the patient's upper and lower teeth and past the patient's throat.

Figure 1:
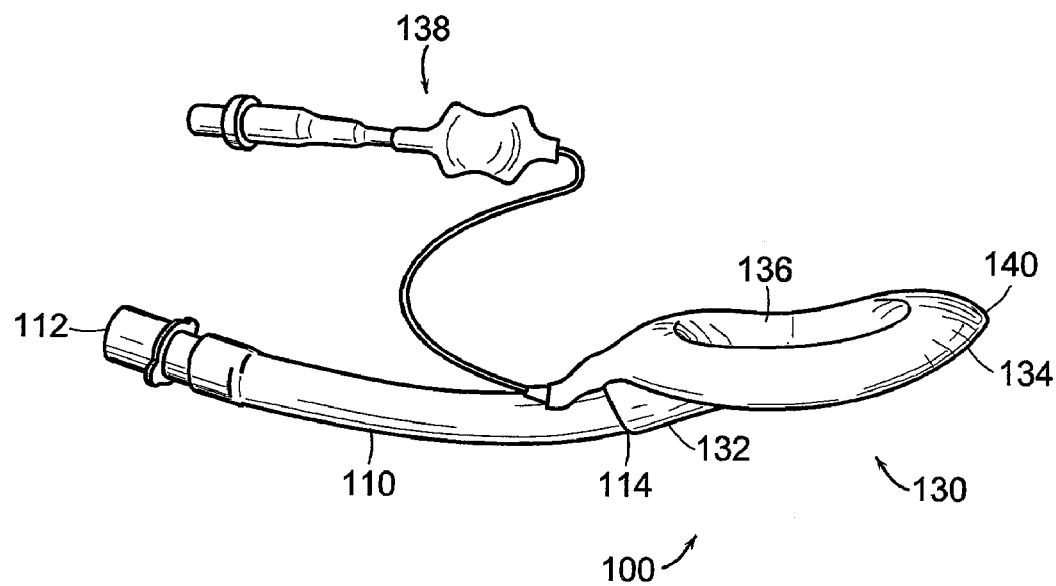
FIG. 1 shows a perspective view of a prior art laryngeal mask airway device.

In addition to providing a backplate, the general shape of the airway tube 410 distinguishes device 400 from prior art laryngeal mask airway devices. In most prior art laryngeal mask airway devices (e.g., as shown in FIGS. 1 and 3), the airway tube is cylindrical. While cylindrical airway tubes have functioned well for many years in many different models of laryngeal mask airway devices, the cylindrical configuration has some disadvantages. One critical feature for an airway tube of any laryngeal mask airway device is the size of the internal airway passage. This passage must be large enough to provide adequate ventilation of the patient's lungs. That is, moderate pressure differentials (e.g., a pressure drop of one to two cm $H_2O$) between the proximal and distal ends of the airway tube should be sufficient for moving a volume of air through the tube that is sufficiently large for adequately ventilating the patient's lungs. With a cylindrical airway tube it is easy to calculate the volume of air that can be moved through the tube for any given pressure differential, and the volume can be adjusted simply by adjusting (i.e., increasing or decreasing) the radius of the internal airway passage.

However, one constraint that should be considered in the design of airway tubes is that these tubes will extend through the patient's mouth, between the patient's upper and lower teeth, for as long as the laryngeal mask airway device remains in the fully inserted configuration. So, while a laryngeal mask airway device is inserted into a patient, the patient's mouth must remain opened wide enough to create an inter-dental gap (i.e., space between the upper and lower teeth) that is big enough to accommodate the airway tube. Holding the mouth open for long periods of time so as to create a large inter-dental gap can cause discomfort to the patient post operatively. More importantly, some patients cannot open their mouths wide enough to permit easy insertion of adequate sized cylindrical tubes. Accordingly, one disadvantage of cylindrical airway tubes is that they require a larger inter-dental gap than would a tube that had a flatter, or more oblong, cross section.

Another constraint that should be considered in the design of airway tubes is that these tubes will extend through the patient's natural upper airway for as long as the laryngeal mask airway device remains in the fully inserted configuration. This natural, or anatomical, upper airway, which is formed by several anatomical structures including the pharyngeal wall, hard and soft palates, and tongue, is not itself cylindrical. Accordingly, a cylindrical airway tube does not form a "good fit" with the anatomical upper airway. For example, when a cylindrical tube is extended through the anatomical upper airway, the tube tends to contact only isolated portions of the anatomical structures that define the anatomical upper airway. Accordingly, more pressure is applied to those structures, and those structures are subjected to more trauma, than would be the case if the shape of the tube better matched the shape of the anatomical upper airway.

As shown in FIGS. 9A, 9E, 9F, and 9G, the proximal and central portions 417, 418 of the airway tube 410 are oblong or flattened rather than cylindrical. As will be discussed in greater detail below, this advantageously (1) maximizes the size of the tube's internal airway passage; (2) minimizes the intra-dental gap required for accommodating the airway tube; and (3) allows the tube to fit well within, or match, the patient's natural airway.

As stated above, the airway tube 410 is sized so that the proximal section 417 will be disposed between the patient's upper and lower teeth when the laryngeal mask airway device is in the fully inserted configuration. As shown in FIG. 10A, the inter-dental gap G required to accommodate proximal section 417 is narrower than would be required if the proximal section 417 were cylindrical. Rather than a circular cross section, the cross section of the internal airway passage 424 is oblong. In one exemplary embodiment, the thickness G of the proximal section 417 is about 13.0 millimeters. The cross-sectional area of the internal passage defined by airway tube 410 is preferably at least as large as that of a cylindrical tube with a nine millimeter internal diameter passage. As shown in FIG. 10A, the width of the internal passage 424 may be referred to as W3 and the thickness of the internal passage 424 may be referred to as T6. In one exemplary embodiment, W3 and T6 are 20.0 and 6.7 millimeters, respectively.

As also stated above, the airway tube 410 is sized so that the central portion 418 will extend through the patient's anatomical upper airway while the laryngeal mask airway device is in the fully inserted configuration. As shown in FIG. 10B, the cross-section of the central portion 418 is oblong rather than cylindrical. Accordingly, the central portion 418 provides a "better fit" to the anatomical airway than do cylindrical tubes. As shown in FIG. 10B, the width of the central portion of the airway tube may be referred to as W4 and the thickness of the central portion of the airway tube may be referred to as T7. One preferred value for W4 is 23.7 millimeters plus or minus 10 percent (or plus or minus 2.37 millimeters) and one preferred value for T7 is 10.3 millimeters plus or minus 10 percent (or plus or minus 1.03 millimeters). More preferably, W4 and T7 are equal to 23.7 millimeters plus or minus 5 percent and 10.3 millimeters plus or minus 5 percent, respectively. Even more preferably, W4 and T7 are substantially equal to 23.7 millimeters and 10.3 millimeters, respectively. Also, the width W4 of the central portion of the airway tube is preferably equal to the thickness T7 times a factor of two, plus or minus ten percent (i.e., $W4=(2\pm0.2)\cdot T7$). More preferably, the width W4 is equal to the thickness T7 times a factor of two, plus or minus five percent (i.e., $W4=(2\pm0.1)\cdot T7$).

Figure 2:
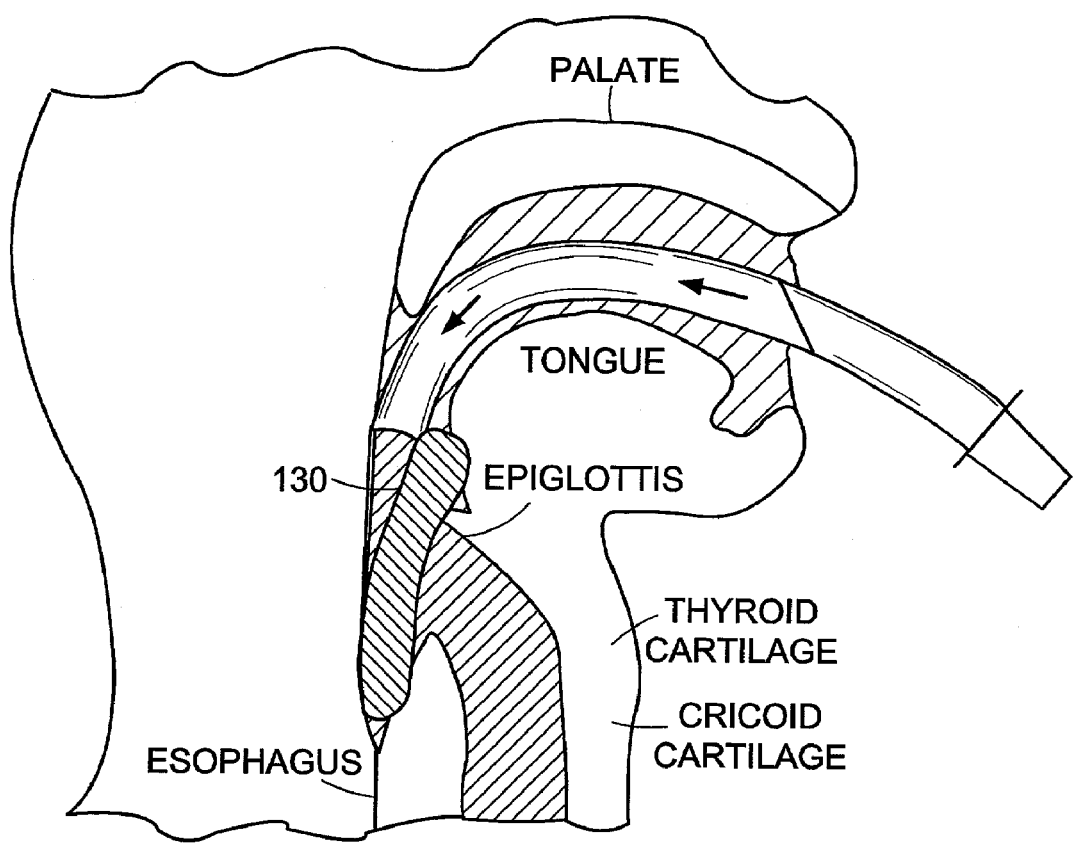
FIG. 2 shows a prior art laryngeal mask airway device inserted into a patient in the fully inserted configuration.

As shown in FIG. 2, the airway tube of any laryngeal mask airway device must follow a curve (about an axis extending in the left-to-right direction) from the point where it couples to the mask portion to the point where the patient's teeth contact the tube. This curve enables the tube to extend through the patient's natural upper airway from the teeth to the laryngeal inlet. One important design consideration for an airway tube of any laryngeal mask airway device is that the airway tube should be designed so that it does not form "kinks" when it is bent, or curved, as necessary for inserting the device into a patient.

Figure 11:
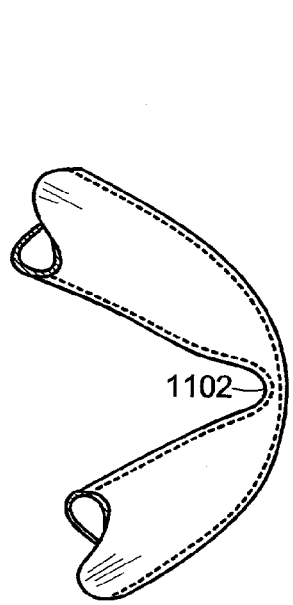
FIG. 11 shows a perspective view of a tube that has formed a kink in response to bending of the tube.

FIG. 11 shows an example of a tube that has formed a kink 1102 as a result of bending the tube by an extreme amount. As is well known, the size of the internal passageway defined by any tube is dramatically decreased at any such kinks 1102. The effects of kinks in tubes is commonly experienced in connection with garden hoses. For example, formation of a single kink in a garden hose can dramatically decrease the amount of water that can pass through the hose and be distributed by a sprinkler. The effects of kinks are similar in laryngeal mask airway devices. Any kinks forming in the airway tube of a laryngeal mask airway device essentially close off the tube's airway passage and dramatically decrease the volume of air that can pass through the tube. Accordingly, it is very important to design the airway tube so that kinks in the tube do not form when the tube is inserted into a patient.

One advantage of cylindrical airway tubes over tubes with flatter, or more oblong, cross sections is that for any given amount of bend, the cylindrical tube is less likely to form a kink. To reduce the risk that airway tube 410 forms any kinks, tube 410 is preferably provided with two longitudinal folds 425 that extend along the left and right sides of the tube's central and backplate portions 418, 419. As shown in FIG. 10B, the cross-section of the longitudinal fold 425 that extends along the left side of the airway tube defines a recess, or groove 425-g that extends from the left exterior edge of the airway tube towards the center of the tube in the left-to-right direction. Similarly, the cross-section of the fold 425 that extends along the right side of the airway tube defines a recess that extends from the right exterior edge of the airway tube towards the center of the tube in the right-to-left direction. Each of the recesses defines an upper exterior surface 425-u and a lower exterior surface 425-l. The thickness of the longitudinal folds 425 (i.e., the thickness as measured in a direction extending from the inner side 410-i to the outer side 410-o of the airway tube) may be referred to as T12 and the thickness of the longitudinal folds 425 as measured in the left-to-right direction may be referred to as T13. In one exemplary embodiment, the thickness T12 and T13 are about three millimeters and 2.7 millimeters, respectively.

Figure 10C:
FIG. 10C shows a sectional view of the same component illustrated in FIG. 10B when that component is subjected to external compressive forces.

As indicated in FIG. 10B, bending of the tube 410 (about an axis extending in the left-to-right direction) caused by inserting the laryngeal mask airway device through the patient's anatomical airway generates compressive forces in the directions indicated by arrows 260. The longitudinal folds 425 tend to prevent localized collapse of the internal passage 424 as a result of bending the tube. If the tube 410 is subjected to compressive forces in the direction of arrows 260 sufficiently large to deform the tube, the tube may deform to the shape illustrated in FIG. 10C. As shown, the deformation of the tube in the region of the longitudinal folds 425 may be likened to the movement of an accordion or concertina. The size of the internal passage 424 does decrease as the tube compresses from the profile shown in FIG. 10B to the profile shown in FIG. 10C. However, once the airway tube has reached the configuration shown in FIG. 10C, the longitudinal folds 425 resist additional decreases in the size of the passage 424, even in response to additional compression of the tube. So, airway tube 410 advantageously (1) reduces the size of the inter-dental gap required for accommodating the tube; (2) provides a large airway passage; (3) decreases the likelihood that the tube will form kinks when the laryngeal mask airway device is inserted into a patient; (4) decreases the likelihood that the tube will form kinks in response to bending of the patient's neck over the likely range of head movement; and (5) fits well within the patient's anatomical airway.

Figure 12:
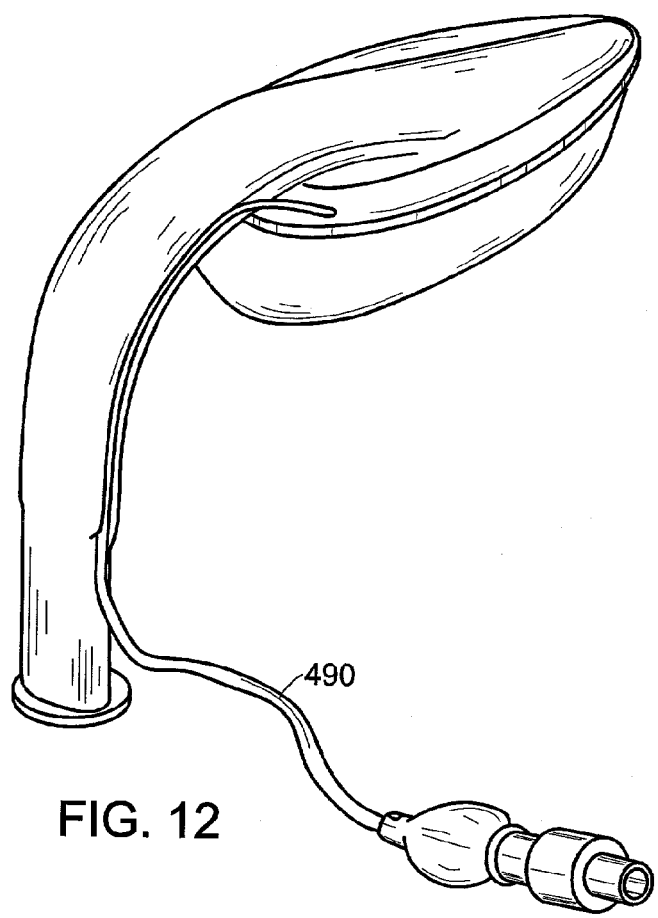
FIG. 12 shows a perspective view of a laryngeal mask airway device constructed according to the invention in which the inflation tube has been attached to the airway tube so that the inflation tube extends into one of the grooves in the airway tube.

Another advantage of the longitudinal folds 425 is that they provide a convenient groove 425-g for locating the inflation tube 490. FIG. 12 shows a perspective view of a device 400 constructed according to the invention in which the inflation tube 490 has been glued into the groove 425-g that extends along the right side of the airway tube.

Another important feature of the airway tube 410 is the degree of curvature through which the central portion 418 extends. As discussed in U.S. Pat. No. 6,079,409 (entitled, "Intubating laryngeal mask"), there is an optimum degree of curvature for the airway tube of a laryngeal mask airway device that will allow the patient to remain in a "neutral position" while the device is in the fully inserted configuration. The neutral position is a position in which the patient is lying on their back and in which the patient's head is positioned, for example with a pillow, so that the geometric relation of the head to the rest of the body is the same as when the patient is standing upright and looking forward. The device disclosed in the '409 patent used a rigid airway tube, and as discussed in that application, for rigid airway tubes the optimum degree of curvature is between 125 and 135 degrees. This degree of curvature permits the patient to remain in the neutral position while the laryngeal mask airway device is being inserted and after the device has been placed in the fully inserted configuration.

For convenience of exposition, the shape assumed by airway tube 410 when the tube is not subjected to any external forces shall be referred to as the "preformed configuration". As will be discussed below, since the airway tube 410 is somewhat flexible, it can deviate from the preformed configuration when the laryngeal mask airway device is in use. FIG. 9E shows the integral tube and backplate section 416 in its preformed configuration. As shown, the airway tube 410 is preferably manufactured so that when it is not subjected to any external forces, the central portion 418 follows a circular curve about an axis C (the axis C extending in the left-to-right direction and being perpendicular to the plane of the page in FIG. 9E) from a proximal limit of curvature 426 to a distal limit of curvature 427. In one exemplary embodiment, the angle theta between two rays extending from the axis C to the proximal and distal limits 426, 427 for the preformed configuration is 105 degrees plus or minus ten degrees. More preferably, the angle theta for the preformed configuration is 105 degrees plus or minus five degrees. Even more preferably, the angle theta is substantially equal to 105 degrees. In one exemplary embodiment of an adult female size, the distance, or radius, $R_1$, between the axis C and the inner surface 410-i of airway tube 410 for the preformed configuration is substantially equal to forty millimeters plus or minus about three millimeters, and the distance, or radius, $R_2$, between the axis C and the outer surface 410-o of airway tube 410 for the preformed configuration is substantially equal to fifty millimeters plus or minus about three millimeters.

The preferred degree of curvature for the preformed configuration of device 400 is different than for the rigid tube laryngeal mask airway device disclosed in the above-referenced '409 patent. This difference in curvature facilitates insertion of device 400. When a laryngeal mask airway device is inserted into a patient, proper insertion begins by placing the mask portion into the patient's mouth so that the pharyngeal side of the mask is in contact with the patient's hard palate. At this point, in devices designed according to the '409 patent, the curve in the rigid airway tube forces the proximal end of the airway tube to be pushed against the patient's chest. Positioning the end of the tube against the patient's chest makes inserting the device somewhat more difficult than if the proximal end could be positioned at a location that was spaced apart from the patient's body. However, the requirements of a rigid airway tube (which facilitates later insertion of an endotracheal tube) and allowing the patient to remain in a neutral position before, during, and after insertion, necessitates positioning the airway tube's proximal end against the patient's chest at the beginning of insertion.

Like the laryngeal mask airway device of the '409 patent, device 400 allows the patient to remain in a neutral position before, during, and after insertion. However, unlike the device of the '409 patent, the proximal end of the airway tube of device 400 need not be positioned against the patient's body at any time during insertion. If the airway tube 410 of device 400 were rigid and were formed with the above-discussed preformed configuration, then the patient could not remain in a neutral position while the laryngeal mask airway device was in the fully inserted configuration. Rather, the patient's head would have to be tilted backwards to allow the airway tube to fit into the patient's anatomical airway. However, since the airway tube 410 is not rigid, the tube can flex, or bend, slightly away from the preformed configuration as it is being inserted thereby allowing the tube to fit into the anatomical airway of a patient that is in the neutral position. The curve of the preformed configuration of the central portion 418 of the airway tube preferably does not deviate far from the anatomical curve of 125 to 135 degrees so that the tube need not bend much to fit into the anatomical airway. However, the curve of the preformed configuration of the central portion 418 preferably deviates somewhat from the anatomical curve of 125 to 135 degrees so as to eliminate the need for pressing the tube's proximal end against the patient's chest during insertion.

Figure 13:
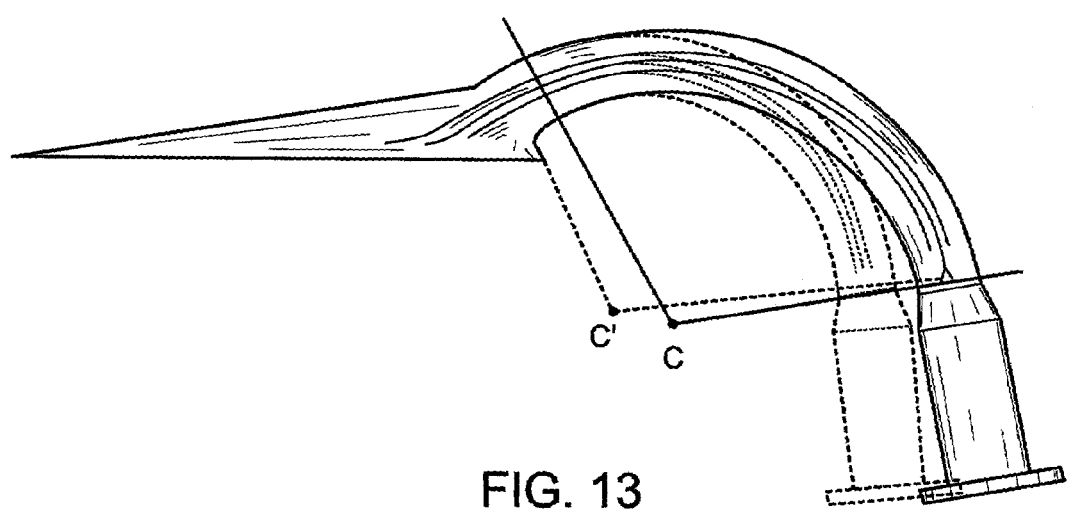
FIG. 13 illustrates how the airway tube shown in FIG. 9A deviates from its preformed configuration when the device is located in the fully inserted configuration.

FIG. 13 shows in solid lines a side view of integral tube and backplate section 416 in the preformed configuration. FIG. 13 also shows in dotted lines the shape that integral tube and backplate section 416 assumes after the device 400 has been located in the fully inserted configuration within a patient that is resting in the neutral position. As shown, the airway tube 410 bends about an axis extending in the left-to-right direction when the laryngeal mask airway device is inserted into a patient. When the laryngeal mask airway device is inserted into a patient, the center or curvature, or axis about which the tube bends, shifts from C to C', and the angle through which the tube bends changes from the 105 degrees (plus or minus five or ten degrees) of the preformed configuration to the 125 to 135 degrees required to fit within the anatomical airway of a patient lying in the neutral position.

As discussed above, in one exemplary embodiment, the integral airway tube and backplate section 416 is formed from polyvinyl chloride. This material is relatively stiff at room temperature but becomes much more flexible at body temperature. So, the airway tube is relatively stiff as the device 400 is being inserted into the patient. However, after the device 400 has been placed in the fully inserted configuration for a while (e.g., three to five minutes), the airway tube softens and becomes more pliable so that its shape easily accommodates to the shape of the patient's anatomical airway without placing undue force against the anatomical structures that define the anatomical airway. Also, since the material is relatively stiff at room temperature, the airway tube is generally stiff enough to act as an insertion tool. That is, device 400 may be entirely controlled during insertion simply by manipulating the portions of the airway tube 410 that extend outside of the patient's mouth. This eliminates the need for inserting a finger into the patient's mouth while inserting the laryngeal mask airway device and further eliminates the need for additional insertion tools.

Another important advantage of device 400 relates to the quality of the seal provided with the laryngeal inlet. As shown in FIG. 4A, there is a relatively large empty space S behind the mask portion 430. The empty space behind mask portion 430 is substantially larger than that provided by prior art laryngeal mask airway devices and, as will be discussed below, advantageously allows device 400 to provide improved seals.

As shown in FIG. 4A, the space S is defined by the distance T9 between the laryngeal side of the proximal end of the inflated cuff and the airway tube 410 as measured in the laryngeal-to-pharyngeal direction. A preferred value for the distance T9, when the airway tube is in the preformed configuration, is 32 millimeters plus or minus 3 millimeters. More preferably, the distance T9, when the airway tube is in the preformed configuration, is 32 millimeters plus or minus 2 millimeters. Even more preferably, the distance T9, when the airway tube is in the preformed configuration, is substantially equal to 32 millimeters.

When device 400 is in the fully inserted configuration, the posterior portion of the patient's tongue rests in the space S. As will be discussed below, enlarging the space S in which the tongue rests improves the quality of the seal between the proximal end of the inflated cuff and the patient's laryngeal inlet.

Figure 14:
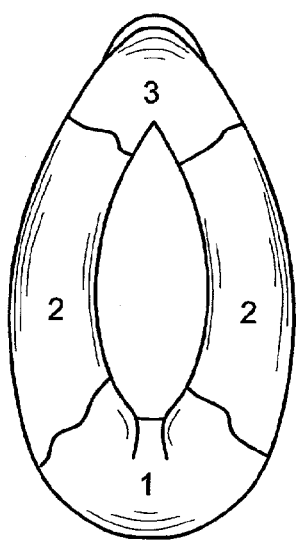
FIG. 14 shows a perspective view of the laryngeal side of the mask portion of a laryngeal mask airway device and illustrates the regions of the mask portion that form seals with different portions of the human anatomy when the device is located in the fully inserted configuration.

FIG. 14 shows a view of an inflated cuff of a laryngeal mask airway device, and the illustrated cuff has been divided into three different regions. When the device is located in the fully inserted configuration, each region of the cuff contacts a different portion of the patient's anatomy. Region 1, at the cuff's proximal end, fits into the patient's valleculae (i.e., the space behind the lower part of the tongue). Region 2, which is disposed between the cuff's proximal and distal ends, contacts the patient's pyriform fossae, which are symmetrically disposed on either side of the patient's glottic opening. Region 3, which is disposed at the cuff's distal end, contacts the patient's cricoid cartilage. Accordingly, when the laryngeal mask airway device is inserted into a patient, a seal that extends continuously around the patient's glottic opening is formed by contact between the inflated cuff and the patient's valleculae, pyriform fossae, and cricoid cartilage.

Figure 15A:
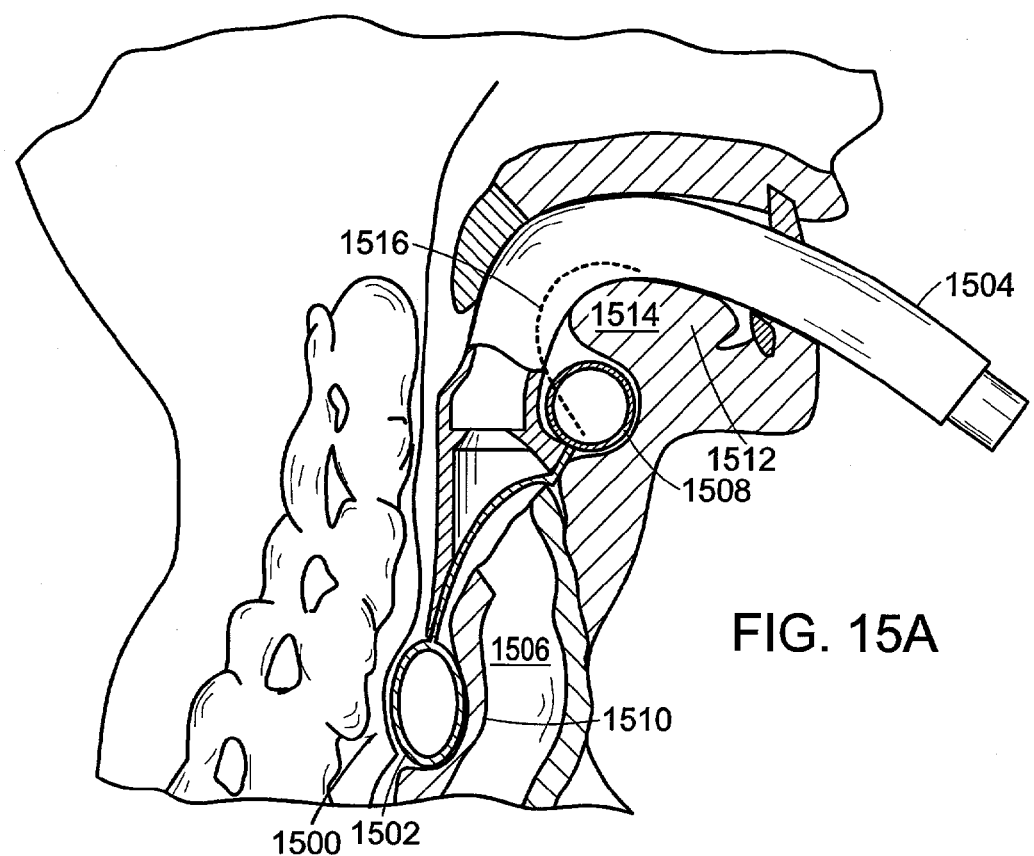
FIG. 15A shows a sectional view of a prior art laryngeal mask airway device that has been located in the fully inserted configuration.

FIG. 15A shows a prior art laryngeal mask airway device 1500 that has been placed in the fully inserted configuration. As shown, the inflated cuff 1502 has formed a seal around the patient's glottic opening thereby coupling the passage of the airway tube 1504 to the patient's trachea 1506. The laryngeal side of the proximal portion of the cuff fits into the patient's valleculae 1508, and the laryngeal side of the distal portion of the cuff contacts the patient's cricoid cartilage 1510. The patient's tongue 1512 is disposed generally along the inner, or anterior, side of the airway tube between the patient's teeth and the proximal end of the inflated cuff. The posterior portion 1514 of the patient's tongue 1512 is disposed in the space S (between the proximal end of the inflated cuff and the inner, or anterior, side of the airway tube). The dashed line 1516 illustrates the contour the tongue 1512 would follow if the device 1500 were not inserted into the patient. As shown, insertion of the laryngeal mask airway device displaces the tongue 1512 in the pharyngeal-to-laryngeal direction away from the natural position indicated by dashed line 1516. Pushing the tongue in this direction also pushes or levers portions of the larynx in the pharyngeal-to-laryngeal direction and thereby tends to prevent the cuff from fitting tightly around the larynx. This weakens the seal provided by the laryngeal mask airway device by decreasing pressure between the cuff and anatomical structures such as the pyriform fossae.

Figure 15B:
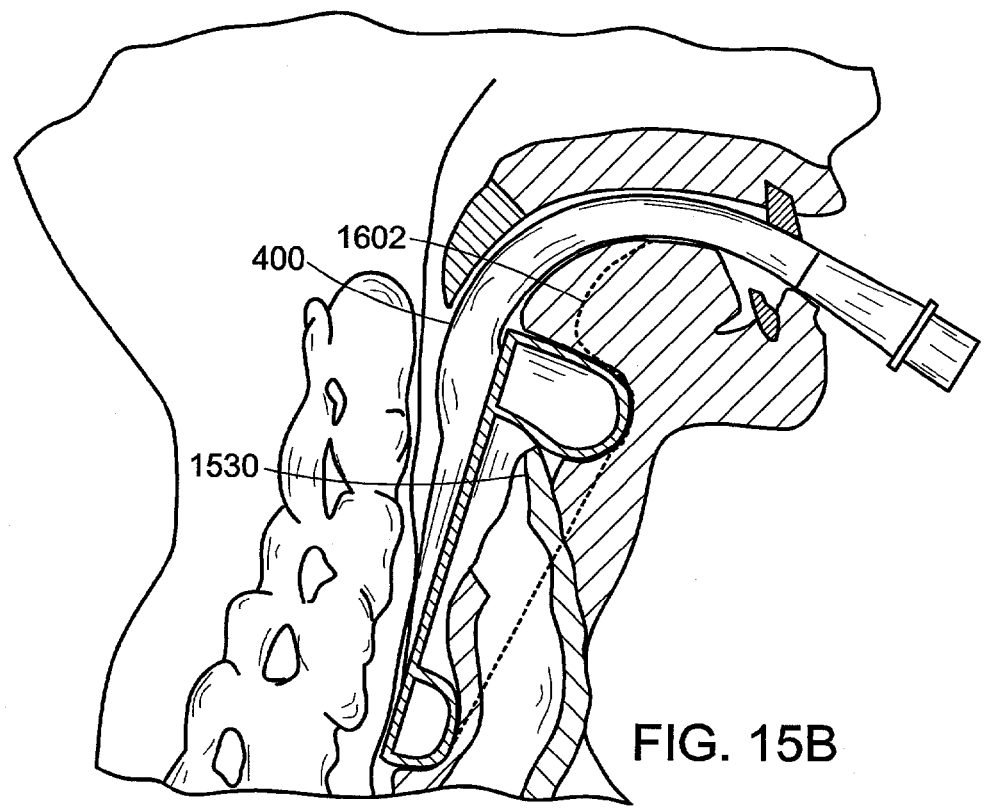
FIG. 15B shows a sectional view of a laryngeal mask airway device constructed according to the invention that has been located in the fully inserted configuration.

FIG. 15B shows device 400 in the fully inserted configuration. The dashed line 1602 represents the contour assumed by the tongue when prior art device 1500 is in the fully inserted configuration. As shown, the enlarged empty space S provided by device 400 allows the tongue to assume a more natural position than prior art device 1500. In particular, the enlarged empty space S of device 400 allows the tongue to be displaced in the laryngeal-to-pharyngeal direction from where the tongue would be if device 1500 were in the fully inserted configuration. Allowing the tongue to assume a more natural position also allows other anatomical structures to assume a more natural position (i.e., to be displaced in the laryngeal-to-pharyngeal direction from where they would be if device 1500 were in the fully inserted configuration) and thereby improves the seal provided by device 400.

As is well known, portions of the larynx (e.g., the ariepiglottic folds) can extend into the bowl shaped space bounded by the inflated cuff when a laryngeal mask airway device is in the fully inserted configuration. FIG. 15B suggests this by showing structures 1530 extending into the bowl-shaped volume defined by the cuff and backplate of device 400. Enlarging the space S also has the beneficial effect of increasing the size of the bowl-shaped volume defined by device 400 (i.e., increasing the empty space that is bounded by the backplate portion and the inflated cuff of device 400). This also improves the quality of the seal provided by device 400 by allowing the larynx to extend further into the bowl-shaped volume than was possible with prior art laryngeal mask airway devices. Allowing the larynx to extend further into this space allows the larynx to assume a more natural position (i.e., a position similar to the position the larynx would occupy if the laryngeal mask airway device were not inserted) and improves the seal provided by the laryngeal mask airway device.

Several features of device 400 cooperate to provide the enlarged empty space S. First, as shown in FIG. 5A, the thickness T5 of the proximal portion of the mask portion is substantially thicker than the thickness T4 of the distal portion of the mask portion. Another feature that cooperates to define the enlarged empty space S is the angle between the central portion 418 and the backplate portion 419 of the airway tube. As shown in FIG. 4A, at the junction of the central portion 418 and the backplate portion 419, the central portion 418 extends at an angle alpha with respect to the plate 440. In one exemplary embodiment, the angle alpha is equal to ten degrees plus or minus two degrees. More preferably, the angle alpha is equal to ten degrees plus or minus one degree. Even more preferably, the angle alpha is substantially equal to ten degrees. This angle provides additional clearance between the proximal end of the plate and the inner side of the airway tube as measured in the laryngeal-to-pharyngeal direction. Yet another feature that contributes to defining the empty space is an absence of an inflation tube in the space. In most prior art laryngeal mask airway devices, as shown for example in FIG. 3, the inflation tube extends from the proximal end of the cuff in the distal-to-proximal direction into the space. However, in device 400, as shown for example in FIG. 12, the inflation tube does not extend from the proximal end of the cuff and instead extends from the pharyngeal side of the plate to one of the notches 425 without entering the space S.

As discussed above, and as illustrated in FIGS. 5A–5C and 15B, one feature that helps define the enlarged empty space S is the increased thickness of the proximal end of the inflated cuff. When device 400 is in the fully inserted configuration, the inflatable cuff may preferably be inflated to a pressure of about 60 cm $H_2O$.

The pressure in silicone cuffs tends to increase during surgical procedures because commonly used anesthesia gasses (e.g., nitrous oxide) tend to diffuse through the semipermeable cuff wall. One advantage of forming mask portion 430 out of PVC is that the anesthesia gasses do not tend to diffuse into the cuff and change the intra-cuff pressure during a surgical procedure.

Figure 16A:
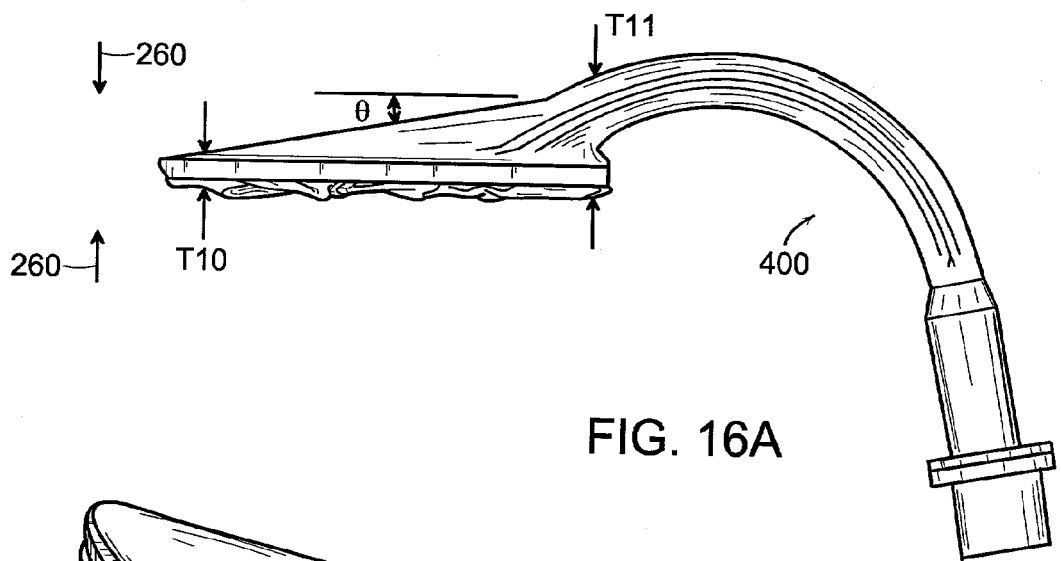
FIG. 16A shows a side view of the device shown in FIG. 4A when the mask portion is deflated.
Figure 16B:
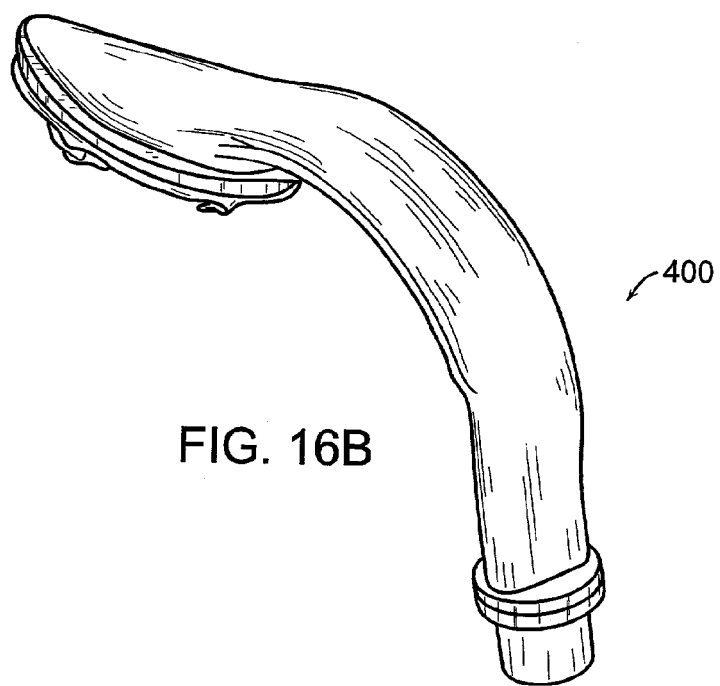
FIGS. 16B and 16C show perspective views of the device, with deflated mask portion, shown in FIG. 16A.
Figure 16C:
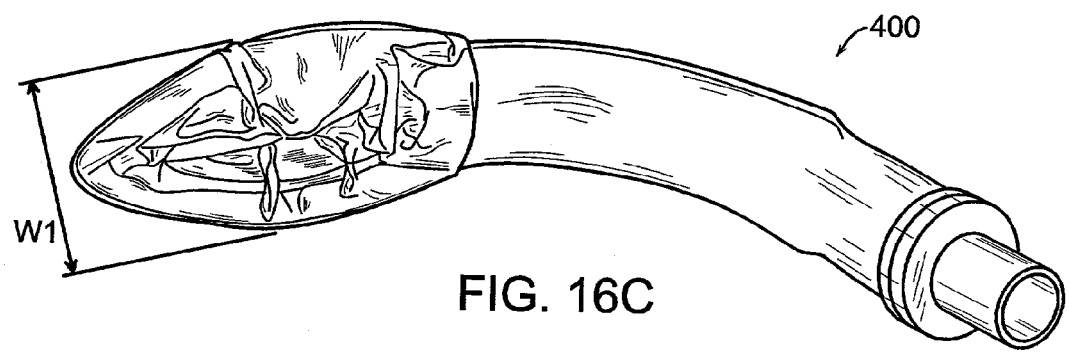

Yet another advantage of device 400 relates to the ease with which it can be inserted into a patient. FIG. 16A shows a side view of device 400 when the cuff 460 is deflated. FIGS. 16B and 16C show perspective views of device 400 when the cuff 460 is deflated. The thickness T3 (as shown in FIG. 6) of the cuff is sufficiently thin, that when the cuff 460 is deflated, the profile of the distal portion of the laryngeal mask airway device is almost entirely determined by the plate 440 of the mask portion and the backplate portion 419 of the airway tube. As shown in FIG. 16A, the thickness T10 of the distal end, as measured in the laryngeal-to-pharyngeal direction, is virtually entirely determined by the thickness of the plate 440. The thickness of the deflated laryngeal mask airway device, as measured in the laryngeal-to-pharyngeal direction, gradually increases with increases in the distal-to-proximal direction until the thickest point, at the proximal end of the mask portion, is reached which has a thickness T11, as measured in the laryngeal-to-pharyngeal direction. The rate of increase in thickness is determined by the angle theta between the plate 440 and the pharyngeal side of backplate portion 418. In exemplary embodiments, the angle theta is about eleven degrees and the thickness T10 is about two millimeters (i.e., the deflated cuff adds virtually no thickness beyond the thickness of the plate T2). The thickness T11 is preferably about seventeen millimeters plus or minus two millimeters. More preferably, the thickness T11 is about seventeen millimeters plus or minus one millimeter. Even more preferably, the thickness T11 is substantially equal to seventeen millimeters. The thickness T 11, which is the thickest part of deflated device 400 as measured in the laryngeal-to-pharyngeal direction, is relatively thin as compared with prior art laryngeal mask airway devices, which are usually about twenty-six millimeters thick in comparable sizes.

FIG. 16C illustrates the size of the deflated device 400 as measured in the left-to-right direction. The width of the distal tip of the laryngeal mask airway device is relatively narrow and the width of the device gradually increases with increases in the distal-to-proximal direction. The width of the widest part of the deflated laryngeal mask airway device, as measured in the left-to-right direction, W1 is equal to the width of the widest part of the plate (as shown in FIG. 5E).

The overall profile of deflated device 400, as measured in the laryngeal-to-pharyngeal direction, as well as the left-to-right direction, is small as compared with prior art deflated laryngeal mask airway devices. Having such a small profile greatly increases the ease with which deflated device 400 may be inserted into a patient. In particular, the thin profile, as measured in the laryngeal-to-pharyngeal direction, makes it very easy to push the deflated mask portion and backplate between a patient's upper and lower teeth and past the patient's throat. The thin profile also increases the likelihood that the deflated mask portion will fit between the pharyngeal wall and the epiglottis without disturbing or otherwise pushing on the epiglottis as the distal tip of the mask portion is being pushed past the epiglottis towards the esophageal sphincter.

Figure 17:
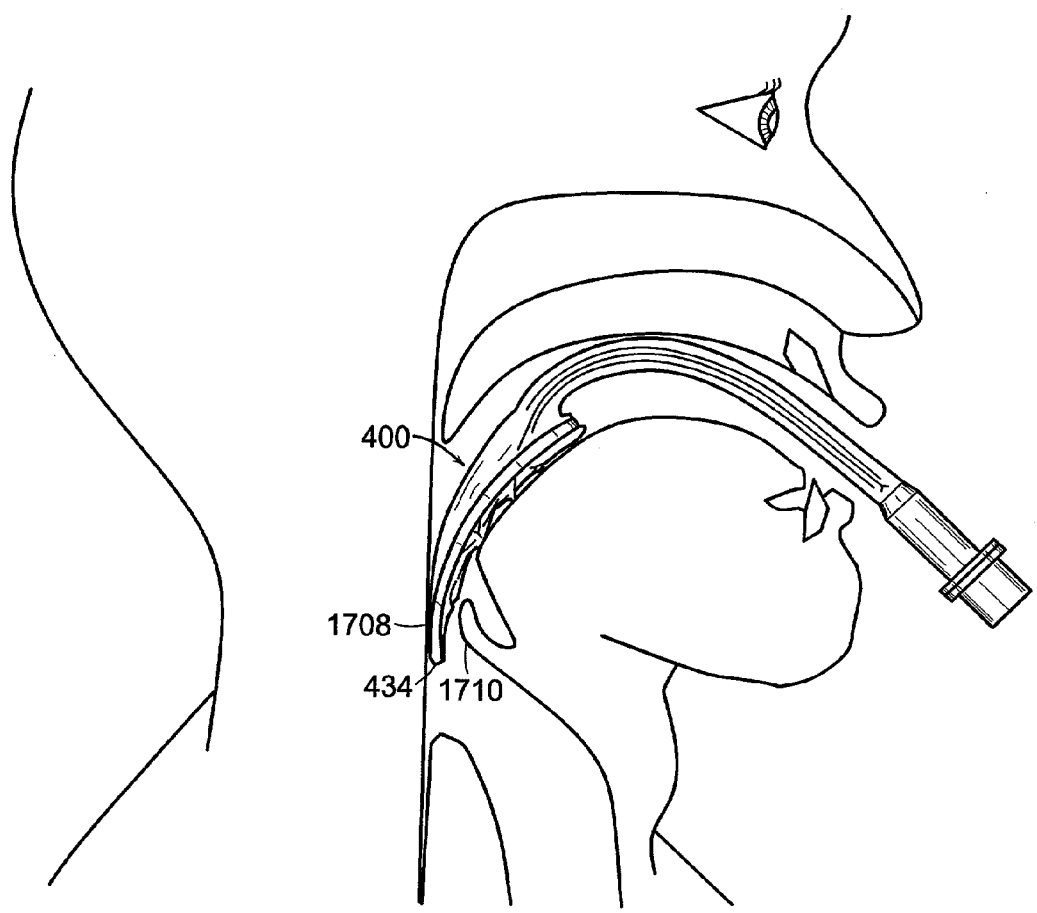
FIG. 17 shows a laryngeal mask airway device constructed according to the invention that is partially inserted into a patient.

FIG. 17 shows a deflated device 400 that has been partially inserted into a patient that is resting in the neutral position. As shown, the distal tip 434 of the deflated laryngeal mask airway device has fit between the patient's pharyngeal wall 1078 and the epiglottis 1710. When an unconscious patient lies on their back, relaxation of the muscles tends to allow the back of the tongue and the epiglottis to drop down towards the pharyngeal wall, thereby reducing or minimizing the space between the epiglottis and the pharyngeal wall. Accordingly, the thinner the deflated laryngeal mask airway device, the more likely it is that the device will fit into the space between the pharyngeal wall and the epiglottis without pushing on or otherwise moving the epiglottis. The slim profile of deflated device 400 accordingly facilitates proper insertion of the device.

One problem with prior art laryngeal mask airway devices is that they are often inserted improperly. As discussed above, the laryngeal mask airway device is a "forgiving" device and tends to establish an airway even when the device is improperly inserted. However, ideally, the laryngeal mask airway device should be inserted properly so that the epiglottis is not disturbed and so that the distal tip of the device is disposed adjacent the esophageal sphincter. One problem that contributes to the difficulty of inserting prior art laryngeal mask airway devices relates to the profile assumed by the deflated cuff. In prior art laryngeal mask airway devices, the deflated cuff forms a "structural component" of the device in that (1) a significant portion of the profile of a deflated prior art laryngeal mask airway device is determined by the cuff and (2) the shape of the deflated cuff significantly affects the path taken by the device through the body as it is inserted into a patient. Accordingly, proper insertion of a prior art laryngeal mask airway device generally requires properly forming, or shaping, the cuff as it is deflated. U.S. Pat. No. 5,711,293 discloses an example of a prior art forming tool for forming a laryngeal mask airway device into an ideal shape for insertion as the cuff is being deflated.

In device 400, the deflated cuff contributes only insignificantly to the profile of the deflated laryngeal mask airway device. Rather, the profile of the deflated device is determined almost entirely by the plate 440 of mask portion 430 and the backplate portion 419 of airway tube 410. As shown in FIGS. 16A–C, these components define a slim profile that facilitates proper insertion of the device.

Another advantage of device 400 relates to the profile of the device when deflated as compared with the profile of the device when inflated. As discussed above, when device 400 is deflated it presents a slim, thin, or small profile as compared with prior art laryngeal mask airway devices. However, when device 400 is inflated, the cuff expands considerably and, as discussed above, this allows the device to provide an improved seal with the tissues surrounding the patient's glottic opening. The relatively large difference between the thickness (as measured in the laryngeal-to-pharyngeal direction) of the deflated device as compared with the thickness of the inflated device distinguishes device 400 from prior art laryngeal mask airway devices. As discussed above, the thickest part of the deflated device 400, T11, is about seventeen millimeters. The thickest part of the inflated device 400, T5, is about 25.4 millimeters. Accordingly, the thickest part of the inflated device 400 is approximately 1.5 times larger than the thickest part of the deflated device 400. Although 1.5 is a preferred factor for distinguishing the thickest parts of the inflated and deflated device, it may be preferable for the thickest part of the inflated device to be 1.5, plus or minus 0.15, times larger than the thickest part of the deflated device (i.e., T5= (1.5±0.15)·T11).

As shown in FIG. 17, any laryngeal mask airway device will bend or flex as the device is being inserted into a patient. More specifically, as the distal tip of the laryngeal mask airway device contacts the patient's palato-pharyngeal arch, the distal tip bends down towards the larynx (or bends about an axis that extends in the left to right direction). As the device is inserted further into the patient, the portion of the device that is proximal to the palato-pharyngeal arch will bend around the arch and portions of the device that have already passed by the palato-pharyngeal arch will straighten out. In this manner, the point of bending or flexing begins at the laryngeal mask airway device's distal tip and moves backwards in the distal-to-proximal direction as the device continues to be inserted into the patient.

As shown for example in FIG. 16B, the backplate portion 419 of device 400 is "spear shaped" or tapered in that its width decreases with increases in the proximal-to-distal direction. The very narrow width of the backplate's distal tip makes the device's distal tip relatively flexible so that the distal tip easily bends or flexes downwards towards the larynx as the device 400 is inserted into the patient. As the device 400 is inserted further, and the device's resistance to bending increases in a linear fashion due to the gradual widening of the "spear shaped" backplate portion. This linear increase in resistance to bending about an axis that extends in the left-to-right direction is an advantageous feature of device 400. If the increase in resistance were not linear and instead increased suddenly or dramatically (in a non-linear fashion) at one or more points as the device was being inserted, the device would tend to kink, or form a localized fold, instead of bending smoothly around the palato-pharyngeal arch. Such a kink-like deformation would be more stimulating to the patient and increase the likelihood of malposition and/or trauma during insertion. Some prior art laryngeal mask airway devices are capable of offering a substantially linear increase in resistance to bending as the device is inserted into a patient as long as the cuff has been properly deflated and formed into a proper configuration. However, since the cuff of these prior art laryngeal mask airway devices forms a structural component of the device, they do not offer a linear increase in resistance to bending, and tend to form kinks while being inserted, when the cuff is deflated without proper use of a forming tool. One advantage of device 400 is that the laryngeal mask airway device will provide the desired substantially linear increase in resistance to bending regardless of the manner in which the cuff is deflated. This is so because the deflated cuff does not contribute significantly to the structure of the device and the device's resistance to bending is virtually entirely determined by the geometry of the backplate portion 419.

Yet another advantage of device 400 relates to the size of the inflated cuff. As shown for example in FIGS. 5A and 15A, the thickness T5, as measured in the pharyngeal-to-laryngeal direction, of the proximal end of the inflated cuff is relatively large as compared with prior art laryngeal mask airway devices. The relatively large thickness T5 of the proximal end of the inflated cuff advantageously increases the separation between the epiglottis and the aperture 442 of plate 440 and thereby decreases the likelihood that the epiglottis can block the airway provided by the device 400. Prior art laryngeal mask airway devices often included "bars" or "slits" disposed in the mask portion to prevent the epiglottis from blocking the airway of the device. Such bars are disclosed for example in U.S. Pat. No. 5,297,547 (see FIG. 8 of the '547 patent). Although laryngeal mask airway devices constructed according to the invention could include such "bars", device 400 advantageously eliminates the need for such bars and accordingly may be manufactured less expensively.

Returning to FIG. 17, as shown the distal tip of device 400 has passed through the gap between the epiglottis and the pharyngeal wall. Sometimes the distal tip of the device will catch on the epiglottis as the device is being inserted and will push the epiglottis into a "down folded" condition. In such a "down folded" condition, the epiglottis may block the trachea or the airway provided by a laryngeal mask airway device. Another advantage of device 400 is that the cuff 460 can lift a down folded, or posterior lying, epiglottis forwards, or anteriorly, thereby keeping the airway clear. FIG. 7B illustrates a preferred folded configuration for the deflated cuff. As shown, when the cuff 460 is deflated, the extra or loose material of the cuff may be folded towards the center of the mask portion so that the deflated cuff covers the entire, or nearly the entire, central aperture 442 of plate 440. If the cuff is folded into this position so that it covers the entire, or nearly the entire, central aperture 442, then the cuff 460 will advantageously lift the epiglottis anteriorly and thereby open the airway as the cuff is inflated.

One disadvantage of prior art re-usable laryngeal mask airway devices is that after every sterilization, the cuff must be deflated and the device must be configured for insertion into a patient. Unfortunately, most physicians who use laryngeal mask airway devices lack the skill or dedication required to pack the device into the optimal configuration for facilitating insertion. Another advantage of device 400 is that when it is used as a disposable device, the laryngeal mask airway device may be packaged and sold in a configuration that is optimal for facilitating insertion of the device into a patient. As discussed above, device 400 is advantageous because (1) the deflated cuff only adds a small amount of thickness to the mask portion and (2) the deflated cuff may be configured for lifting a down folded or posterior lying epiglottis out of the way. Preferably, the device 400 is placed into this optimal configuration (i.e., with the cuff deflated and folded as discussed above in connection with FIGS. 7A and 7B) prior to sale and then packaged into a sterile bag or package (e.g., a sterile plastic bag). So, when a physician wishes to insert a laryngeal mask airway device into a patient, the physician may simply remove a device from its sterile packaging and insert it into the patient without having to first deflate or reposition the cuff.

As discussed above, in some embodiments of device 400 an inflation tube 490 need not be provided. So, in embodiments that do not include inflation tubes, fabrication of the laryngeal mask airway device is completed by attaching the airway tube to the partially inflated mask portion after the mask portion is removed from the mold. When mask portion 430 is formed by rotational molding, the cuff is partially inflated when the mask portion is removed from the mold. The amount of air that is trapped in the cuff during fabrication is similar to the amount of air that is normally injected into the cuff via the inflation tube after the mask portion has been inserted into a patient to achieve the desired intra-cuff pressure of 60 cm $H_2O$. Accordingly, such a partially inflated cuff is capable of forming an effective seal around a patient's laryngeal inlet.

These masks have one principal disadvantage as compared with embodiments of device 400 that do include an inflation tube. The profile of the partially inflated cuff is thicker, as measured in the proximal-to-distal direction, than is achievable in device 400 when the cuff is fully deflated via the inflation tube, and this can make inserting the laryngeal mask airway device more difficult. However, laryngeal mask airway devices that do not include an inflation tube do have one principal advantage. Namely, they can be easier and faster to use in emergency situations because the practitioner need not bother with deflating or inflating the cuff, and the airway is established as soon as the mask portion is inserted into the patient's pharynx. The thicker profile can complicate insertion of such a laryngeal mask airway device. However, two factors make the insertion easier than might otherwise be the case. First, in unconscious patients, the muscles of the body become very relaxed which can make it easier to push a thick profile device through the upper and lower teeth and down the throat. Second, since the cuff is only partially inflated, and since the cuff is very thin and flexible, a very small amount of pressure applied to one portion of the cuff will squeeze, or shrink the size of that portion, and force air trapped in the cuff into other portions of the cuff thereby inflating or expanding those other portions. For example, the proximal end of the cuff will expand if the distal end is squeezed flat, and only a very small pressure is required to squeeze the distal end into a flat shape. As a device 400 with a partially inflated cuff is inserted into a patient, some parts of the cuff may expand while other parts are squeezed by anatomical structures. However, the ability to shrink in some places while expanding in others makes it relatively easy to push the partially inflated cuff into the patient's pharynx.

Accordingly, one method of making a laryngeal mask airway device according to the invention is to (1) produce mask portion 430 using the rotational molding process described above in connection with FIGS. 8A–8D; (2) remove mask portion 430 from the mold 800; and (3) attach an airway tube to the mask portion. The rotational molding process produces a partially inflated mask portion that is inflated to a suitable degree. Once the airway tube is attached to the mask portion, fabrication of the laryngeal mask airway device is complete. An inflation tube need not be added. The completed laryngeal mask airway device may be packaged for sale in a sterile bag. Such laryngeal mask airway devices may be very useful for emergency situations, for example for use by emergency workers in ambulances or emergency wards.

Figure 18A:
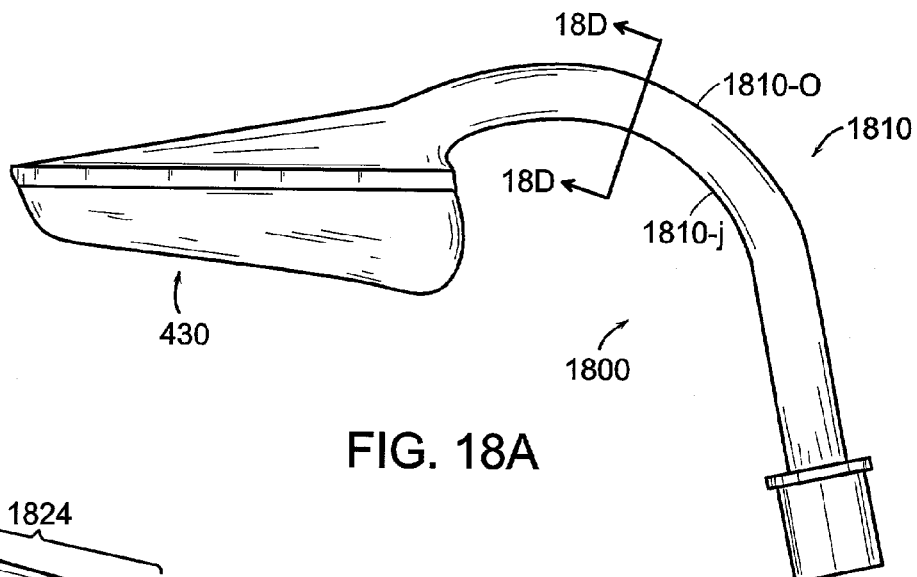
FIG. 18A shows a side view of another laryngeal mask airway device constructed according to the invention.
Figure 18B:
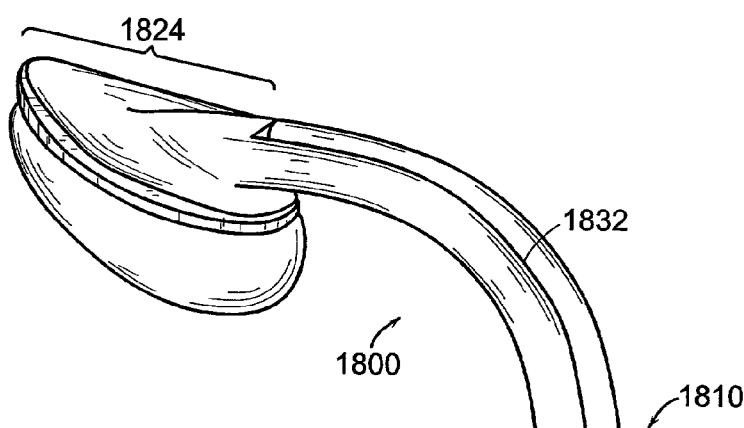
FIGS. 18B and 18C show perspective views of the device shown in FIG. 18A.
Figure 18D:
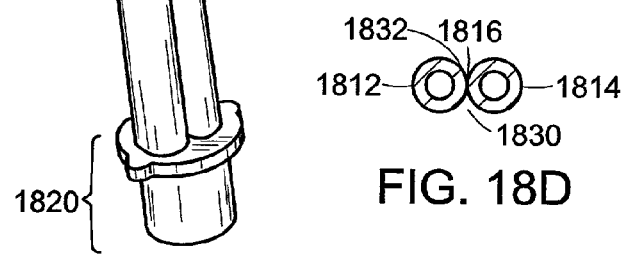
FIG. 18D shows a sectional view of the airway tube taken in the direction of the line 18D—18D as shown in FIG. 18A.
Figure 18C:
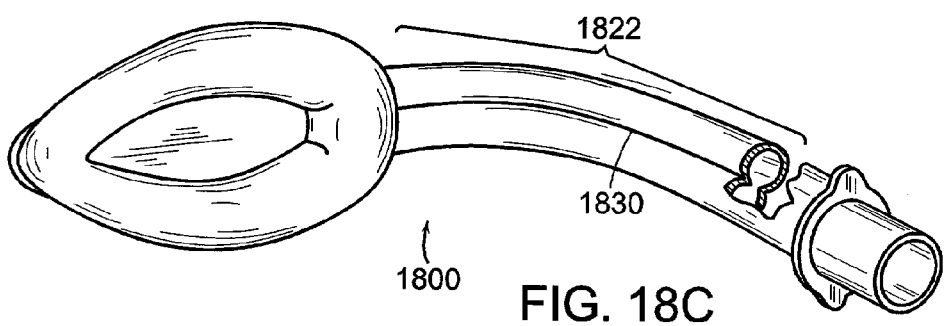

FIG. 18A shows a side view of another embodiment of a laryngeal mask airway device 1800 constructed according to the invention. FIGS. 18B and 18C show two perspective views of device 1800. As shown, device 1800 is very similar to device 400. Both device 1800 and device 400 include identical mask portions 430. Also, the backplate of both devices 1800 and 400 are very similar. The principal difference between the two devices is in the airway tube.

The airway tube 1810 of device 1800 is a double barreled tube. FIG. 18D shows a sectional view of airway tube 1810 taken in the direction indicated by line 18D—18D as shown in FIG. 18A. Airway tube 1810 includes a left tube 1812 and a right tube 1814. The tubes are fixed, bonded, or extruded together at a central joint 1816 that extends from the proximal ends to the distal ends of the two tubes. Airway tube 1810 also defines an inner side 1810-*i* and an outer side 1810-*o*.

As with airway tube 410, tube 1810 has an overall oblong or flattened cross section. Accordingly, tube 1810 (like tube 410), fits relatively well within the patient's anatomical airway and minimizes the intra-dental gap required to accommodate the tube. Also as with tube 410, airway tube 1810 includes a proximal portion 1820, a central portion 1822, and a backplate portion 1824. Backplate portion 1824 is almost identical to backplate portion 419. The only principal difference between the two backplate portions is how they couple to their respective central portions of the airway tube.

As shown in FIG. 18D, the junction of the two cylindrical tubes 1812 and 1814 at the joint 1816 forms two grooves, or recesses, 1830, 1832 in the airway tube. The groove 1830 extends along the inner side 1810-*i* of the airway tube and the groove 1832 extends along the outer side 1810-*o* of the tube. One advantage of tube 1810 is that the groove 1830 can serve as a guide for guiding subsequently inserted tubes, such as for example an endotracheal tube. That is, after device 1800 has been positioned in the fully inserted configuration, the groove 1830 can be used to guide a subsequently inserted device. FIG. 19A shows a perspective view of an endotracheal tube being guided by groove 1830 as the endotracheal tube is inserted into the patient's body (not shown).

Embodiments of device 1800 that are used to guide a subsequently inserted endotracheal tube (or some other kind of tube), preferably define a "gap", or aperture, between the mask portion and the backplate portion at the proximal end of the mask portion. When the distal tip of the endotracheal tube reaches the mask portion's proximal end, continued insertion of the endotracheal tube will push the endotracheal tube's distal end through the gap between the mask portion and the backplate of the device and enable the endotracheal tube's distal end to proceed through the aperture 442 of the mask portion and into the patient's trachea.

Figure 19B:
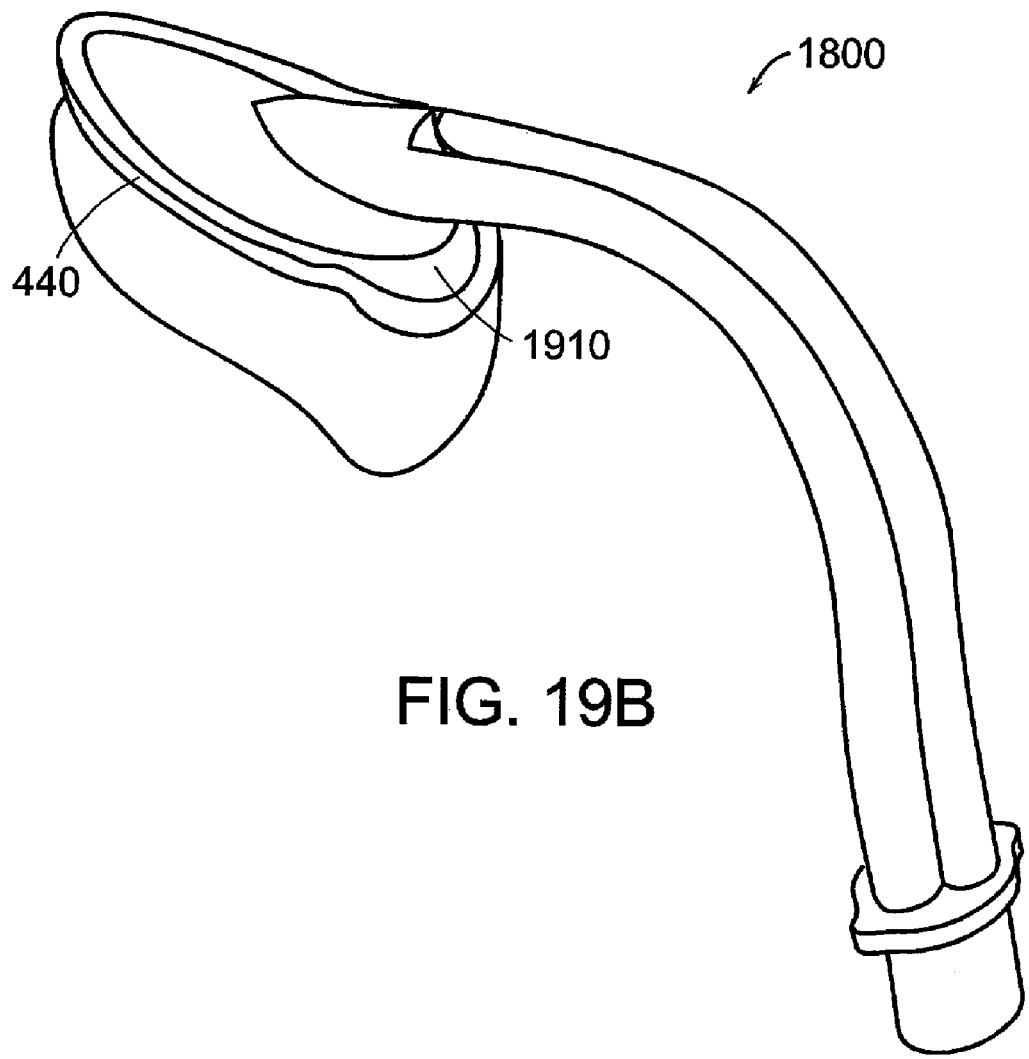
FIG. 19B shows an alternative embodiment of the device shown in FIGS. 18A–18C constructed according to the invention in which the proximal end of the plate is not fixed to the proximal end of the backplate portion of the airway tube.
Figure 19A:
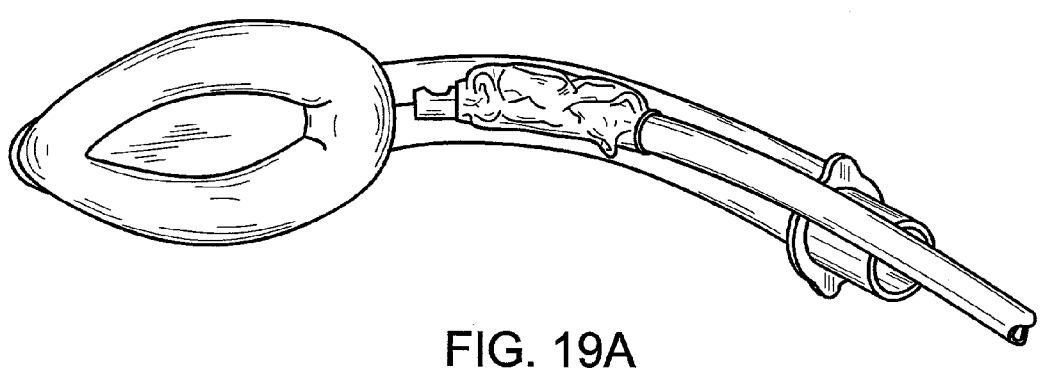
FIG. 19A illustrates how the airway tube of the device shown in FIGS. 18A–18D can be used to guide a subsequently inserted endotracheal tube.

FIG. 19B shows an embodiment of device 1800 that defines such a gap 1910. Both device 400 and device 1800 are constructed by attaching or bonding the outer perimeter of the laryngeal side of the backplate portion of the airway tube to the pharyngeal side of the plate 440 of the mask portion 430. In the case of device 400, the entire outer perimeter of the backplate portion is so attached to the plate 440. However, in the case of device 1800, one portion of the outer perimeter of the backplate (at the backplate's proximal end) is not bonded to the plate 440 and the rest of the outer perimeter of the backplate is bonded to the plate 440. Since the proximal ends of the backplate and plate 440 are not bonded together, pressure on the plate 440 can push the plate 440 of the mask portion away from the backplate and create the gap 1910. In the absence of downward pressure on the plate 440, the portions of the backplate and plate 440 that are bonded together tend to hold the unbonded portions together as well. The effect is to create a laryngeal mask airway device that has a "flap valve". Under normal conditions, the plate 440 and backplate of device 1800 remain in contact as in the case of device 400. Also, when device 1800 is in the fully inserted configuration, pressure exerted by the patient's pharyngeal and laryngeal walls tends to push the plate 440 and backplate towards one another, or together. However, in device 1800, pressure on the proximal end of the mask portion (generated for example by subsequent insertion of an endotracheal tube that is guided by groove 1830) can push the plate 440 away from the backplate to generate the gap 1910. Subsequently inserted endotracheal tubes can extend through gap 1910 and then through aperture 442 and into the patient's trachea.

Figure 20:
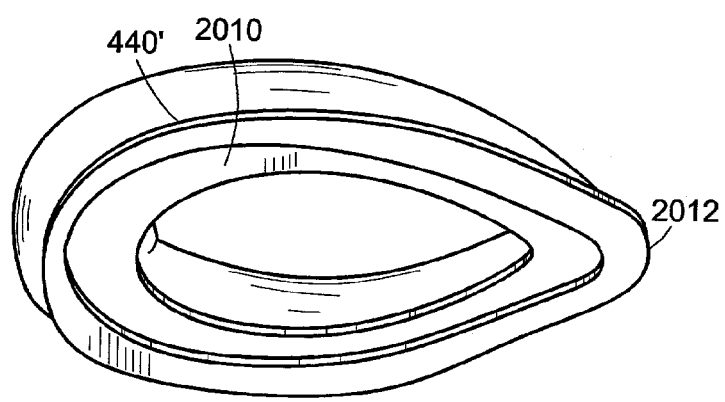
FIG. 20 shows an alternative embodiment of a mask portion constructed according to the invention.

FIG. 20 shows a perspective view of an alternative embodiment of a mask portion 430' that may be used in laryngeal mask airway devices constructed according to the invention. Mask portion 430' is similar to mask portion 430, however, the pharyngeal side of the plate 440' of mask portion 430' is not flat and instead defines a step, or recess, 2010, that extends around the elliptical central aperture of the mask portion. It will be appreciated that the recess 2010 may be used to properly locate the backplate portion of the airway tube when the backplate portion is fixed to the mask portion. Preferably, the laryngeal side of the backplate portion is bonded or fixed to the bottom of the recess 2010. When the backplate portion is fixed to the bottom of recess 2010, a small portion 2012 at the distal end of the plate 440' separates the distal tip of the backplate portion from the distal tip of the laryngeal mask airway device. This may be advantageous because the airway tube is generally harder and stiffer than the mask portion. So, as the laryngeal mask airway device is inserted into a patient, and the device's distal tip contacts anatomical structures within the patient's natural airway, the contact is between the patient and the relatively soft mask portion rather than between the patient and the harder backplate portion. Mask portion 430' thereby advantageously provides a simple mechanism for properly locating the backplate portion when the laryngeal mask airway device is being assembled and also protects the patient from potential traumatic contact with the relatively hard distal tip of the backplate portion as the device is being inserted. It will be appreciated that mask portion 430' may be used in place of mask portion 430 in device 400, device 1800, or any other laryngeal mask airway devices constructed according to the invention.

Figure 10D:
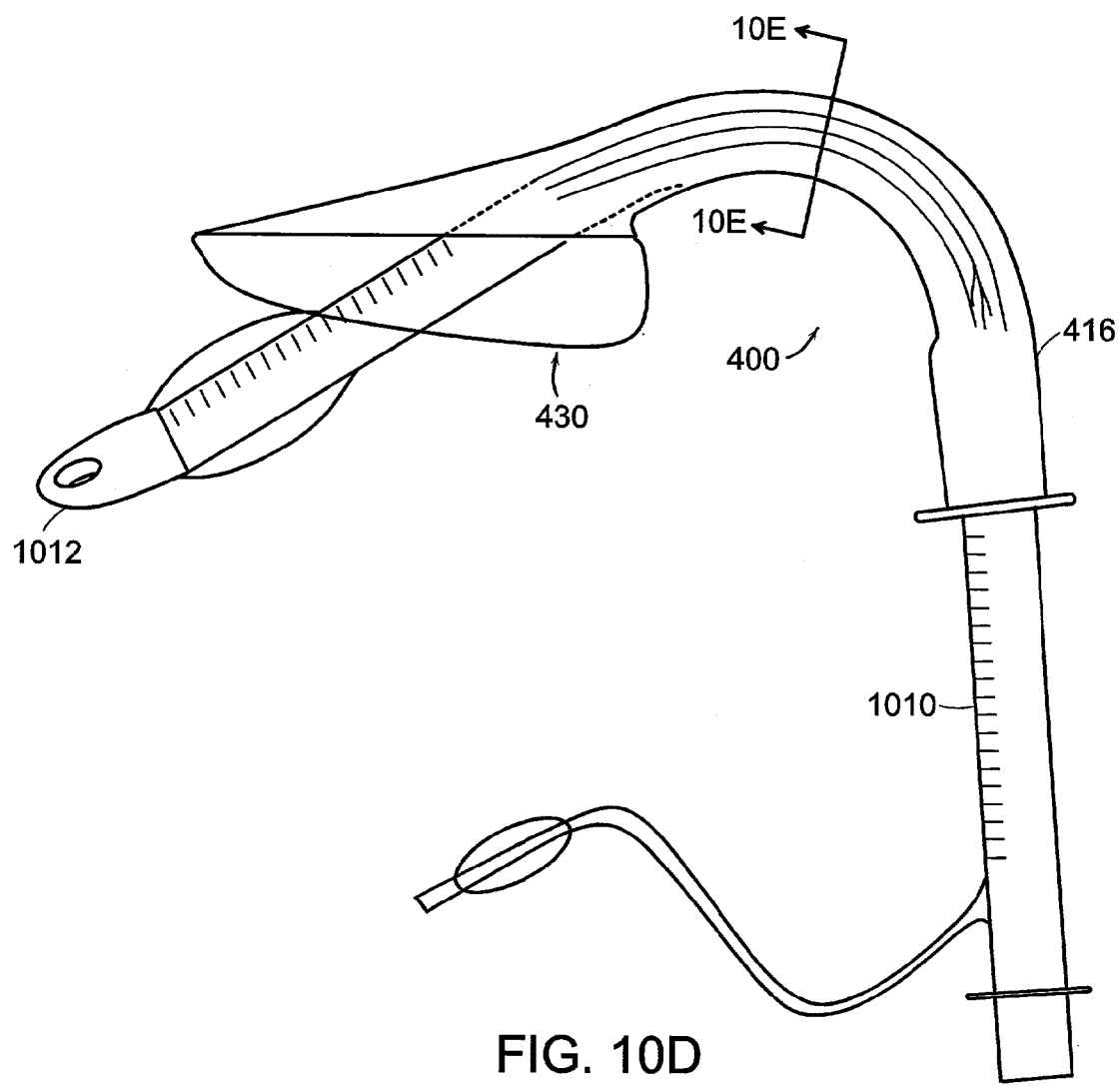
FIG. 10D shows a side view of an embodiment of an intubating laryngeal mask airway device constructed according to the invention, and an endotracheal tube extending through the device.

As discussed above in connection with FIGS. 10B and 10C, the longitudinal folds in the airway tube permit the tube to compress somewhat in a concertina or accordion like fashion. Another advantage of the longitudinal folds is that they can permit the airway tube to expand in response to forces applied to the interior of the tube. This expansion can advantageously permit the airway tube to accommodate a subsequently inserted endotracheal tube and thereby allows device 400 to function as an intubating laryngeal mask airway device. FIG. 10D shows a side view of an embodiment of device 400 into which an endotracheal tube 1010 has been inserted. To reach the configuration illustrated in FIG. 10D, the distal end 1012 of endotracheal tube 1010 was inserted into the proximal end of integral tube and backplate section 416 and advanced through the section 416 until the distal end 1012 emerged through the aperture in the mask portion 430 as shown. As the endotracheal tube 1010 advances through integral tube and backplate section 416, the longitudinal folds in the section 416 allow the section 416 to expand and thereby accommodate the endotracheal tube.

Figure 10E:
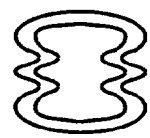
FIG. 10E shows a sectional view of the intubating laryngeal mask airway device taken along line 10E—10E as shown in FIG. 10D.

It will be appreciated that when device 400 is used as an intubating laryngeal mask airway device, it may be desirable to use alternative embodiments of the airway tube 410 or the integral tube and backplate section 416. For example, the integral tube and backplate section 416 shown in FIG. 10D includes two longitudinal folds that extend down the left and right sides of the tube rather than the single fold provided in the section 416 illustrated in FIGS. 10B and 10C. FIG. 10E shows a cross section of the section 416 taken in the direction of line 10E—10E as shown in FIG. 10D. FIG. 10E shows the two longitudinal folds that extend down the left and right sides of the integral tube and backplate section. FIG. 10E shows the integral tube and backplate section in an expanded condition. That is, the longitudinal folds have expanded in a concertina like fashion to accommodate the subsequently inserted endotracheal tube. It will be appreciated that airway tubes constructed according to the invention may be provided with one, two, or more longitudinal folds that extend down the left and right sides of the tube.

In addition to including extra longitudinal folds, it will be appreciated that it may be advantageous for the airway tube, or integral tube and backplate section, of intubating laryngeal mask airway devices constructed according to the invention to include a modified proximal end that is cylindrical or otherwise wide enough to accommodate insertion of an endotracheal tube as shown in FIG. 10D.

Figure 10F:
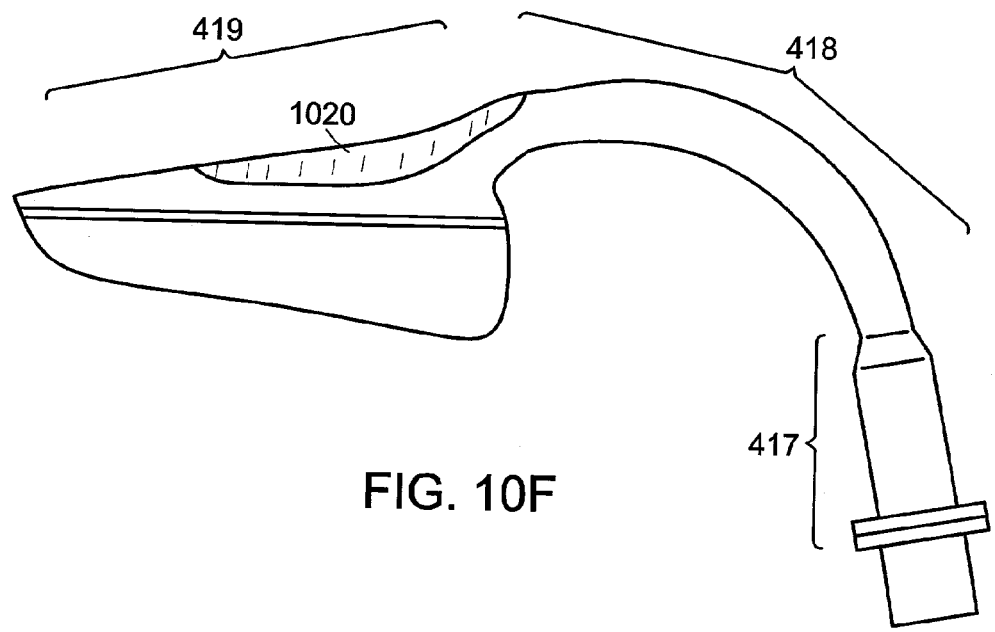
FIG. 10F shows a side view of another embodiment of a laryngeal mask airway device constructed according to the invention.
Figure 10G:
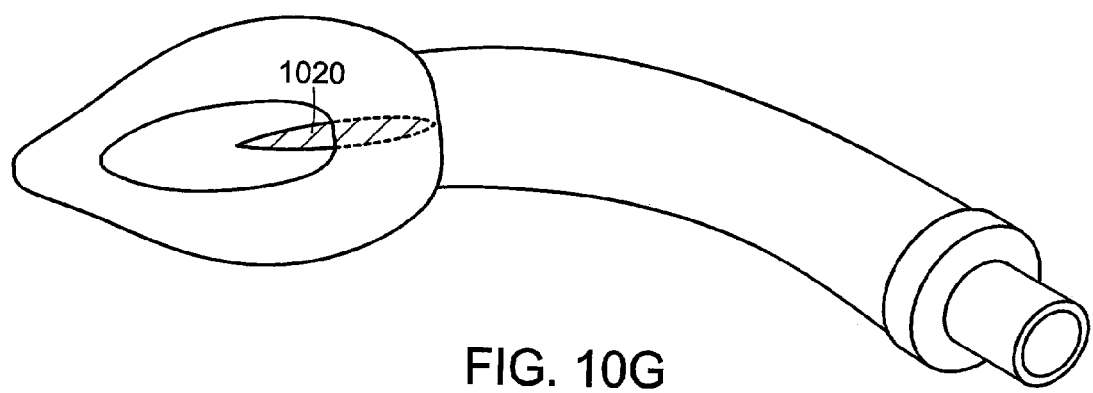
FIG. 10G shows a perspective view of the embodiment shown in FIG. 10F.

FIG. 10F shows a side view of another embodiment of device 400 constructed according to the invention, and FIG. 10G shows a perspective view of the embodiment shown in FIG. 10F. In the illustrated embodiment, the airway tube includes a ridge 1020. Ridge 1020 extends in the proximal-to-distal direction from a point near the middle of the backplate portion 419 to a point in the curved portion 418 that is proximal to a junction of the backplate portion 419 and the curved portion 418. Ridge 1020 also extends from the outer side of the tube 410-o into the interior of the passage defined by the tube. In this embodiment, the walls of the tube near the junction of the curved portion 418 and the backplate portion 419 are also preferably weaker than the walls in other portions of the tube. For example, the tube wall can be made thinner in this region to weaken this portion of the tube.

The embodiment illustrated in FIGS. 10F and 10G facilitates rotating the patient's head while the laryngeal mask airway device is in the fully inserted configuration. For example, the device may be placed in the fully inserted configuration while the patient is resting in the neutral position (i.e., the patient will be lying on their back and the patient's nose will be the part of the patient's head that is furthest from the ground). Once the laryngeal mask airway device is so located, it may be desirable to rotate the patient's head. For example, if the patient's ear is being operated on, it may be desirable to rotate the patient's head approximately ninety degrees so that instead of the patient's nose, the patient's ear is now the part of the patient's head that is furthest from the ground. It will be appreciated that this exposes the ear and makes it easier to operate on the ear. Ideally, rotating the patient's head in this manner while the laryngeal mask airway device is located in the fully inserted configuration (1) will not disturb the seal between the inflated cuff and the tissues surrounding the patient's glottic opening and (2) will not cause a collapse of the internal passage provided by the airway tube. Weakening the walls of the airway tube near the junction of the backplate portion 419 and the curved portion 418 allows the distal part of the laryngeal mask airway device (i.e., the mask portion and the backplate portion) to rotate with respect to the remainder of the airway tube without placing undue force on the inflated cuff, and this tends to preserve the seal between the cuff and the tissues surrounding the glottic opening when the patient's head is so rotated. Ridge 1020 tends to prevent the internal passage provided by the airway tube from collapsing when the patient's head is so rotated and the airway tube is correspondingly twisted.

Figure 21:
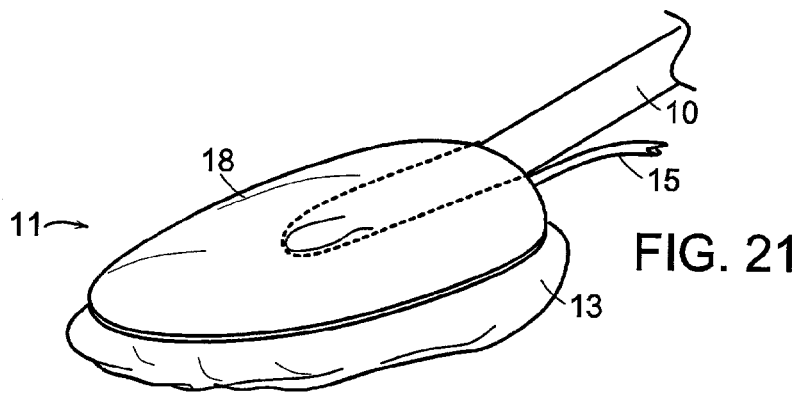
FIG. 21 is a simplified view in perspective for another laryngeal mask airway device device according to the invention, as seen in three-quarter perspective and viewing the posterior side of mask structure, in inflated condition at the distal end of an airway tube.
Figure 22:
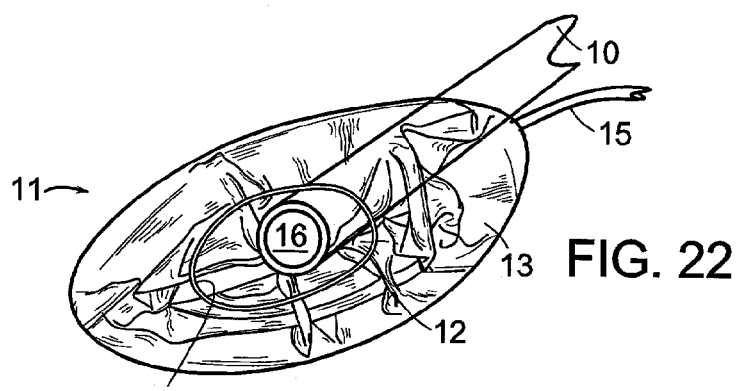
FIG. 22 is a similar view of the structure of FIG. 21, as seen from the anterior (or trachea-facing) side of the device of FIG. 21, but in the evacuated state wherein thin-film material of the inflation is collapsed and matted against skeletal base structure of the device.

FIGS. 21 and 22 show another embodiment of a laryngeal mask airway device constructed according to the invention. In this embodiment, an air inlet tube 10 will be understood to provide air (or other gas) service to a patient's lungs via mask structure 11 and the patient's trachea. As best seen in FIG. 22, base structure of the mask 11 comprises a relatively stiffly pliant skeletal base 12 of generally elliptical configuration, a portion of this base being viewable directly through a draftsman's break through a collapsed thin-film inflatable envelope 13, which will be understood to be inflatable by external supply of inflation air via a flexible inflation line 15; line 15 will be understood to include a conventional two-way check valve (not shown) for purposes of holding an inflated condition of the envelope 13 (as in FIG. 21) or for holding a deflated condition of the envelope (as in FIG. 22). The envelope 13 is merely an inflatable portion of a single-part, integrally formed, total enclosure served by the inflation/deflation line 15, being the product of a so-called rotational-molding process, wherein a single plastic material in liquid state is caused to progressively build a thin layer or film of cured plastic material against and throughout the internal surface area of a given annular mould cavity, the gravitationally drained remained of the liquid-phase plastic being allowed to cure in situ as the relatively stiff skeletal annular member of the laryngeal mask airway device, at the bottom of the mould. The cured product of such moulding not only provides the indicated skeletal-base function but also, between the inner and outer peripheries of the skeletal annulus provides the additional function of completing, as a skeletal annulus, the inflatable and peripherally yieldable enclosure of envelope provided by the moulded film. For the case of the described integrally formed component (12/13) when formed of suitable plastic such as polyvinylchloride, the thin film at 13 is typically of thickness in the order of 0.1 to 0.3 mm, while the skeletal base 12 may be typically 10 to 20 times the moulded thickness of the film 13. Such film will be understood to collapse and flatter or mat itself at random in response to deflation action via line 15. It is to be understood that while it is possible to form the skeletal base 12 as flat and of relatively uniform thickness, it is also possible to use the described moulding process to develop a skeletal-base thickness which varies as a function of longitudinal progression, as from a relatively thick proximal location (e.g., 2–3 mm thick) to a much reduced distal-end thickness (e.g., 1-mm), thereby according a desired distal-end bendability which can usefully serve the process of installing the laryngeal mask airway device in the patient. Such a proximal-to-distal thickness variation is later indicated in FIG. 25 (at 12') as a feature of the device of FIGS. 23 and 24.

To complete a description of the laryngeal mask airway device of FIGS. 21 and 22, the airway tube 10 is shown to be supported on and by its overlap with posterior surface of the proximal region of the annulus of skeletal base 12, the distally open end 16 of the airway tube having preferably an angularly truncated configuration, which is open within the generally elliptical lumen 17 of the skeletal base 12. Finally, closure of the posterior side of the mask structure is effected by a tent-like roof 18 of flexible plastic sheet material, wherein the lapped distal portion of the airway tube is analogous to a ridge pole, so that the tent-like roof sheeting slopes away from its longitudinally central support by the distal end of the airway tube, to its peripherally sealed engagement to the rim of the skeletal base, as seen in FIG. 21, it being understood that sheeting 18 is also suitably draped and sealed at its proximal-end closure around the airway tube 10.

Figure 23:
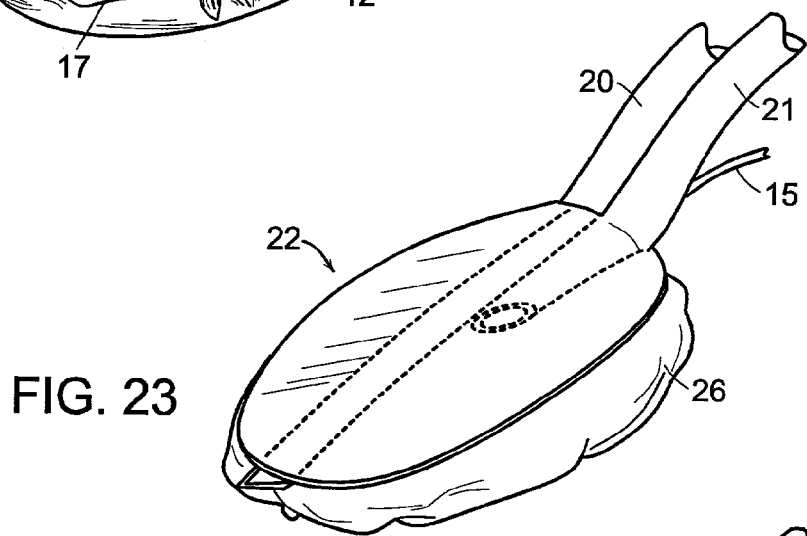
FIG. 23 is a view similar to FIG. 21, for a laryngeal mask airway device having a gastric-drainage feature of the invention.
Figure 24:
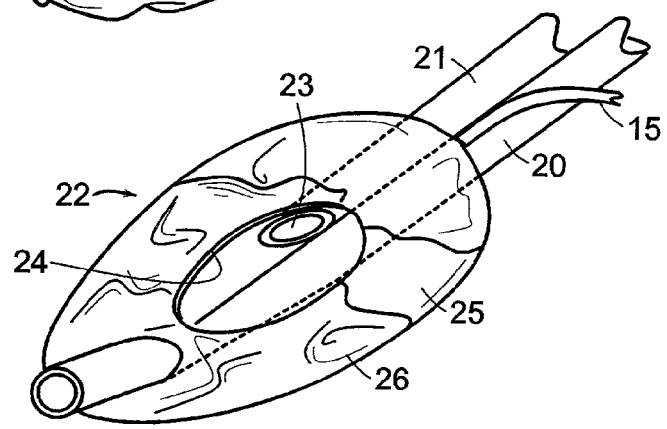
FIG. 24 is a view similar to FIG. 22, for the device of FIG. 23.

FIGS. 23 and 24 are recognizable for their resemblance to FIGS. 21 and 22, except for the additional provision of a gastric-drainage tube 20, in side-by-side bonded relation to an airway tube 21, which may in all respects be as described for airway tube 10 of FIGS. 21 and 22, except for the fact that tubes 20/21 are symmetrically and oppositely offset from the longitudinal sagittal plane of the generally elliptical configuration of mask structure 22. This symmetrical relation is seen to continue until the distally open end 23 of the airway tube 21 is positioned to vent over the lumen 24 of the generally elliptical annular skeletal base 25 of the mask structure. As with the laryngeal mask airway device of FIGS. 21 and 22, the base skeletal member 25 may be a product of a rotational moulding operation wherein a thin-film inflatable/deflatable annular envelope 26 is integrally formed therewith, with provision for selective inflation/deflation action via a flexible line 15, as also in FIGS. 21 and 22.

Figure 25:
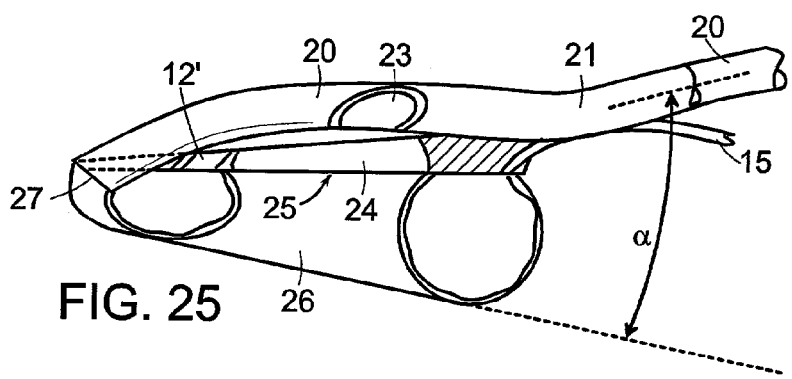
FIG. 25 is a sectional view taken generally in the longitudinal sagittal plane of the device of FIG. 23, certain parts being omitted, for clarity.
Figure 26:
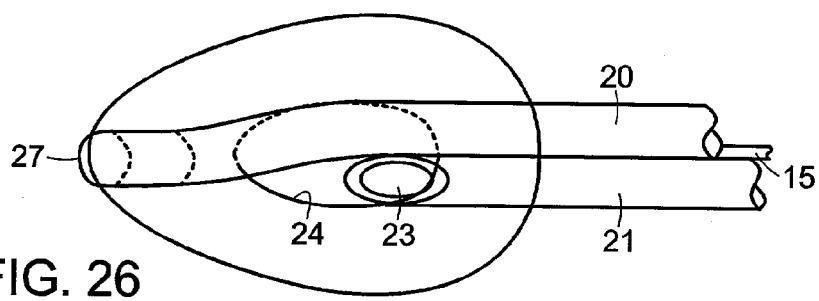
FIG. 26 is a plan view of the posterior side of the device of FIG. 23, certain parts being omitted for clarity.
Figure 27:
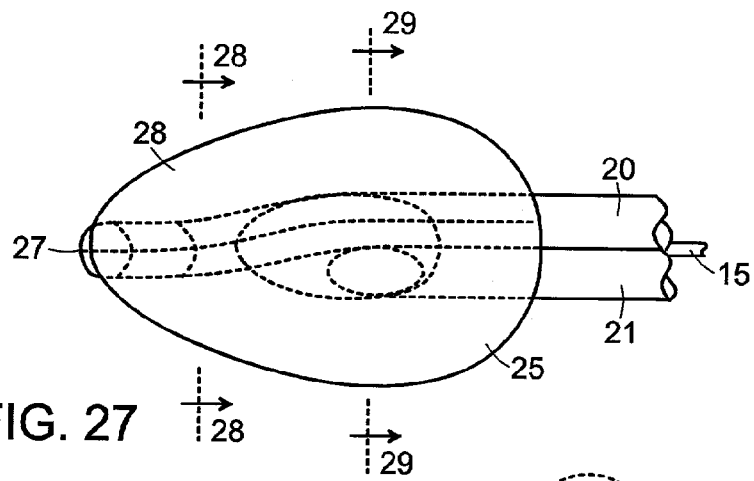
FIG. 27 is a plan view as in FIG. 26 but with added showing, to include structure omitted from FIG. 26.

For gastric-drainage purposes, and as better seen in FIGS. 25 to 29, the drainage tube 20 is seen in FIG. 26 to undergo a mild zig-zag course change, from lateral offset adjacency to airway tube 21 to its distal-end alignment of symmetry with respect to the sagittal plane of the mask. Within the distal half of the skeletal base 25, and the distal end of drainage tube 20 passes through the base 25 and projects its angularly truncated open end 27 slightly beyond the distal end of base 25.

As previously noted, the longitudinal progression of reducing thickness of skeletal base 25 in the distal direction enables a more pliant action to be inherently imparted to the distal half of the mask. FIG. 25 also illustrates that the inflated sectional area of the inflated thin-film envelope 26 is similarly and progressively decreased in the distal direction, so that tubes 20, 21 may be oriented at proximal departure from the mask to incorporate a preferred angle $\alpha$ in the range 20° to 30°, at commencement of their proximal course over the tongue, for air (gas) and gastric servicing connections (not shown), as necessary outside the patient's mouth.

Figure 28:
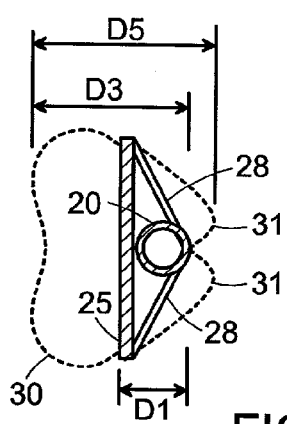
FIG. 28 is a sectional view, taken at 28—28 in FIG. 27.
Figure 29:
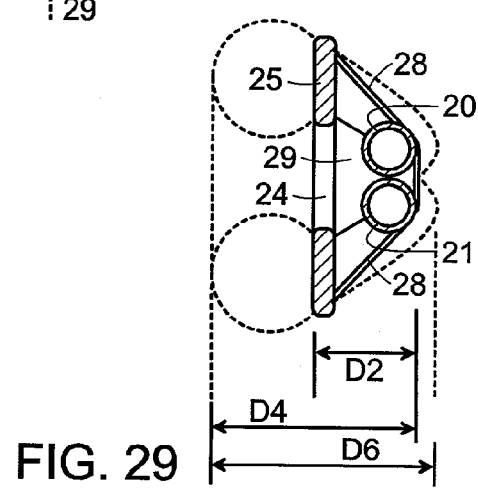
FIG. 29 is a similar sectional view, but taken at 29—29 in FIG. 27.

As with the laryngeal mask airway device of FIGS. 21 and 22, the structure of FIGS. 23 and 24 may be completed with a tent-like closure 28 of the posterior side of the mask. Again, such closure is realized by pliant sheet material which in FIG. 28 is seen to derive "ridge-pole" support from tube 20, centered on the distal-half of skeletal base 25. In FIG. 29, the section shows the tent closure 28 to be supported over the adjacent tubes 20, 21 at passage over the lumen 24 of the mask, with the skirt of tent sheeting peripherally secured to skeletal base 25, it being again understood that at its proximal end, the tent sheeting is also conformed and sealed to both tubes 20, 21 to complete closure of the posterior side of the mask.

In FIG. 28, a bulging profile in phantom outline 30 on the anterior side of the mask will be understood to suggest film-envelope inflation away from the anterior surface of skeletal base 25, and a further inflation profile 31 in phantom outline on the posterior surface of the mask will be understood to suggest an inflatable cuff 31 over the periphery of base 25, to provide cushioned reference of the mask to the back wall of the patient's pharynx. As shown, the back-cushion material is shown for its further connection to tent 28 along the sagittal-plane intercept with tent 28.

Figure 30:
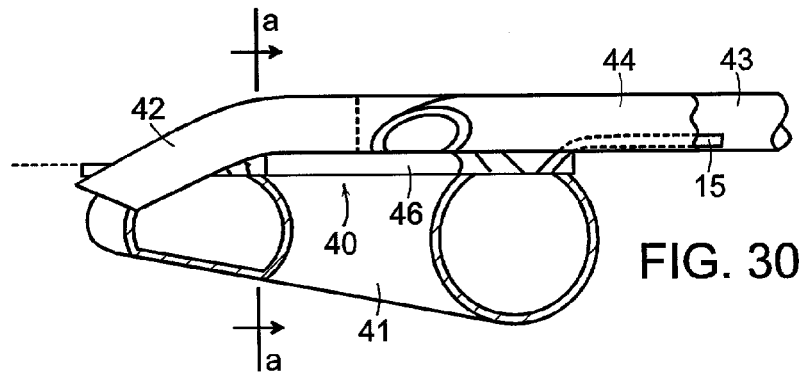
FIG. 30 is a longitudinal section as in FIG. 25, for a modified embodiment of the invention.
Figure 31:
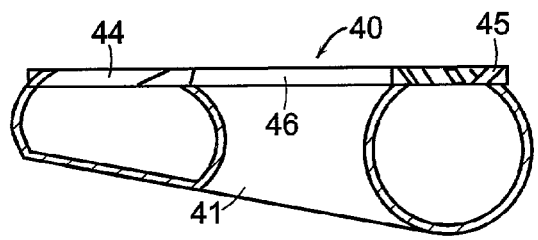
FIG. 31 is another and similar longitudinal section, taken only to show an integrally formed feature of the invention, being a major component of the embodiment of FIG. 30.
Figure 32:
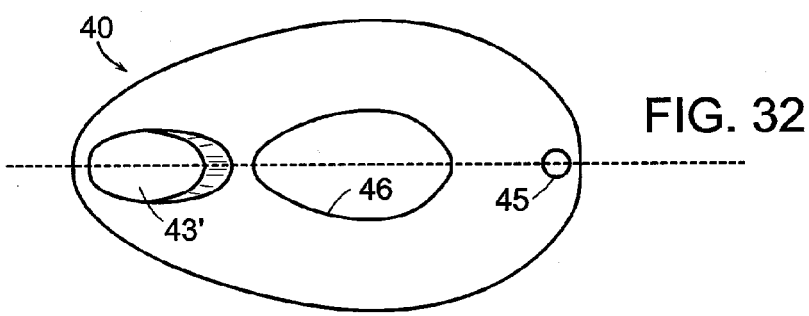
FIG. 32 is a plan view of the posterior side of the component of FIG. 31.

It is desired that for ease of installation of the mask in a patient, that the deflated condition should offer a minimum thickness dimension. this will be clear from FIGS. 28 and 29 where the respective minimum dimensions D1, D2 are to be compared with maximum available inflation dimensions D3, D4 without the back cushion 31, and D5, D6 with the back cushion 31. In the embodiment of FIGS. 30 to 32, the simplest difference to note is that the skeletal base 40 is flat and its integrally formed thin-film inflatable envelope portion 41 is otherwise as described for the inflatable film 26 of FIG. 25. Also, the distal portion 42 of the drainage tube 43 is locally bent for straight but inclined passage through a similarly inclined orienting opening 44 in the distal-end region of base 40. At remaining overlap with the proximal-end region of base 40, the drainage tube 43 is laterally offset to the extent that it can symmetrically pair with airway tube 44, and both tubes 43, 44 can be bonded to the supporting flat posterior surface of base 40. Tentlike sheet material described for closure of the posterior side of the mask can be as described for FIGS. 25 to 29, it being noted that at section a-a of FIG. 30, the local section bears an almost identically similar appearance to that depicted in FIG. 28 for the mask of FIG. 27.

According to one technique of manufacture of the unitary base 40 with integrally moulded thin-film envelope portion 41, this single component is depicted in the longitudinal section of FIG. 21 and in the plan view of FIG. 22, it being understood that such passages as at 43' (for drainage-tube passage as at 43', for drainage-tube orientation), at 45 (for inflation-air access), and at 46 (for lumen definition) are the product of known core-pin and other mould-feature defining structures of the mould as an entirety. The preassembly of tubes 43,44 in side-by-side adjacency, together with the pre-bent and truncated open distal end of drainage tube 43 are later assembled for adhesively or otherwise sealed passage of the distal end of the drainage tube 43 and for film-pierced and peripherally sealed passage of the truncated distal end of tube 43 into the relationship depicted in FIG. 30.

Figure 31A:
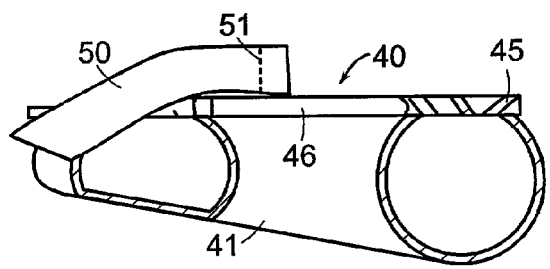
FIG. 31A is a view similar to FIG. 31 to show a modification.

In an alternative mode of structural assembly, depicted in FIG. 31A, a preformed and suitably bent distal-end fitting 50, for later assembly to the remainder of the drainage tube (not shown) is an insert part which in the process of rotation-moulding becomes the FIG. 31A part to be later assembled to mask parts that become a laryngeal mask airway device with the gastric-drainage feature. To this end, the preassembled drainage and airway tubes 43, 44 will be understood to terminate over the lumen 46 and that the distally projecting end of the drainage-tube portion (43) of this tube (43, 44) preassembly may be suitably fitted to the open proximal end of fitting 50, to establish continuity of the full drainage-tube function. Such continuity may be provided by known techniques of telescoping fit, as to the extent denoted by dotted line 51 in FIG. 31A, or by a short sleeve of heat-shrink plastic material (not shown) which laps the abutting ends of equal diameter tubular ends, namely the proximal end of fitting 50 to the distal end of the two-tube preassembly (43, 44).

Figure 33:
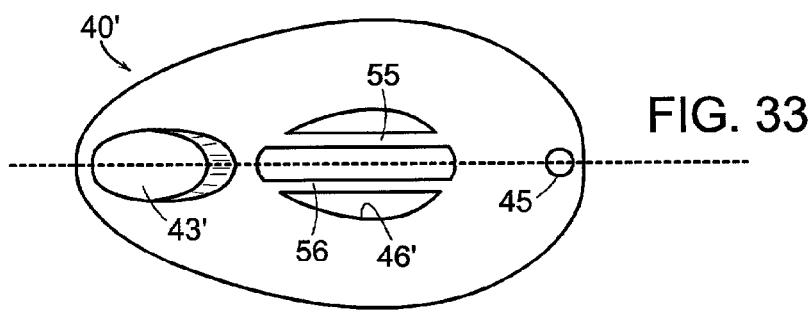
FIG. 33 is a view of a slightly modified version of the component of FIG. 31.

The plan view of skeletal base 40' of FIG. 33 will be recognized as identical to that of FIG. 32, except that two spaced elongate parallel bars 55, 56 Symmetrically straddle the longitudinal sagittal plane of the mask (not shown) into which this component can be integrated. The purpose served by bars 55, 56 is to provide a measure of support for the drainage tube 43 as it passes over the lumen and as it alters course for distal-end symmetrical orientation with respect to the sagittal plane.

Figure 34A:
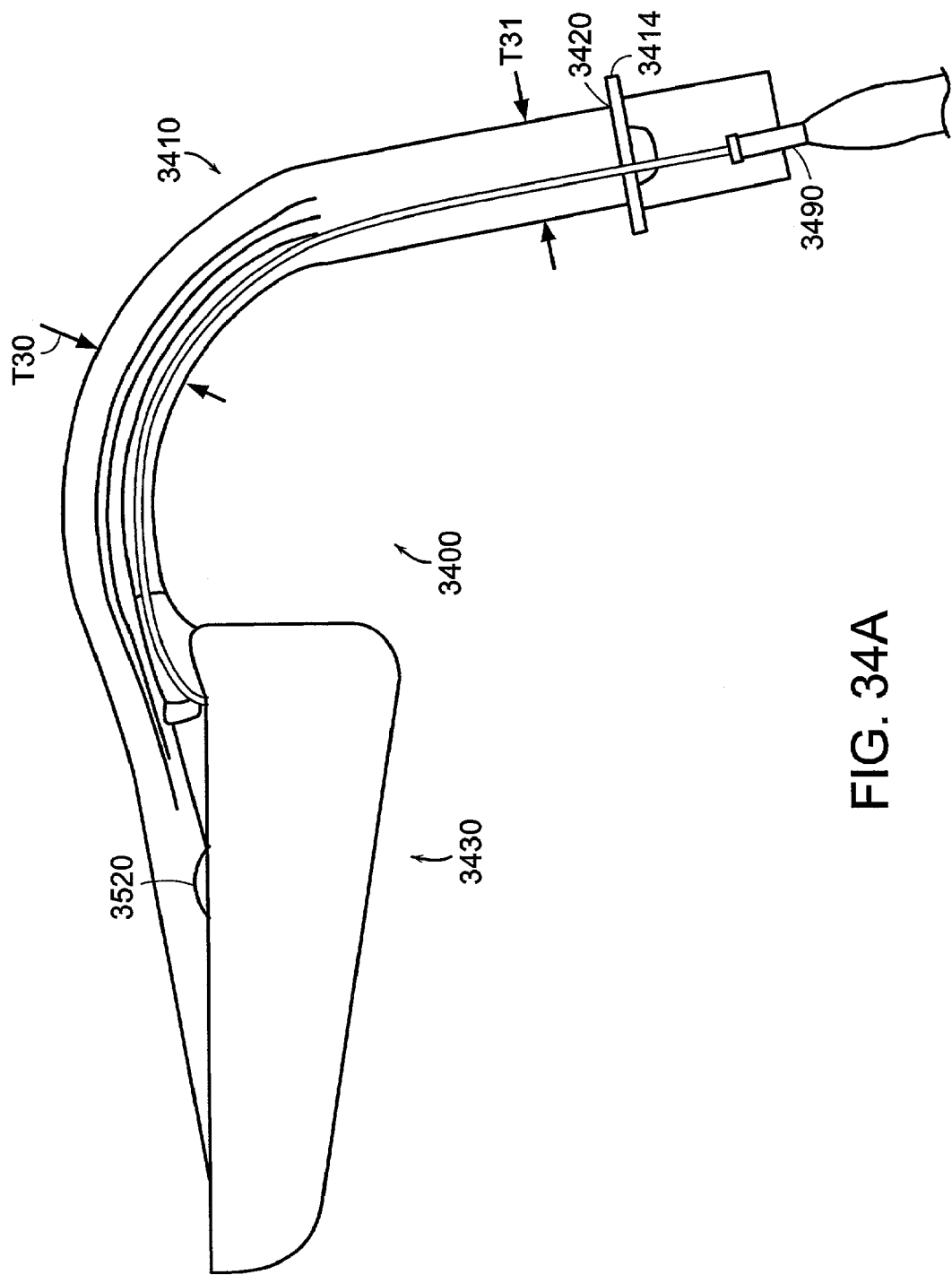
FIG. 34A shows a side view of another laryngeal mask airway device constructed according to the invention.
Figure 34B:
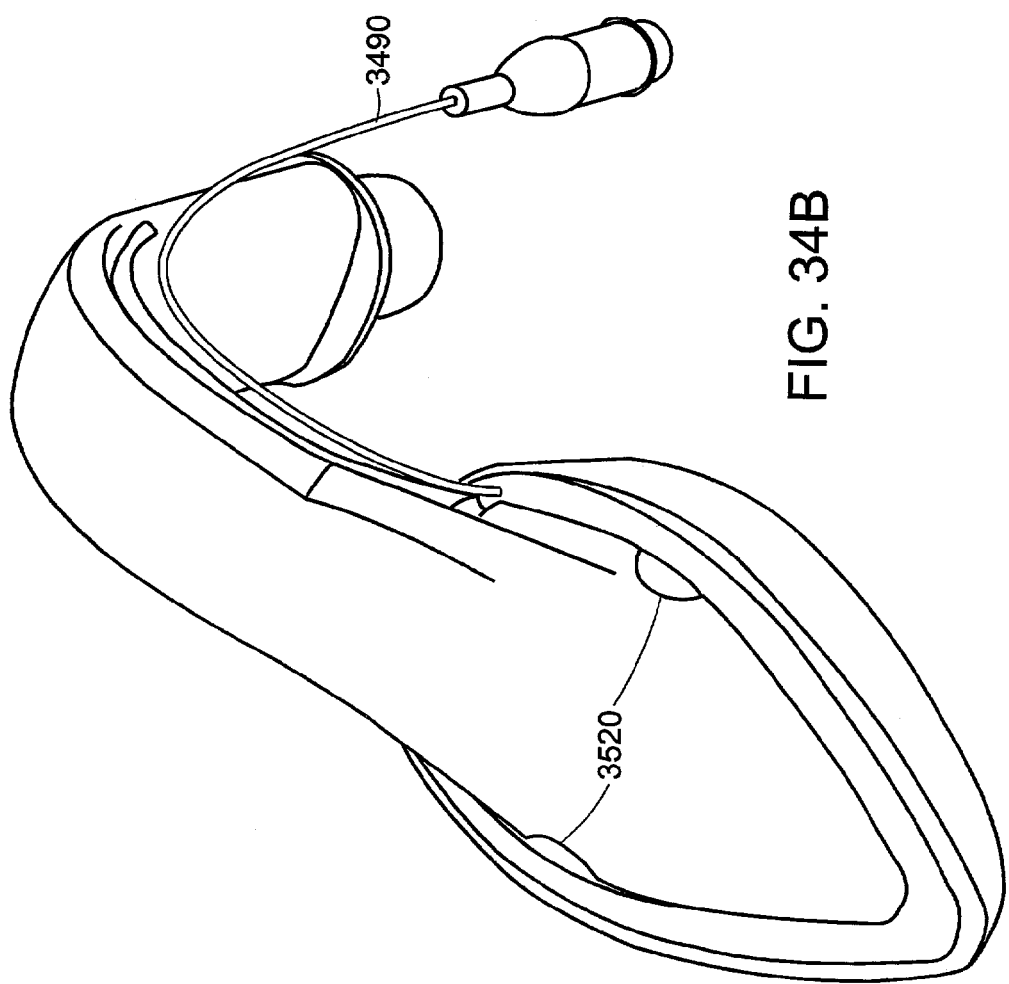
FIGS. 34B and 35C show perspective views of the device shown in FIG. 34A.
Figure 34C:
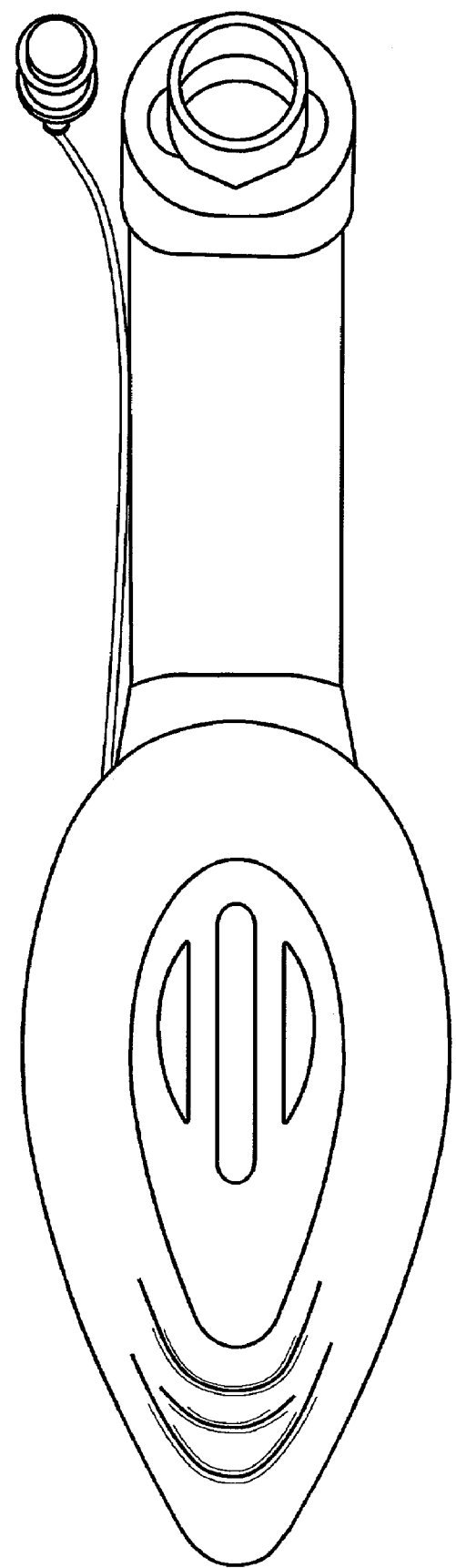
FIG. 34D shows a side view of the device shown in FIG. 34A during construction of the device.

FIG. 34A shows a side view of another embodiment of a laryngeal mask airway device 3400 constructed according to the invention. FIGS. 34B and 34C show perspective views of device 3400. Device 3400 is similar to the above-discussed device 400 (shown for example in FIGS. 4A–4C). Device 3400 includes an airway tube 3410, a mask portion 3430, and an inflation tube 3490. Reference characters for describing components of device 3400 have been generally selected to correspond to those used above to describe device 400 (e.g., the mask portion in device 3400 has been designated 3430 whereas the mask portion of device 400, shown for example in FIG. 4A, has been designated 430).

Figure 35A:
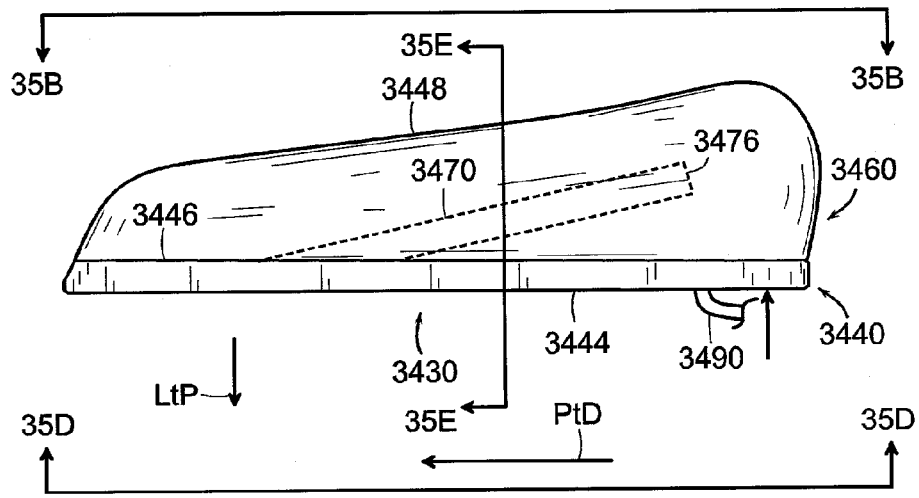
FIG. 35A shows a side view of the mask portion, when inflated, of the device shown in FIG. 34A.
Figure 35B:
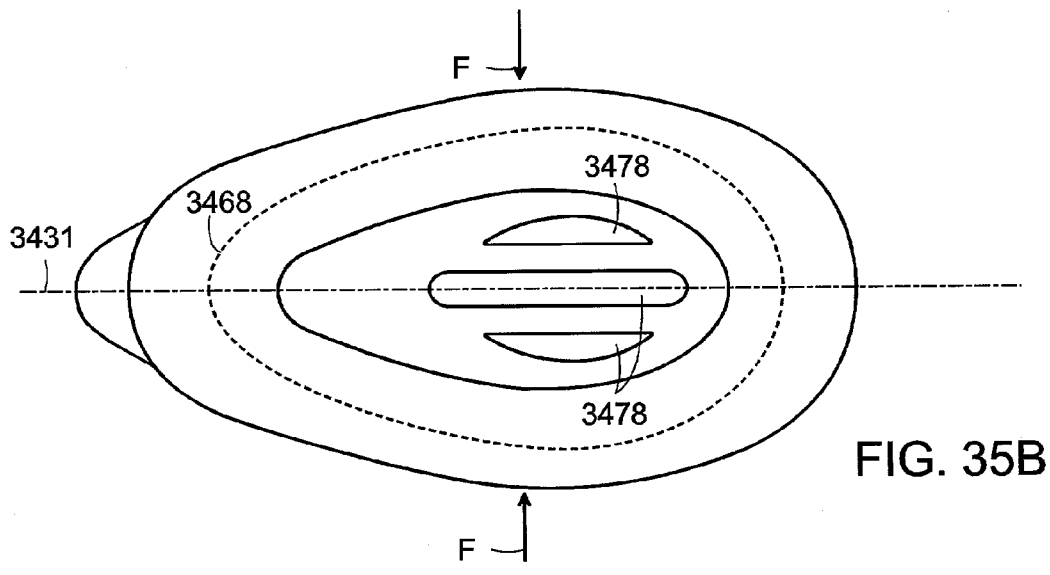
FIG. 35B shows a view of the anterior side of the mask portion shown in FIG. 35A taken in the direction of the line 35B—35B as shown in FIG. 35A.
Figure 35C:
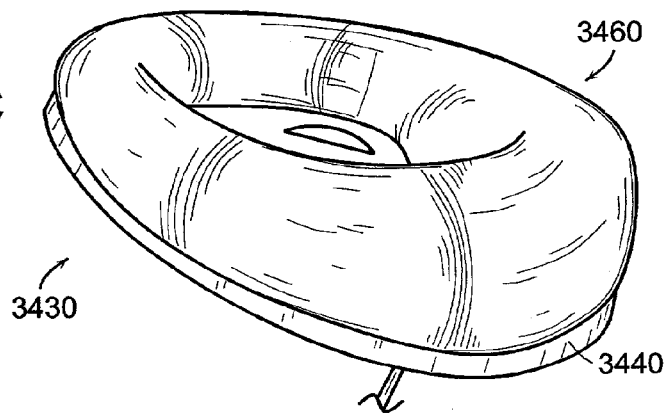
Figure 35D:
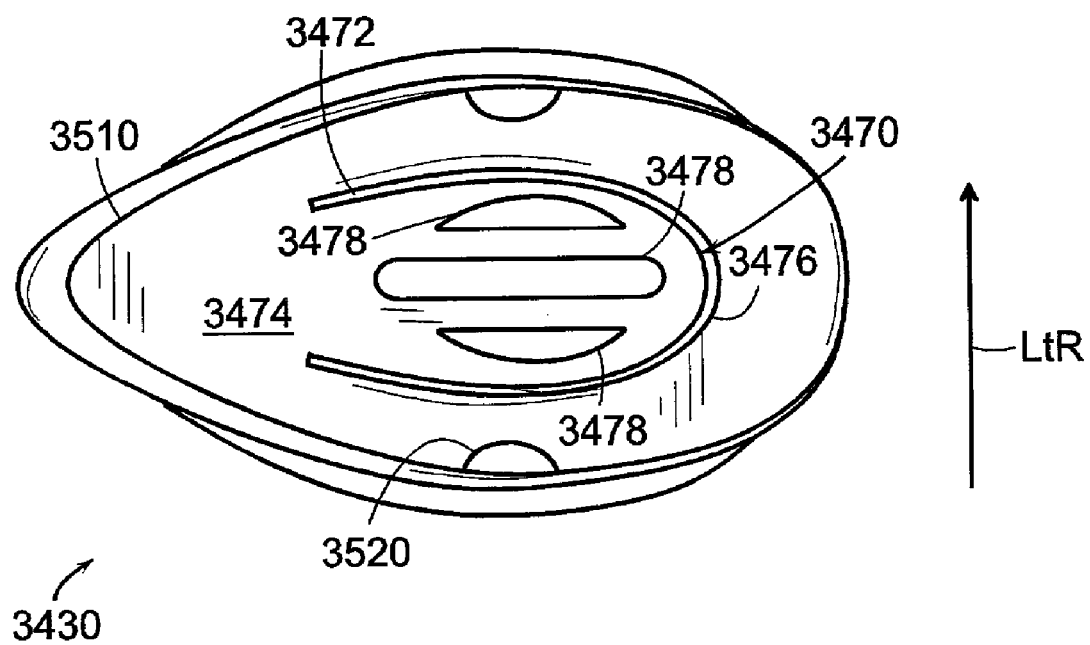
FIG. 35D shows a view of the posterior side of the mask portion shown in FIG. 35A taken in the direction of line 35D—35D as shown in FIG. 35A.
Figure 35E:
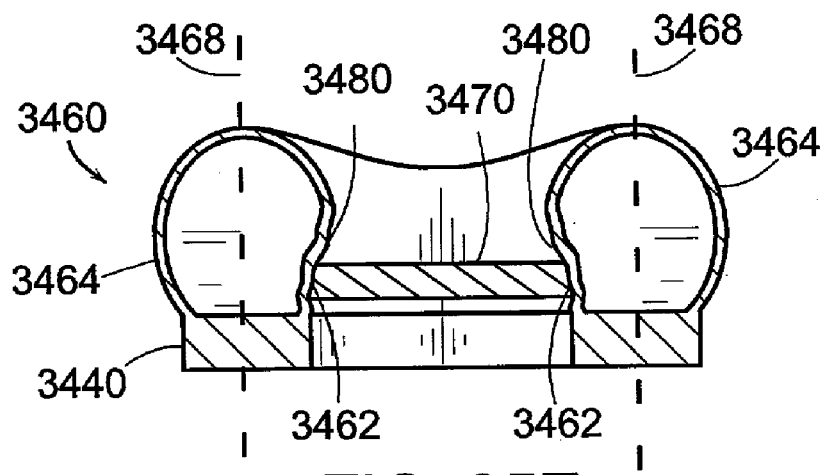
FIG. 35E shows a sectional view of the mask portion shown in FIG. 35A taken in the direction of the line 35E—35E as shown in FIG. 35A.

FIG. 35A shows a side view of mask portion 3430 when the cuff is inflated. FIG. 35B shows a view of the anterior side of mask portion 3430 taken in the direction of line 35B—35B as shown in FIG. 35A. FIG. 35C shows a perspective view of the anterior side of mask portion 3430. FIG. 35D shows a view of the posterior side of mask portion 3430 taken in the direction of line 35D—35D as shown in FIG. 35A. FIG. 35E shows a sectional view of mask portion 3430 taken in the direction of line 35E—35E as shown in FIG. 35A.

As with mask portion 430 (shown, for example, in FIG. 5A), mask portion 3430 includes a plate 3440, an inflatable cuff 3460, and an inflation line 3490. However, as shown best in FIGS. 35A, 35D, and 35E, mask portion 3430 also includes a support 3470. As will be discussed in greater detail below, support 3470 advantageously (1) increases the structural integrity of mask portion 3430 without detrimentally affecting the ease of insertion of device 3400 and (2) prevents the epiglottis from obstructing the airway provided by device 3400.

One method of forming mask portion 3430 so that it includes support 3470 will now be discussed. As discussed above, mask portion 430 (shown, for example, in FIG. 5D) is preferably constructed using a rotational molding technique, and mask portion 430 is formed so that the plate 440 defines a central aperture 442. Mask portion 3430 is also preferably formed using the same rotational molding technique described above in connection with mask portion 430, however, the rotational molds may be altered so that plate 3440 is solid and does not define a central aperture. With reference to FIG. 35D, after the mask portion 3430 has cured and has been removed from the rotational mold, support 3470 may be defined by cutting a horseshoe shaped notch 3472 into plate 3440. Apertures 3478 are also provided in support 3470. At its distal end 3474, support 3470 is contiguous with, and an integral part of, plate 3440. However, the horseshoe shaped notch 3472 permits the proximal end 3476 of support 3470, as well as all portions of support 3470 that are detached from plate 3470 by notch 3472, to flap up and down with respect to the rest of plate 3440. Once horseshoe shaped notch 3472 has been cut in plate 3440, the cuff 3460 is preferably inflated and then the proximal end 3476 of support 3470 is pushed into the bowl shaped aperture defined by the inflated cuff 3460. Once the support 3470 has been located within the aperture defined by the inflated cuff as shown in FIGS. 35A and 35E, the outer periphery 3480 of support 3470 is preferably bonded (e.g., by ultrasonic welding or use of adhesives), to the inner periphery, or inner wall, 3462 of cuff 3460.

As shown in FIG. 35E, the inflated cuff 3460 may be thought of as defining an inner wall 3462 and an outer wall 3464. The inner wall 3462 and outer wall 3464 are separated by an elliptical cylinder indicated in FIG. 35E by dashed lines 3468. This elliptical cylinder is also indicated by the dashed line 3468 in FIG. 35B. It will be appreciated that while cylinders are characterized by a circular cross section, the elliptical cylinder indicated by dashed lines 3468 is characterized by a generally elliptical, or oblong, cross section. Returning to FIG. 35E, it will be appreciated that the central opening defined by the generally toroidal inflated cuff 3460 is bounded by the inner wall 3462 of the cuff 3460. Support 3470 is preferably bonded to the cuff 3460 at some points along the cuff's inner wall 3462.

Since the support 3470 is bonded to the cuff 3460, deflation of the cuff 3460 causes the cuff 3460 to draw the support 3470 in the laryngeal-to-pharyngeal direction so that the support 3470 is nearly parallel to plate 3440. In practice, when cuff 3460 is fully deflated, support 3470 tends to be slightly offset in the pharyngeal-to-laryngeal direction from plate 3440 (or above plate 3440 when mask portion 3430 is in the orientation shown in FIG. 35A). Conversely, inflation of the cuff 3460 causes the cuff 3460 to pull the support 3470 in the pharyngeal-to-laryngeal direction so that support 3470 is angled with respect to plate 3440 as shown in FIG. 35A.

When a laryngeal mask airway device is in the fully inserted configuration, muscular contraction in the region of the larynx can generate forces in the direction of arrows F as shown in FIG. 35B. These forces bias the inflated cuff towards the midline 3431 of the mask portion. If these forces become strong enough, movement of the inflated cuff towards the midline 3431 and can reduce the size of, or obstruct, the airway provided by the laryngeal mask airway device. In device 3400, support 3470 advantageously resists movement of the inflated cuff in the direction of the arrows F and thereby acts as a counterbalance to these forces.

Another way to make the mask portion resist forces in the direction of arrows F that does not involve use of support 3470 is simply to make the mask portion out of a stiffer material. However, although making the mask portion stiffer would have the beneficial effect of resisting those forces, it would also make the mask portion less pliable and therefore would disadvantageously make the mask portion less amenable to insertion into the airway of a patient. As discussed above in connection with FIG. 17, the mask portion of a laryngeal mask airway device is preferably capable of bending around an axis extending in the left-to-right direction to facilitate insertion into a patient without damaging the structures that define the patient's anatomical airway. Presence of support 3470 does not appreciably increase the amount of force required to make the mask portion 3430 bend around an axis extending in the left-to-right direction (as shown in FIG. 17). So, support 3470 increases the structural integrity of mask portion 3430 (by increasing the mask portion's resistance to forces applied in the direction of the arrows F shown in FIG. 35B) without making it more difficult to insert device 3400 into a patient.

Another function of support 3470 relates to obstruction of the airway by the epiglottis. As is known, one potential drawback to laryngeal mask airway devices is that, when the patient is reclining on their back, the epiglottis sometimes drops down into the aperture defined by the inflated cuff and blocks the airway provided by the device. U.S. Pat. No. 5,297,547 is one example of a patent that discloses using an apertured sheet to prevent the epiglottis from obstructing the airway of a laryngeal mask airway device. In device 3400, if the epiglottis drops down, rather than falling into the passage defined by airway tube 3410 (shown for example in FIG. 34A), the epiglottis will come to rest on support 3470. The apertures 3478 are sufficiently long so that, although the epiglottis may obstruct a portion of the apertures 3478, it will not cover, or obstruct, all of the apertures 3478, and the uncovered portions 3478 effectively prevent the epiglottis from obstructing the airway provided by device 3400.

In contrast to prior art epiglottis supports, support 3470 is attached to the inner wall 3462 of cuff 3460. Due to this attachment, the cuff, when inflated, tends to hold support 3470 in a desired location. If the epiglottis, or any other portion of the anatomy, biases support 3470 in the laryngeal-to-pharyngeal direction, the cuff tends to hold support 3470 in position and resists movement of the support. The cuff 3460 in effect provides an air cushioned support for the support 3470.

Figure 36:
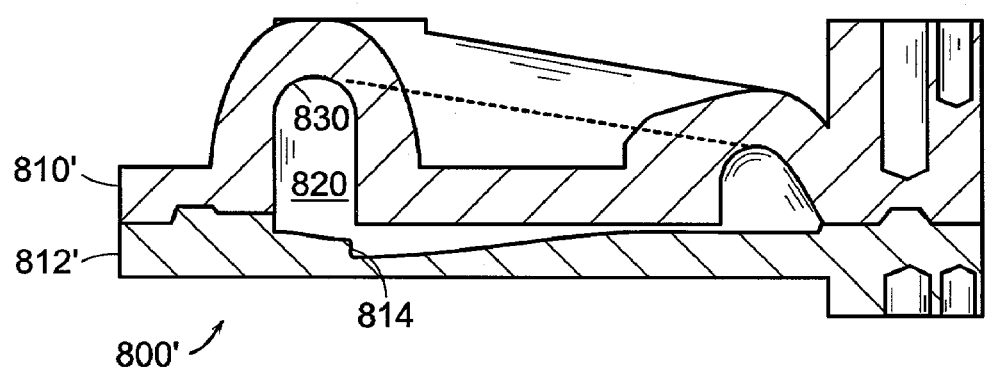
FIG. 36 shows a sectional view of a mold that may be used to form the mask portion shown in FIGS. 35A–35E.

As discussed above, one method of forming mask portion 3430 is to form plate 3440 without a central aperture and to then define support 3470 by cutting the horseshoe shaped notch 3472 into the plate 3440. In the preferred method of manufacture, mask portion 3430 is formed by rotational molding and support 3470 is formed during the rotational molding simultaneously with the rest of mask portion 3430. FIG. 36 shows a sectional view of a mold 800' that may be used to form mask portion 3430. Mold 800' is similar to the mold 800 (shown in FIGS. 8A–8D), and includes a top piece 810' and a bottom piece 812'. Unlike mold 800, in mold 800', the bottom piece 812' defines a recess 814. After mold 800' has been moved or rotated so as to coat all interior walls with the liquid plastic material used to form the mask portion, mold 800' is held in the position shown in FIG. 36 until the liquid plastic material has cured. The presence of recess 814 allows the liquid plastic material to simultaneously form plate 3440 and support 3470. When mask portion 3430 is initially removed from mold 800', the support 3470 is still connected to plate 3440 by a thin layer of cured liquid plastic material. This thin layer of material connecting plate 3440 and support 3470 extends generally along the outline of horseshoe shaped notch 3472 as shown in FIG. 35D. Support 3470 can be easily separated from plate 3440 simply by pulling on the support 3470 enough to tear this thin layer of cured material. This tearing effectively forms horseshoe shaped notch 3472. It will be appreciated that such a procedure is simpler and less expensive than cutting horseshoe shaped notch 3472 out of a substantially flat plate. It will also be appreciated that mold 800' preferably includes features that define the apertures 3478 of support 3470. Once support 3470 is so formed, it is then preferably attached to the inner wall 3642 of the inflated cuff as described above.

Figure 37A:
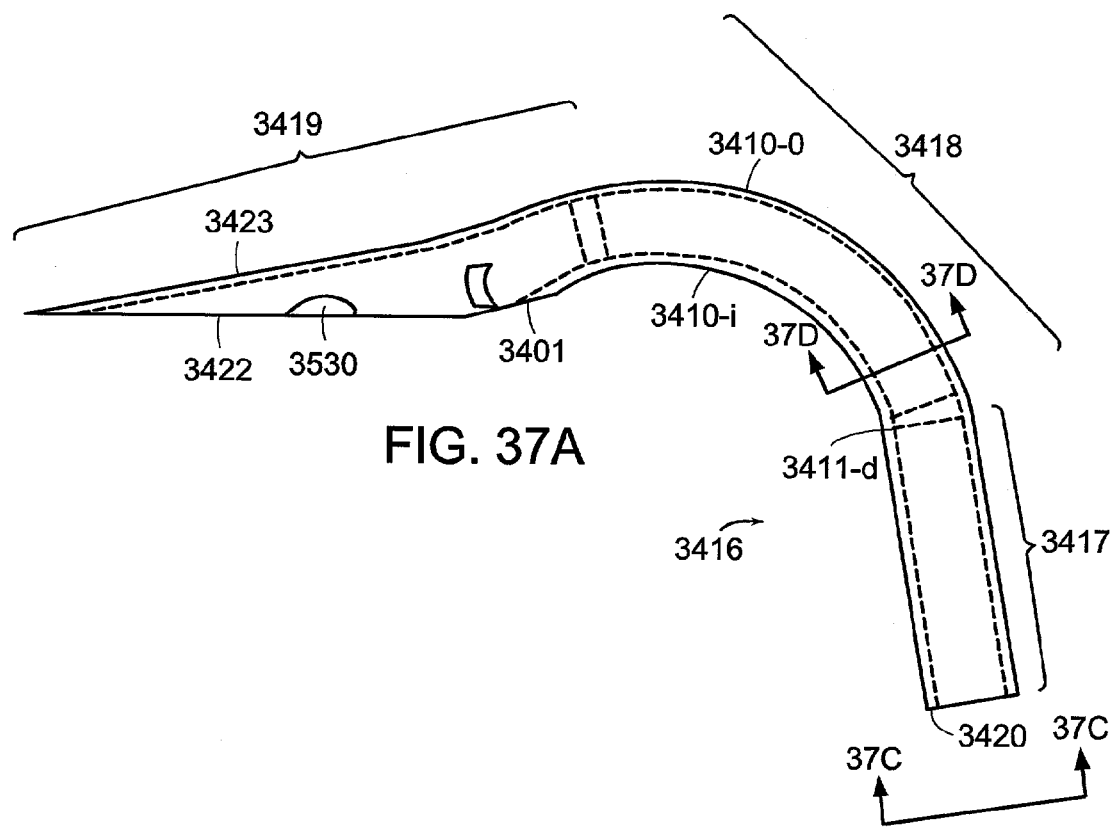
FIG. 37A shows a side view of the integral tube and backplate section of the airway tube of the device shown in FIGS. 34A–34C.
Figure 37B:
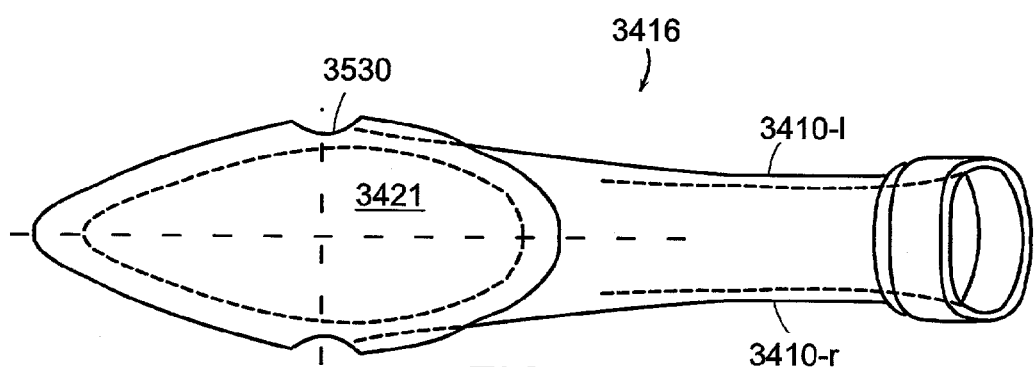
FIG. 37B shows a view of the inner side of the integral tube and backplate section shown in FIG. 37A.
Figure 37C:
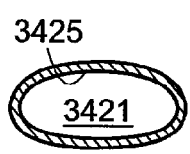
FIG. 37C shows a view of the proximal end of the integral tube and backplate section shown in FIG. 37A taken in the direction of the line 37C—37C as shown in FIG. 37A.
Figure 37D:
FIG. 37D shows a sectional view of the integral tube and backplate section shown in FIG. 37A taken along the line 37D—37D shown in FIG. 37A.

Airway tube 3410 will now be discussed. As with airway tube 410 (shown, e.g., in FIGS. 4A–4C), airway tube 3410 preferably includes two components: a connector section 3411 and an integral tube and backplate section 3416. FIG. 37A shows a side view of tube and backplate section 3416. FIG. 37B shows a view of the anterior side of tube and backplate section 3416. FIGS. 37C and 37D show sectional views taken along the lines 37C—37C and 37D—37D, respectively, as shown in FIG. 37A. FIG. 38A shows a perspective view of connector section 3411. FIGS. 38B and 38C show sectional views of connector section 3411 taken in the direction of lines 38B—38B and 38C—38C, respectively, as shown in FIG. 38A. FIG. 38D shows an end view of the proximal end of connector section 3411 taken in the direction indicated by line 38D—38D as shown in FIG. 38A.

It will be appreciated that connector section 3411 is similar to connector section 411 (shown, e.g., in FIG. 9B) and that integral tube and backplate section 3416 is similar to section 416 (shown, e.g., in FIG. 9E). Some of the common features of connector sections 3411, 411 and integral tube and backplate sections 3416, 416 will now be described. Referring to FIGS. 38A–38D, connector section 3411 includes a proximal portion 3412 and a distal portion 3413. Proximal portion 3412 is preferably cylindrical and configured to couple to standard ventilating or anaesthetic devices. Distal portion 3413 is preferably oblong. Connector section 3411 further includes a disk shaped plate, or flange, 3414. Connector section 3411 defines a sealed internal airway passage 3415 that extends entirely through proximal portion 3412 and distal portion 3413. In the proximal portion 3412, the cross section of passage 3415 is circular and in distal portion 3413, the cross section of passage 3415 is oblong.

Referring to FIGS. 37A–37D, integral airway tube and backplate section 3416 includes a proximal portion 3417, a central or curved portion 3418, and a backplate portion 3419. Section 3416 defines a hollow internal passage 3421 that extends entirely through proximal portion 3417, central portion 3418, and backplate portion 3419. Section 3416 defines a left side 3410-$l$ and a right side 3410-$r$ (shown for example as shown in FIG. 37B). Section 3416 also defines an inner side 3410-$i$ and an outer, or convex, side 3410-$o$ (shown for example as shown in FIG. 37A). As shown for example in FIGS. 34A and 37D, the central portion 3418 of integral tube and backplate section 3416 define longitudinal folds 3425 that extend along the left and right sides of the central portion 3418 and into the backplate portion 3419.

Airway tube 3410 is assembled by coupling connector section 3411 and integral tube and backplate section 3416 together. As shown in FIG. 34A, when the parts are so coupled, flange 3414 of connector section abuts the proximal end 3420 of integral tube and backplate section 3416. Also, the distal portion 3413 of connector section 3411 telescopically extends into the internal passage 3421 defined by the proximal portion 3417 of integral tube and backplate section 3416. When connector section 3411 and section 3416 are assembled, the internal passage 3415 of connector section 3411 communicates with the internal passage 3421 of integral tube and backplate section 3416 so that airway tube 3410 defines a continuous sealed internal passage that extends from the tube's proximal end to the tube's distal end.

When connector section 3411 is fully inserted into proximal portion 3417 to assemble airway tube 3410, the distal end of connector section 3411 is located at the point 3411-$d$ as indicated in FIG. 37A. So, when airway tube 3410 is assembled, the airway tube's internal passage is defined by (1) passage 3415 of connector section 3411, which extends from the proximal end of airway tube 3410 to point 3411-$d$ and (2) the portion of passage 3421 of integral tube and backplate section 3416, which extends from point 3411-$d$ to the backplate portion 3419. In other words, since the distal portion 3413 of connector section 3411 is telescopically inserted into proximal portion 3417, the portion of internal passage 3421 defined by proximal portion 3417 extending from the proximal end 3420 of section 3416 to the point 3411-$d$, does not define the internal airway passage of airway tube 3410 and instead defines a passage designed for receiving the distal portion 3413 of connector section 3411.

With reference to FIG. 34A, in one exemplary embodiment of a female adult size of device 3400, the thickness T30 of the central portion 3418, as measured from the inner side 3410-$i$ to the outer side 3410-$o$, is substantially equal to 12.75 millimeters and the thickness T31 of the bite block is substantially equal to 13.91 millimeters.

Backplate portion 3419 defines a laryngeal side 3422 and a pharyngeal side 3423. When device 3400 is assembled, the laryngeal side 3422 of backplate portion 3419 is attached or fixed to the pharyngeal side 3444 of mask portion 3430. Also, when device 3400 is assembled, the internal passage of airway tube 3410 communicates with the apertures 3478 of support 3470 so that device 3400 defines a sealed airway passage that extends from the proximal end of tube 3410 to the anterior side 3448 of the bowl shaped opening defined by the inflated cuff.

As noted above, connector section 3411 and integral tube and backplate section 3416 are similar to section 411 and section 416 (discussed above, for example, in connection with FIGS. 9A–9G). However, sections 3411 and 3416 additionally include features that facilitate guiding an endotracheal tube through device 3400 and thereby facilitate using device 3400 as an intubating laryngeal mask airway device. For example, as shown in FIG. 37D, in the central portion 3418 of the integral tube and backplate section 3416, the cross section of the airway passage 3421 is characterized by a notch, or recess, 3424 that extends along the inner surface of convex (or outer) side 3410-$o$. This notch 3424, the cross section of which is shaped like a circular arc, preferably extends along the length of the central portion 3418. It will be appreciated if an endotracheal tube is inserted through airway tube 3410, notch 3424 advantageously guides the endotracheal tube along the center of the airway passage 3421. Holding the endotracheal tube in the center of the airway passage facilitates aligning the distal tip of the endotracheal tube with the glottic opening and thereby facilitates intubation. It will also be appreciated that passage 3421 is sized so that if a cylindrical endotracheal tube is inserted into the airway tube 3410, the endotracheal tube will not entirely fill passage 3421, and therefore will not obstruct the airway provided by device 3400. Although the endotracheal tube will fill a cylindrical portion of the passage, defined partially by notch 3424, air will still be able to pass through the airway tube 3410 along the left and right sides of the endotracheal tube.

As shown in FIG. 38D, the airway passage 3415 in the distal portion 3413 of connector section 3411 is characterized by upper and lower notches 3426 for guiding an endotracheal tube. The cross section of the internal passage defined by central portion 3418 preferably smoothly transitions from the one shown in FIG. 37D to one that matches the cross section of the internal passage defined by the distal portion 3413 shown in FIG. 38D, so that there is not an abrupt transition in the shape of the airway passage at the point 3411-$d$. It will be appreciated that in general a variety of shapes for notches or recesses in tube 3410 may be used for guiding a cylindrical endotracheal tube, however, the considerations for designing the notches are generally as follows. In the relatively straight proximal end of airway tube 3410, it is advantageous to have notches in both the inner and outer sides 3410-$i$, 3410-$o$ of the airway tube for holding an inserted endotracheal tube in the center of the airway tube 3410 (as shown in FIG. 38D). When an inserted endotracheal tube extends into the central portion 3418 of integral tube and backplate section 3416, the curve defined by the central portion 3418 will force the endotracheal tube towards the outer side 3410-$o$ of airway tube 3410. Accordingly, in the region of the curved central portion 3418, it is advantageous to accentuate the notch 3424 that extends along the inner surface of the outer side 3410-*o* of the airway tube 3410. It will be appreciated though that notches for guiding an endotracheal tube could extend along the inner surfaces of both the inner and outer sides 3410-*i*, 3410-*i* of the central portion 3418.

Figure 39A:
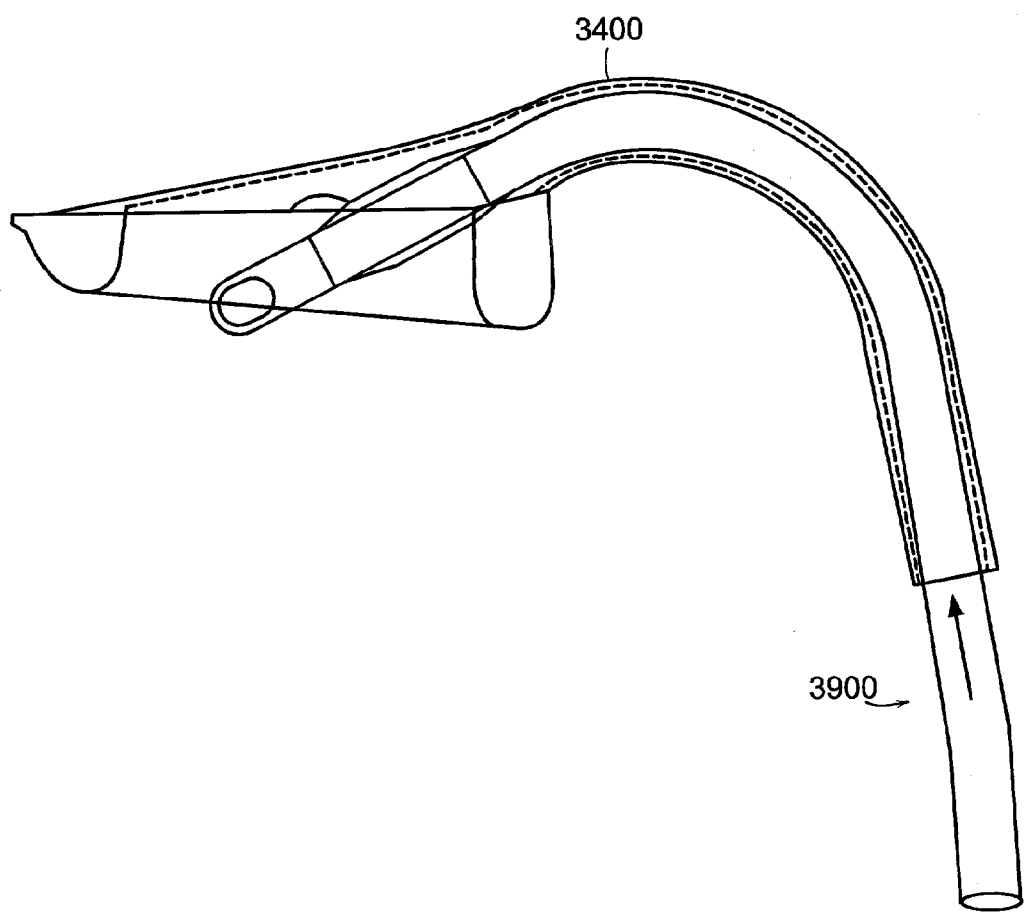
FIG. 39A shows a perspective view of an endotracheal tube being inserted through the device shown in FIGS. 34A–34C.

FIG. 39A shows an endotracheal tube 3900 that has been inserted into device 3400. As shown, the distal tip of tube 3900 has been inserted into the proximal end of airway tube 3410 and advanced through airway tube 3410 until the distal tip of tube 3900 has extended through central aperture 3478 of support 3470. From this position, continued advancement of endotracheal tube 3900 will cause its distal tip to enter the patient's glottic opening.

Figure 39B:
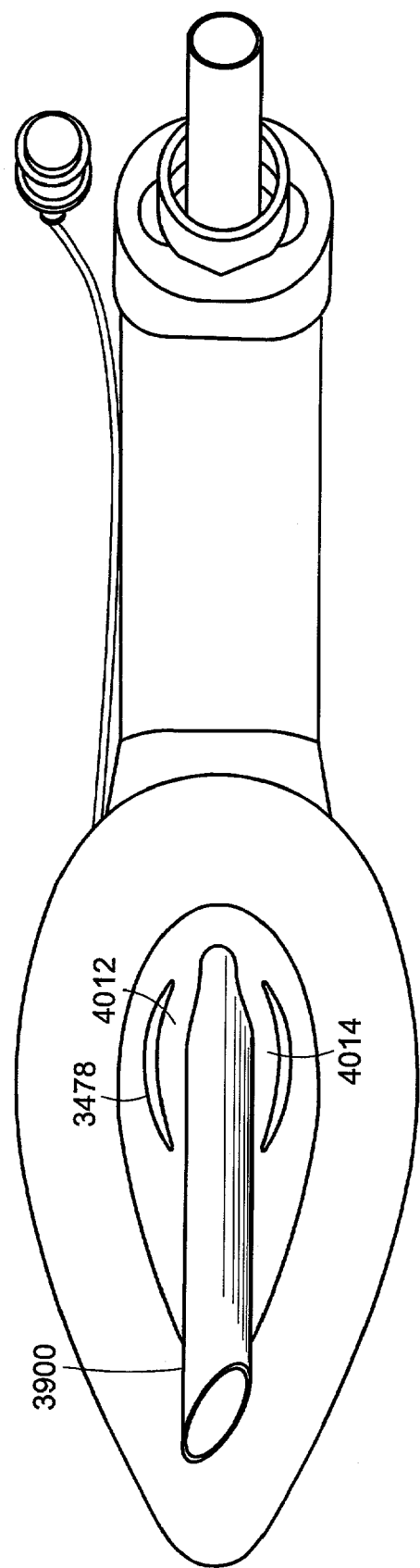
FIG. 39B shows an anterior view of the device shown in FIG. 39A as the endotracheal tube extends through the central aperture defined in the support of the mask portion.

FIG. 39B shows an anterior view of endotracheal tube 3900 extending through device 3400. As shown, the distal tip of endotracheal tube 3900 has extended through the central aperture 3478 of support 3470, thereby pushing the bars 4012, 4014 that define the apertures 3478 laterally, and reducing the size of the apertures 3478 on either side of the central aperture.

FIG. 40A shows another embodiment of mask portion 3430 in which support 3470 defines a fenestration, or cut, represented by dashed line 4010. Support 3470 generally defines two bars 4012, 4014. The central aperture 3478 of support 3470 is disposed between the bars 4012 and 4014. As shown in FIG. 40A, another aperture 3478 of the support is disposed above bar 4012 and another aperture 3478 of the support is disposed below bar 4014. Adding fenestration 4010 to support 3470 effectively detaches the distal end of bars 4012, 4014 from support 3470 and allows the bars to flap up or down with respect to the rest of support 3470. Normally, the bars 4012, 4014 lie generally coplanar with the rest of support 3470. However, when support 3470 includes fenestration 4010, an advancing endotracheal tube can displace the bars 4012, 4014 in the pharyngeal-to-laryngeal direction with respect to the rest of support 3470. When the bars are so displaced, rather than defining three separate apertures 3478, the support 3470 can be thought of as defining a single enlarged aperture, and an advancing endotracheal tube can pass through this enlarged aperture. FIG. 40B illustrates an endotracheal tube 3900 advancing through a support 3470 which defines fenestration 4010. As shown, tube 3900 has displaced the bars 4012, 4014 in the pharyngeal-to-laryngeal direction (i.e., downwards as shown in FIG. 40B) and the tube 3900 advances through support 3470 without stretching the bars laterally as shown in FIG. 39B. It will be appreciated that the mold used to produce mask portion 3430 may also include features for defining fenestration 4010.

Figure 34D:
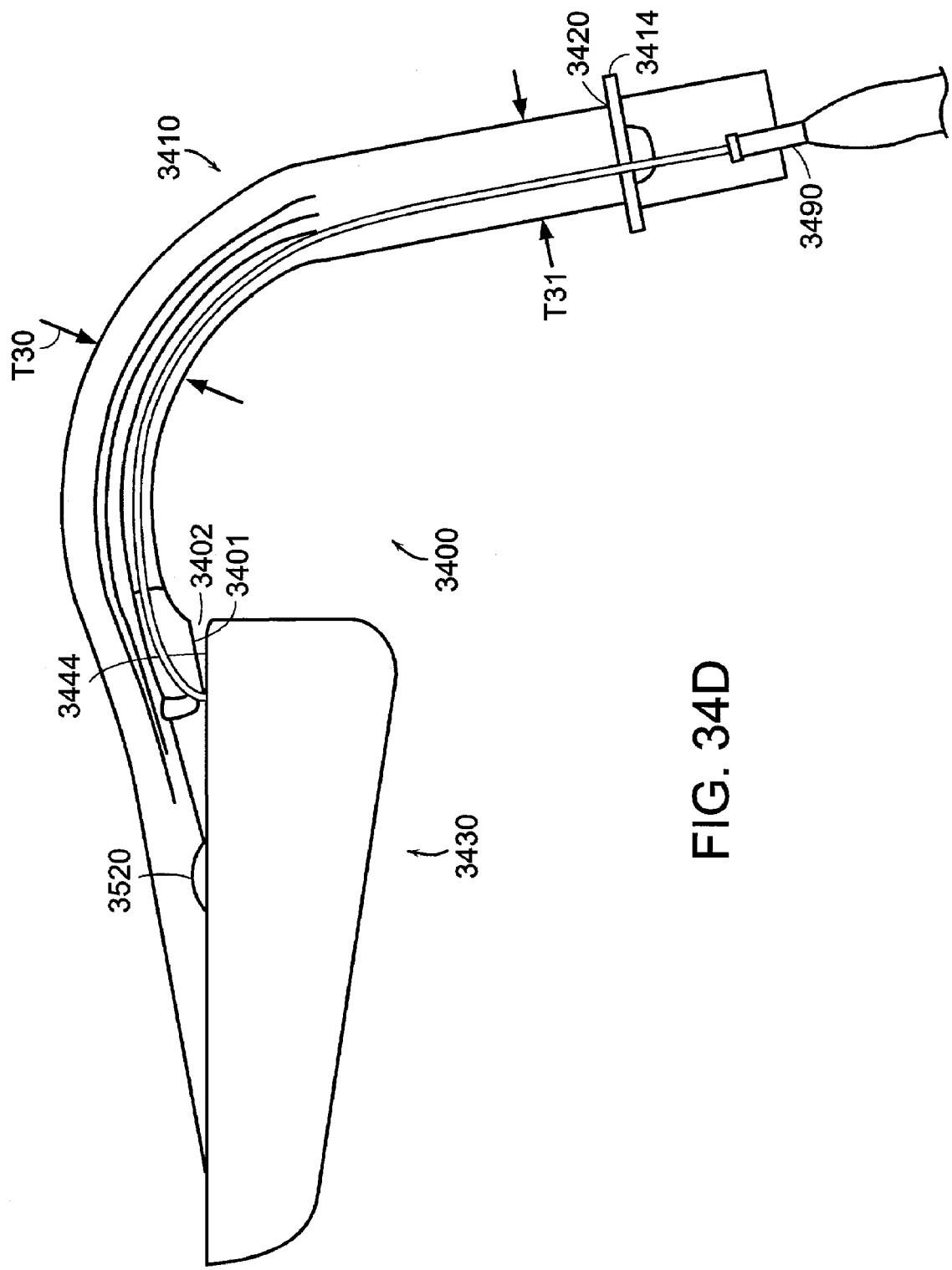

As noted above, to facilitate insertion of a laryngeal mask airway device into a patient, the deflated device is preferably as thin as possible. With reference to FIG. 16A, the thickest part of device 400, when deflated, is shown at T11 and is located at the proximal end of the mask portion. In device 3400, the airway tube 3410 advantageously defines a feature that allows this thickness to be reduced. As shown in FIG. 9E, the laryngeal side 422 of the backplate portion of the airway tube 410 is substantially planar. However, as shown in FIG. 37A, the laryngeal side 3422 of the backplate portion of the airway tube 3410 is not planar. In particular, the proximal end of the laryngeal side 3422 includes a recessed portion 3401 that is angled with respect to the rest of the laryngeal side. As shown in FIG. 34D, during assembly of device 3400, when the mask portion 3430 is initially mated with the airway tube 3410, the recessed portion of the laryngeal side 3422 of the backplate portion, causes a gap 3402 to be defined between the pharyngeal side of the mask portion and the laryngeal side of the backplate portion. This gap is eliminated when fabrication of the device 3400 is complete (as shown in FIG. 34A) by adhering the proximal end of pharyngeal side 3444 of the plate 3440 of mask portion 3430 to the recessed portion 3401 of the laryngeal side of the backplate portion of the airway tube 3410. It will be appreciated that when device 3400 is deflated, the presence of the recessed portion 3401 allows the thickness of the laryngeal mask airway device to be reduced as compared with device 400 at the point shown in FIG. 16A at T11.

When the device 3400 is in the fully inserted configuration, presence of recessed portion 3401 may reduce the pressure applied by the proximal end of mask portion 3430 to the patient's anatomy. However, this reduction in pressure does not appreciably degrade the quality of the seal around the glottic opening provided by device 3400. The quality of this seal is affected less by pressure between the inflated cuff and the patient's anatomy than by the area of contact between the inflated cuff and the patient's anatomy. Device 3400 advantageously increases this area of contact (and thereby improves the quality of the seal), by forming the cuff 3460 out of a very thin layer of a very soft material. In exemplary embodiments, the material used to form mask portion 3430 is characterized by a durometer of substantially fifty five on the Shore A scale and the thickness of the cuff wall is preferably substantially equal to 0.2 millimeters. Mask portion 3430 may be formed from PVC. When the device 3400 is located in the fully inserted configuration, the intra cuff pressure is preferably between twenty and eighty centimeters of water. Use of this relatively low intra cuff pressure in combination with the very soft and pliable cuff advantageously increases the area of contact between the cuff and the patient's anatomy and thereby provides a high quality seal around the glottic opening.

The shape of the inflated cuff, and in particular the laryngeal side of the inflated cuff, may also be selectively tailored to increase or decrease the area of contact between the cuff and the patient's anatomy to thereby affect the quality of the seal as well as other parameters. For example, FIGS. 14 and 34C illustrate two different profiles of the laryngeal side of the inflated cuff. A cuff configured as shown in FIG. 14 provides less area of contact with the patient's anatomy than does the cuff shown in FIG. 34C. In particular, the distal tip of the cuff shown in FIG. 34C provides an increased area of contact. The increased area of contact in the cuff shown in FIG. 34C is provided by "rounding" or "softening" the relatively sharp apex of the distal tip of the central aperture of the cuff shown in FIG. 14. It will be appreciated that the profile of the laryngeal side of the cuff shown in FIG. 14 is similar to that of a well known product sold by LMA International SA of Henley, England known as the "Classic". The distal tip of the cuff shown in FIG. 34C provides an increased area of contact with the patient's anatomy and may thereby increase the quality of seal provided by the device. However, the profile of the laryngeal side of the Classic's cuff (shown generally in FIG. 14), and in particular the relatively sharp apex at the distal end of the cuff's central aperture, may actually be preferred because of other factors. Clinical experience has shown that laryngeal mask airway devices with cuffs having the profile of the Classic may provide improved ventilation characteristics. Accordingly, the profile of the laryngeal side of the Classic's cuff may be the preferred profile for all laryngeal mask airway devices disclosed herein.

As discussed above in connection with FIG. 20, it can be advantageous to provide the mask portion with a recess 2010. Such a recess 2010 facilitates placing the backplate portion of the integral tube and backplate section at a desired location on the mask portion during assembly of the laryngeal mask airway device. As indicated by line 3510 (shown in FIG. 35D), mask portion 3430 may also define a recess for locating the airway tube during assembly. Also, as shown in FIGS. 34A, 34B, and 35D, mask portion 3430 may also include locating tabs 3520. As shown in FIGS. 37A and 37B, the backplate portion 3419 of integral tube and backplate section 3416 may also define recesses 3530. During assembly of device 3400, locating tabs 3520 mate with recesses 3530 and thereby facilitate locating the airway tube 3410 at a desired position relative to the mask portion 3430.

As discussed above, support 3470 advantageously (1) increases the structural integrity of mask portion 3430 without detrimentally affecting the ease of insertion of device 3400 and (2) prevents the epiglottis from obstructing the airway provided by device 3400. Several embodiments of support 3470 have been discussed above. However, it will be appreciated that the invention embraces other embodiments of supports that provide similar functions. FIG. 41A shows a top view of another support 4170 constructed according to the invention. FIG. 41B shows a side view of support 4170 taken in the direction indicated by arrow 41B—41B in FIG. 41A.

As shown, support 4170 includes a horseshoe shaped rim 4172 and a central bar 4174. Rim 4172 extends from a proximal end 4176 to distal ends 4178. Bar 4174 is attached, or fixed, to rim 4172 at the proximal end 4176 and extends along a midline 4180 about two thirds of the way towards the distal ends 4178.

FIG. 35A generally depicts a side view of a mask portion 3430 in which a support 4170 has been installed. When viewed from the side, support 4170 will generally follow the dotted lines used in FIG. 35A to denote the location of support 3470. Support 4170 is preferably adhered to the inner wall 3462 of the cuff, as was support 3470.

It will be appreciated that like support 3470, support 4170 also resists compression of the mask portion due to forces exerted in the direction of the arrows F shown in FIG. 35B. Also, support 4170 does not significantly increase the force required to bend the mask portion around an axis extending in the left-to-right direction as shown in FIG. 17. Also, the central bar 4174 provides the function of lifting the epiglottis, or preventing the epiglottis from blocking the airway provided by the laryngeal mask airway device. So, support 4170 provides similar functions as the above-described embodiment of support 3470.

FIGS. 42 and 43 show other embodiments of supports 4270, 4370 constructed according to the invention. Support 4270 (FIG. 42) is similar to support 4170, however, support 4270 does not include a central bar. Support 4370 (FIG. 43) is similar to support 4270 in that it does not define a central bar. However, support 4370 is generally elliptical rather than being horse shoe shaped as in the case of supports 4170 and 4270. So, although supports 4270, 4370 may be used to enhance the structural integrity of the mask portion, and resist collapse of the mask portion in the presence of forces exerted in the direction of the arrows F as shown in FIG. 35B, supports 4270, 4370 do not assist with preventing the epiglottis from blocking the airway provided by the laryngeal mask airway device. It will be appreciated that support 4370 could be modified to include a central bar and thereby also assist with preventing the epiglottis from blocking the airway provided by the laryngeal mask airway device.

Supports such as 4170 and 4270 may be adhered to the inner wall 3462 of the cuff of the mask portion. Preferred materials for constructing supports 4170, 4270, 4370 are PVC. Preferably, the material used to construct these supports is characterized by a durometer of about ninety on the Shore A scale of hardness. These supports may be about 0.7 millimeters thick.

Figure 44:
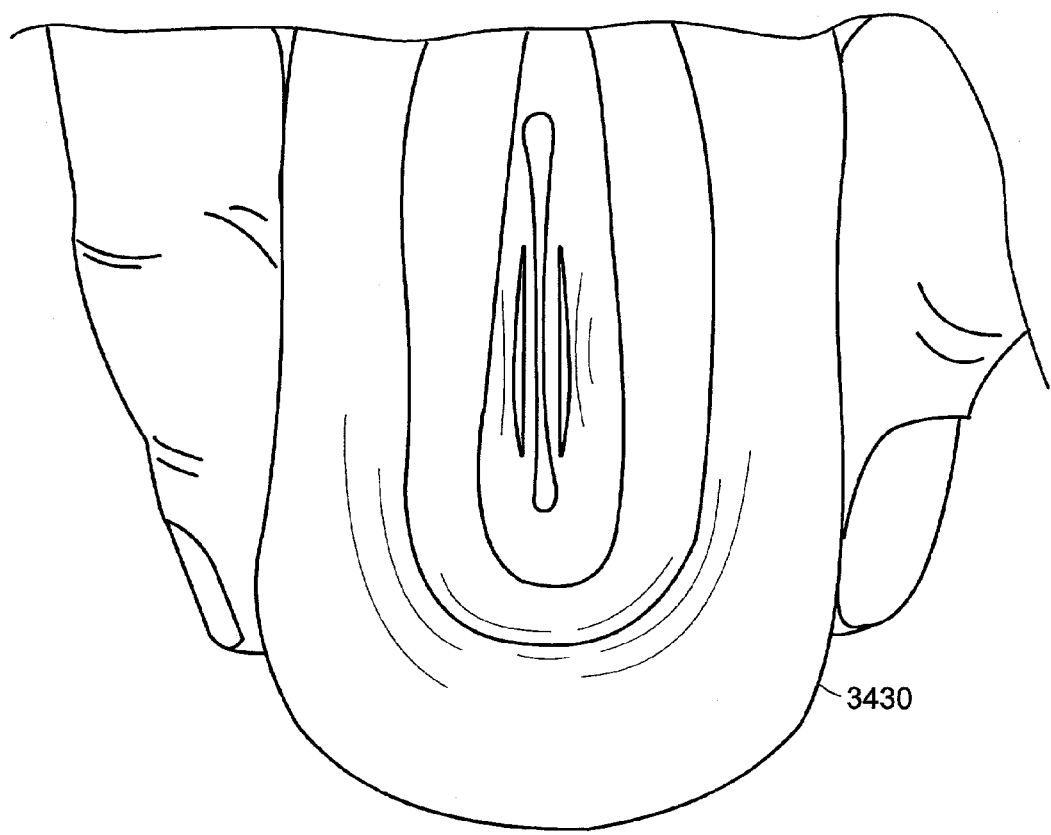
FIG. 44 shows an anterior view of a mask portion of the type shown in FIGS. 35A–35E being squeezed between two fingers to illustrate the response of the mask portion to pressure exerted when the mask portion is disposed within a patient.

An advantage to using supports like 4170 and 4270 is that they may be fabricated from material that is generally stiffer, or harder, than the material used to form the mask portion of the laryngeal mask airway device. In fact, one potential disadvantage to support 3470 (as shown in FIGS. 35A–E), is that since it is generally made from the same material used to form the rest of the mask portion, the support 3470 may be softer than desired for sufficiently strengthening the mask portion. FIG. 44 illustrates a mask portion 3430, which includes a support 3470, being squeezed between two fingers. The pressure applied by the illustrated fingers is in the direction of the arrows F as shown in FIG. 35B, and illustrates how the mask portion may react to pressure applied by anatomical structures of a patient when the mask portion is inserted within a patient. As shown in FIG. 44, the pressure causes the mask portion to partially collapse. More specifically, as a result of the applied pressure, the central aperture defined by the inflated cuff is reduced and the apertures 3478 defined by the support 3470 are also reduced in size. These size reductions, which can occur even if the support 3470 is thicker than the plate 3440 of the mask portion, disadvantageously reduce the size of the airway provided by a laryngeal mask airway device using mask portion 3430.

Figure 45A:
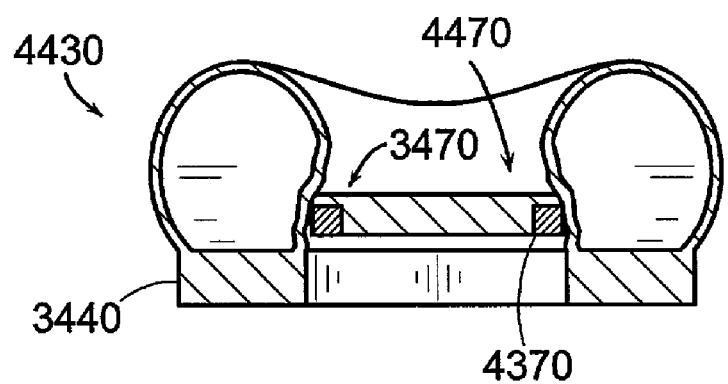
FIG. 45A shows a sectional view of another mask portion constructed according to the invention.
Figure 45B:
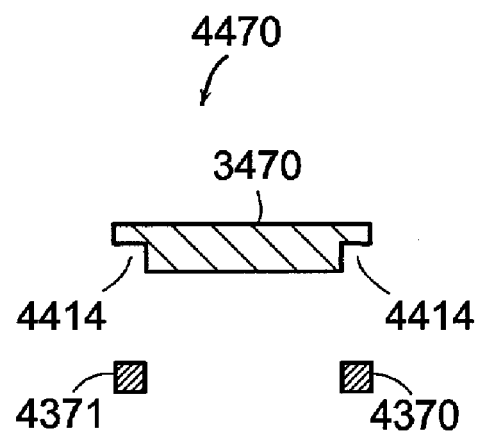
FIG. 45B shows an exploded view of the support shown in FIG. 44A.
Figure 45C:
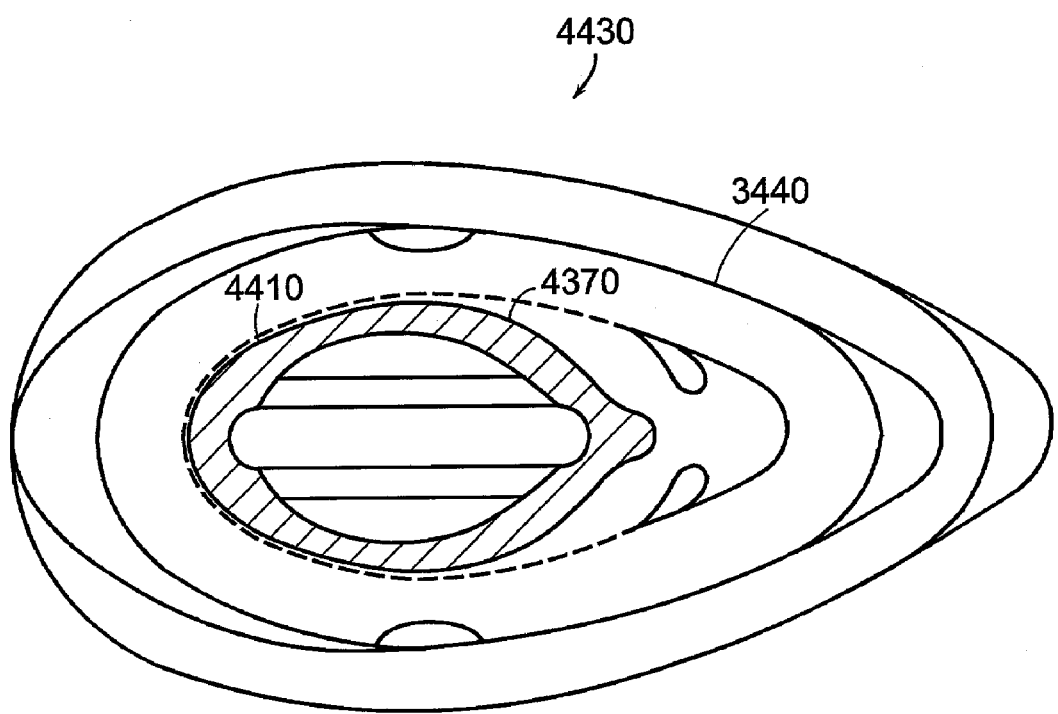
FIG. 45C shows a posterior aspect of the mask portion shown in FIG. 45A.

One way to overcome these difficulties is to fashion a support using a combination of the plate-like support 3470 (as shown, e.g., in FIGS. 35A–E) and the ring-like support 4370 shown in FIG. 43. FIG. 45A shows a sectional view of a mask portion 4430 including such a support 4470. FIG. 45A is a sectional view of mask portion 4430 taken in the same direction as FIG. 35E (i.e., in the direction of line 35E—35E as shown in FIG. 35A). FIG. 45B shows an exploded sectional view of support 4470 taken from the same perspective as FIG. 45A. FIG. 45C shows a view of a posterior aspect of mask portion 4430. Support 4470 includes a plate-like support 3470 and a ring-like support 4370. Referring to FIG. 45C, horse shoe shaped dashed line 4410 represents the places at which plate-like support 3470 is detached from the plate 3440 of mask portion 4430, and the location of ring-like support 4370 is shown by the cross-hatched generally elliptical ring. Plate-like support 3470 defines a ring-like notch 4414 for receiving ring-like support 4370. Ring-like support 4370 is preferably adhered to plate-like support 3470 so that ring-like support 4370 fits into the notch 4414.

Figure 46:
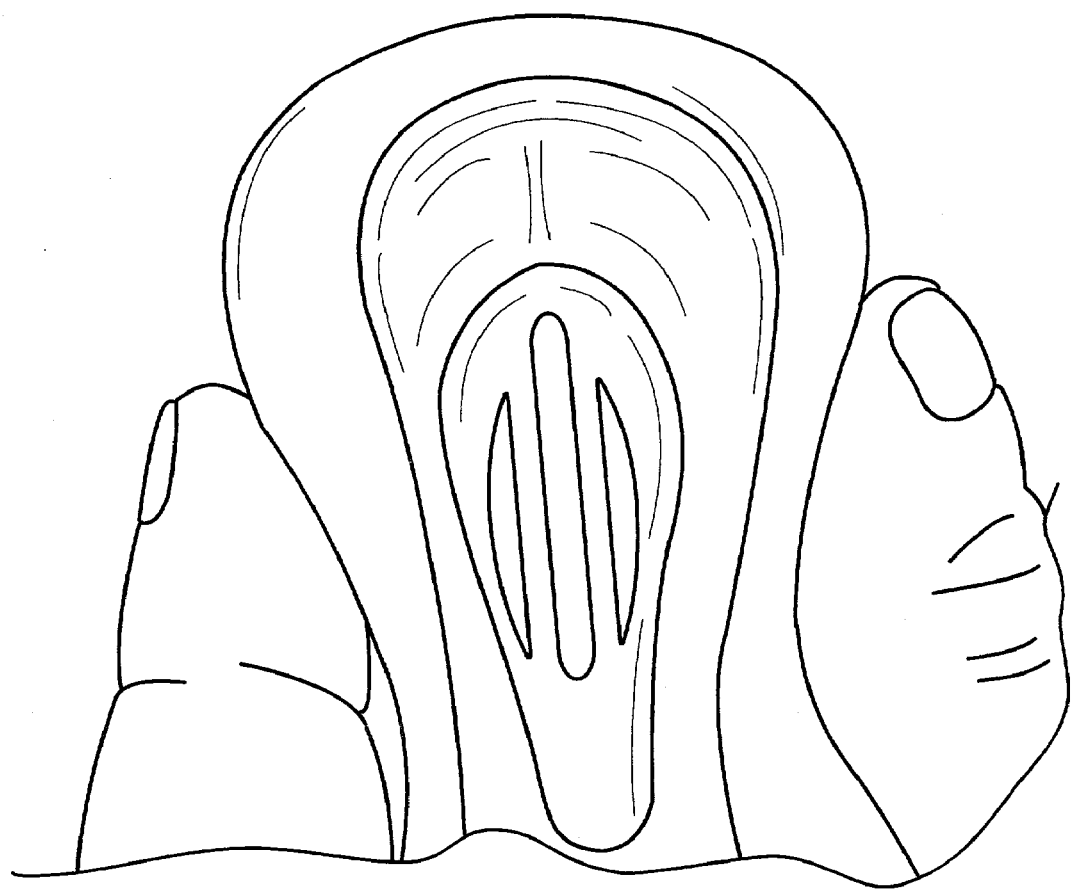
FIG. 46 shows an anterior view of a mask portion of the type shown in FIGS. 45A–45C being squeezed between two fingers to illustrate the response of the mask portion to pressure exerted when the mask portion is disposed within a patient.

In operation of laryngeal mask airway devices constructed using mask portion 4430, (1) the apertures 3478 of plate-like support 3470 prevent the epiglottis from blocking the airway provided by the device and (2) the ring-like support 4370 tends to prevent the apertures 3478 from being closed even when pressure is applied to the mask portion 4430 in the direction of the arrows F. FIG. 46 shows a view of an anterior aspect of a mask portion 4430 being squeezed between two fingers. As shown, although the central aperture defined by the inflated cuff is reduced in size by the pressure applied by the fingers, the ring-like support has resisted compression of the plate-like support and thereby resisted compression of the apertures 3478.

As discussed above, support 3470 is preferably formed by rotational molding simultaneously with the rest of the mask portion. However, it will be appreciated that support 3470 could also be formed of a separate material and incorporated into the laryngeal mask airway device after the mask portion has been formed. For example, a mask portion such as the ones shown in FIGS. 5A–5E could be formed by rotational molding and the support 3470 could then subsequently be incorporated into the mask portion. Such a support could be formed, for example, from the same material used to form the airway tube of the laryngeal mask airway device.

Figure 47A:
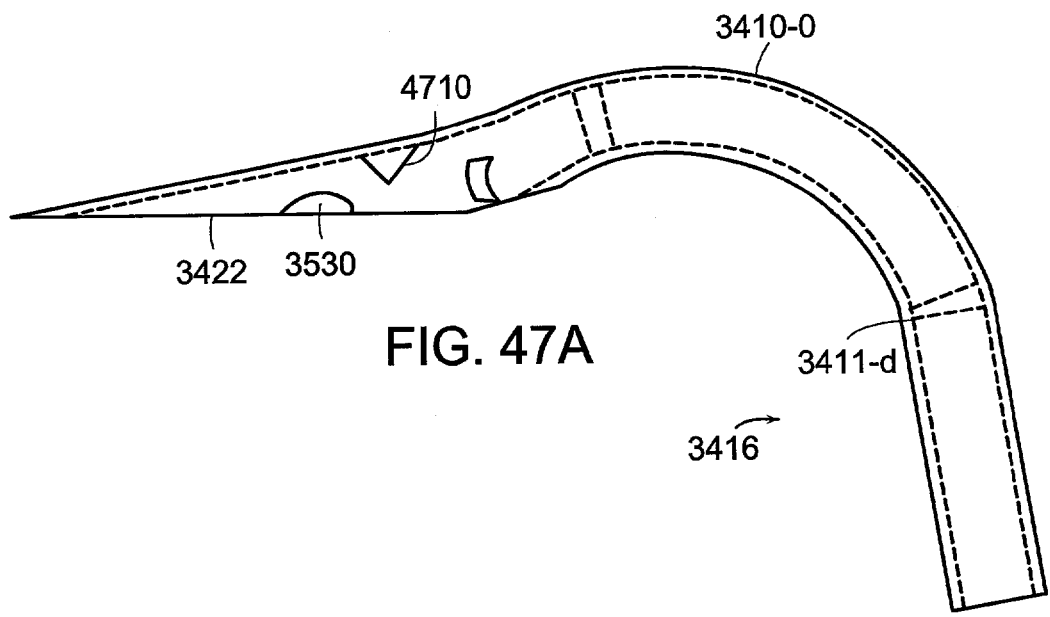
FIG. 47A shows a side view of another embodiment of the integral tube and backplate section of the airway tube of a laryngeal mask airway device constructed according to the invention.
Figure 47B:
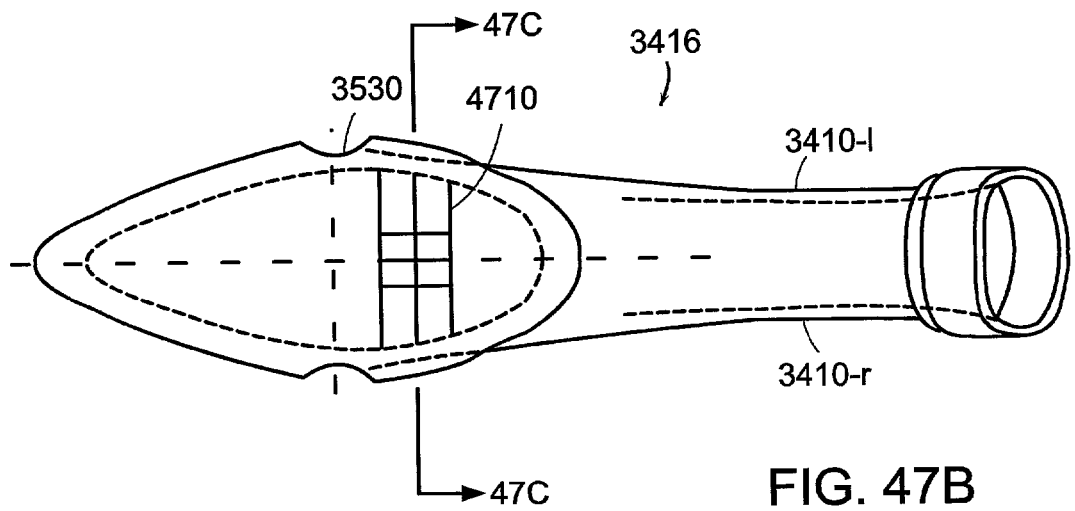
FIG. 47B shows a view of the inner side of the integral tube and backplate section shown in FIG. 47A.
Figure 47C:
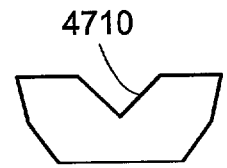
FIG. 47C shows a view of the bar taken in the direction of line 47C—47C as shown in FIG. 47A.
Figure 47D:
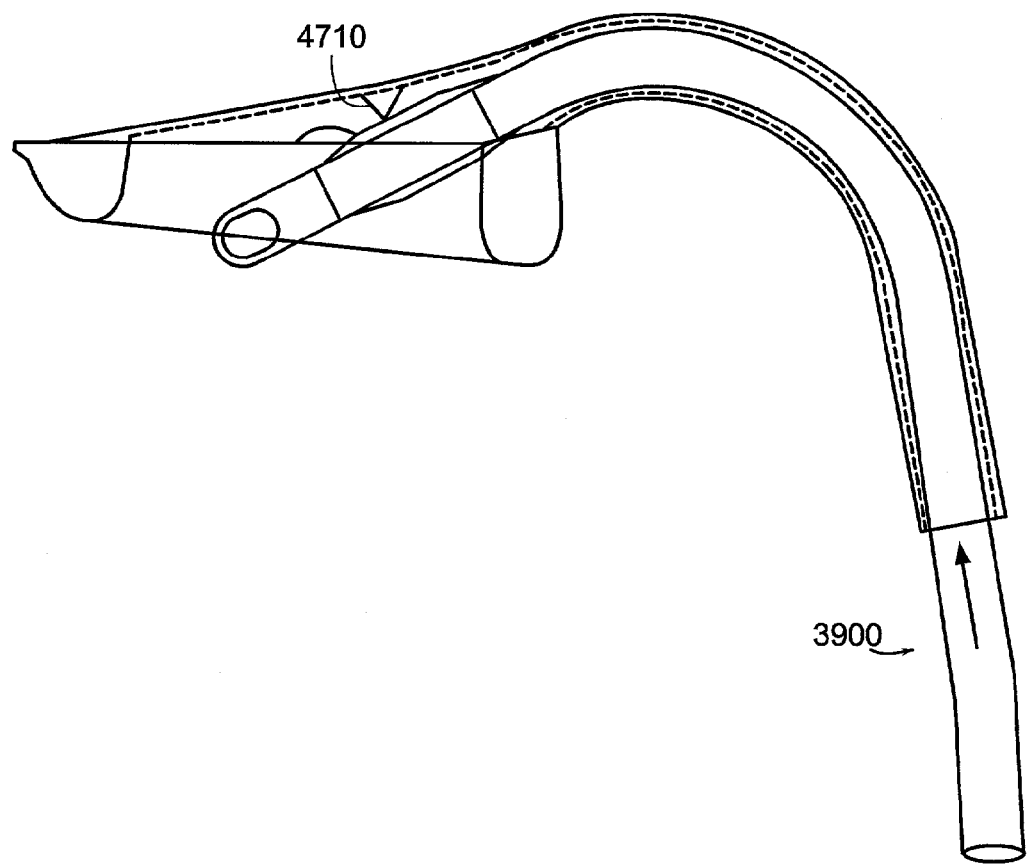
FIG. 47D shows an endotracheal tube being inserted through a laryngeal mask airway device constructed according to the invention so as to include a bar of the type shown in FIGS. 47A–47C.

FIGS. 47A–47C illustrate another modification that may be made to the airway tube of a laryngeal mask airway device constructed according to the invention useful for guiding an endotracheal tube. The airway tube shown in FIGS. 47A and 47B has been modified to include a bar 4710. The bar 4710 is disposed in the backplate portion of the airway tube. More specifically, the bar 4710 extends in the left-to-right direction across the inner surface of the outer, or convex, side 3410-*o* of the backplate portion of the airway tube. FIG. 47C shows a sectional view of bar 4710 taken in the direction of line 47C—47C as shown in FIG. 47A. As shown in FIG. 47C, bar 4710 defines a v-shaped notch 4720. The v-shaped notch 4720 extends in the proximal-to-distal direction and is positioned for guiding an endotracheal tube. More specifically, the v-shaped notch 4720 helps to hold an endotracheal tube in the mid-line during insertion and also guides the distal tip of the endotracheal tube towards the glottic opening. FIG. 47D shows a sectional side view of an endotracheal tube 3900 being inserted through a laryngeal mask airway device constructed according to the invention so as to include a bar 4710.

Figure 48A:
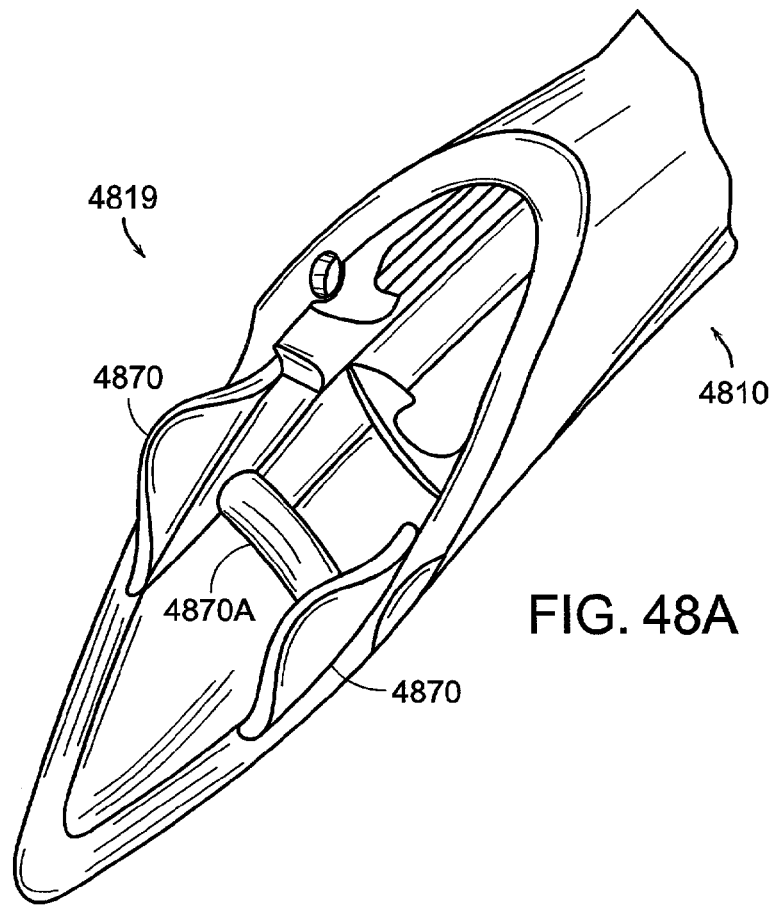
FIG. 48A shows a perspective view of yet another embodiment of the integral tube and backplate section of an airway tube constructed according to the invention.
Figure 48B:
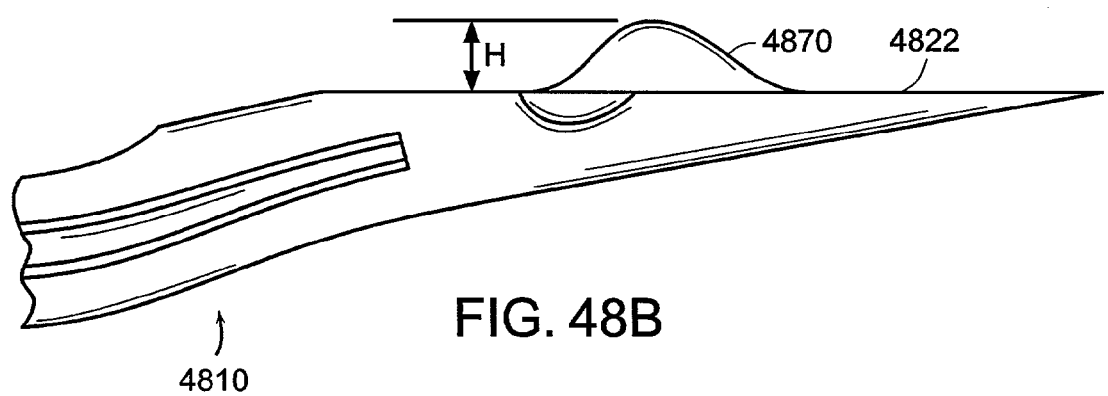
FIG. 48B shows a side view of the integral tube and backplate section shown in FIG. 48A.

FIG. 48A shows a perspective anterior view of the backplate portion 4819 of another embodiment of an airway tube 4810 constructed according to the invention. FIG. 48B shows a side view of the airway tube 4810 shown in FIG. 48A. Airway tube 4810 is similar to airway tubes discussed above (e.g., airway tube 3410 as shown in FIG. 34A). However, airway tube 4810 additionally includes two tabs, or ridges, 4870 disposed in the backplate portion 4819 of the airway tube. Tabs 4870 extend from the laryngeal side 4822 in the pharyngeal-to-laryngeal direction. Referring to FIG. 48B, in an example embodiment, in an adult female size the height H of the tabs 4870 (or the amount that the tabs extend away from the laryngeal side 4822 in the pharyngeal-to-laryngeal direction) is substantially equal to 5.8 millimeters. Airway tube 4810 may also include a bar, or lateral reinforcement, 4870A, which extends in the left to right direction between the two tabs 4870. Airway tube 4810 is preferably formed by molding a single monolithic piece including tabs 4870 and bar 4870A.

Figure 48C:
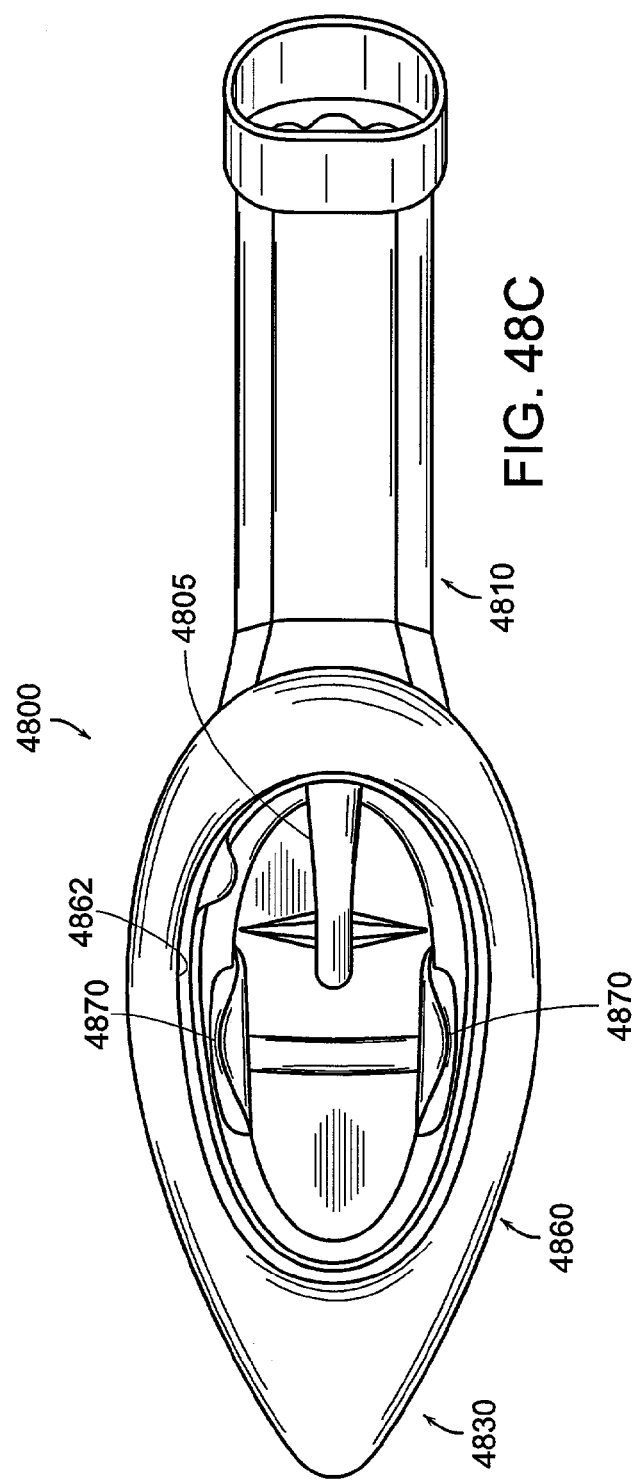
FIG. 48C shows a view of the anterior side of a laryngeal mask airway device constructed according to the invention using the airway tube shown in FIGS. 48A and 48B.
Figure 48D:
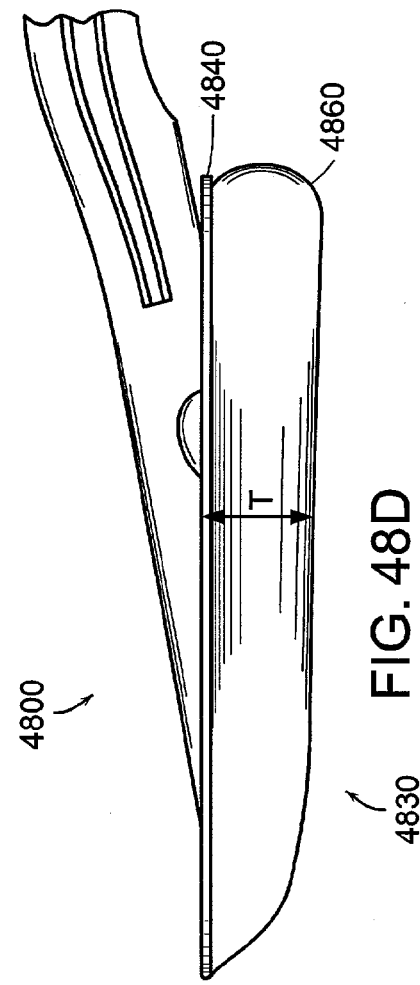
FIG. 48D shows a side view of the device shown in FIG. 48C.

FIG. 48C shows a view of the anterior side of a laryngeal mask airway device 4800 constructed according to the invention using the airway tube 4810 shown in FIGS. 48A and 48B. FIG. 48D shows a side view of the device 4800. Device 4800 is similar to the above-discussed device 400 (shown for example in FIGS. 4A–4C) and is made by attaching a mask portion 4830 to the airway tube 4810. As shown in FIG. 48C, the tabs 4870 are spaced away from the inner wall 4862 of the inflated cuff 4860 and the tabs 4870 are generally located within the hollow bowl shaped aperture defined by the inflated cuff. The tabs 4870 are preferably shaped to generally match the negative imprint of the pyriform fossae so that, when the device 4800 is in the fully inserted configuration the tabs rest within spaces defined by the patient's anatomy.

As discussed above, when a laryngeal mask airway device is in the fully inserted configuration, muscular contraction in the region of the larynx can generate forces in the direction of arrows F as shown in FIG. 35B. These forces bias the inflated cuff towards the midline 3431 of the mask portion. If these forces become strong enough, movement of the inflated cuff towards the midline 3431 and can reduce the size of, or obstruct, the airway provided by the laryngeal mask airway device. In device 4800, the tabs 4870 on the airway tube 4810 advantageously resist movement of the inflated cuff 4860 in the direction of the arrows F (FIG. 35B) and thereby act as a counterbalance to these forces. Also, the presence of tabs 4870 advantageously does not appreciably increase the difficulty of inserting the device 4810 into a patient. It will be appreciated that tabs 4870 are an alternative to the supports 3470, 4170, 4270, 4370 discussed above, and that tabs 4870 may be used alone or in combination with such supports. Also, while the preferred embodiment includes two tabs 4870, additional tabs may also be included on the airway tube.

Since the airway tube is generally made of stiffer material than the mask portion, the airway tube is generally more capable than the mask portion of resisting compressive forces. The tabs 4870, which are part of the airway tube 4810, advantageously use the natural stiffness of the airway tube to support the more pliable mask portion 4830 so as to maintain an open airway passage even in the presence of compressive forces generated in the patient. Also, since portions of the tabs 4870 can rest in the patient's pyriform fossae, the patient's anatomy can assist with holding the tabs in place and resisting compression of the mask portion towards the midline. Finally, bar 4870A increases the stiffness of the tube in the left-to-right direction thereby helping to hold the tabs 4870 apart.

The amount by which the tabs 4870 extend into the bowl shaped aperture defined by the inflated cuff 4860 depends on the thickness of the plate 4840 of the mask portion 4830. In one embodiment in which the thickness of plate 4840 is about 4 millimeters, the tabs 4870 extend into the bowl shaped aperture defined by the inflated cuff 4860 only by about 2 millimeters. Although the tabs 4860 extend into the aperture defined by the cuff 4860 by only a small amount, the tabs 4860 still advantageously resist compressive forces generated inside the patient and tend to resist obstruction of the airway provided by the laryngeal mask airway device. However, it may be advantageous to make the plate 4840 even thinner and have the tabs 4870 extend further into the bowl shaped aperture defined by the inflated cuff 4860. The height of the inflated mask portion 4830 in the region of the tabs 4870, shown by the arrow T in FIG. 48D, may affect the ability of the tabs 4870 to hold the cuff in an open position. The height of the inflated mask portion 4830 may for example be selected so that the distance T, as shown in FIG. 48D, is between about 15 and 18 millimeters when the cuff is not inserted into a patient and when it is inflated to an intra cuff pressure of about 60 cm $H_2O$.

As explained above, when a laryngeal mask airway device is in the fully inserted configuration and the patient is reclining on his or her back, the epiglottis sometimes drops down into the aperture defined by the inflated cuff and blocks the airway provided by the device. In device 4800, if the epiglottis drops down, rather than falling into the passage defined by airway tube 4810, the epiglottis is supported by bar 4805. Bar 4805 is preferably formed as an integral part of mask portion 4830 during the rotational molding process.

Figure 49A:
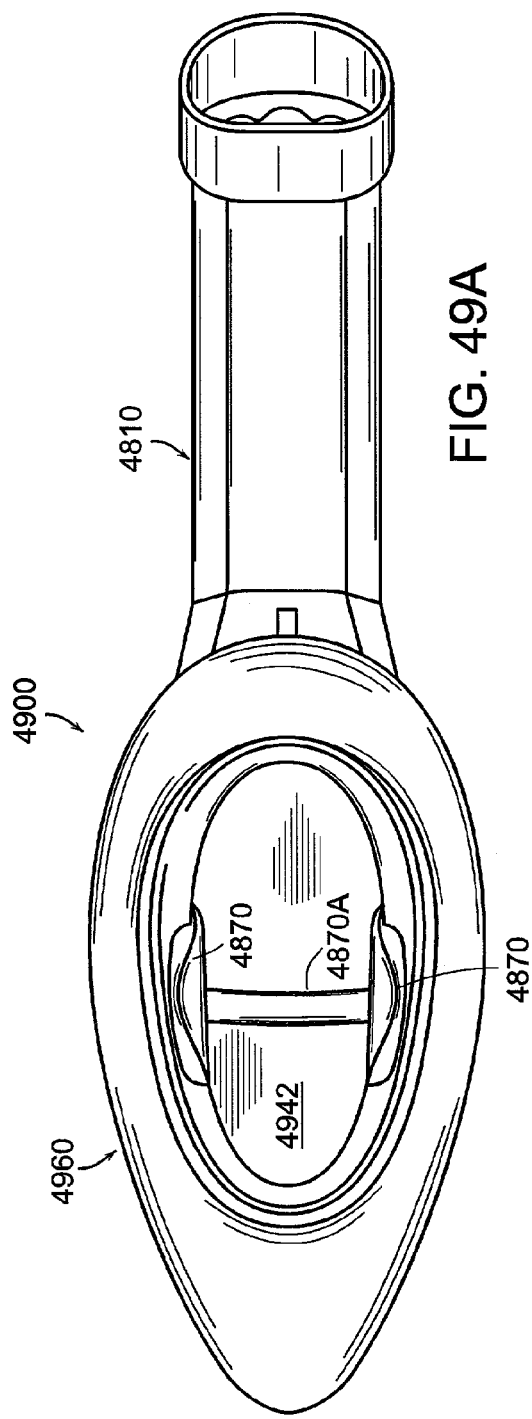
FIG. 49A shows an anterior perspective view of another laryngeal mask airway device constructed according to the invention.
Figure 49B:
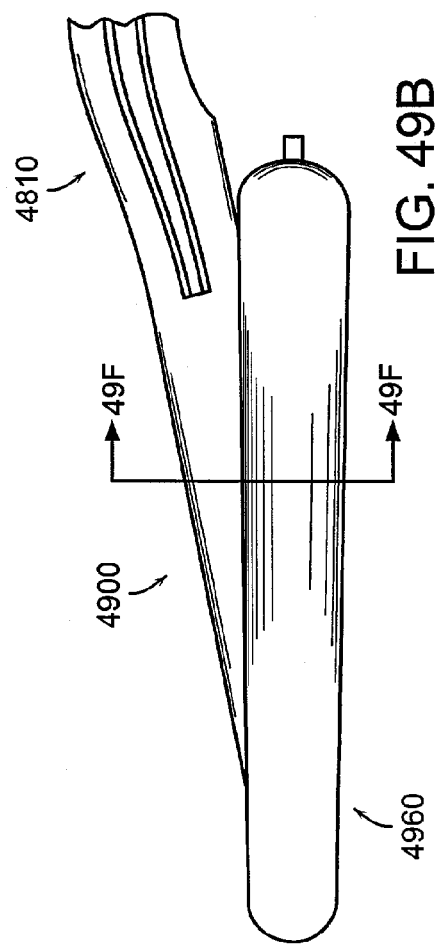
FIG. 49B shows a side view of the device shown in FIG. 49A.
Figure 49C:
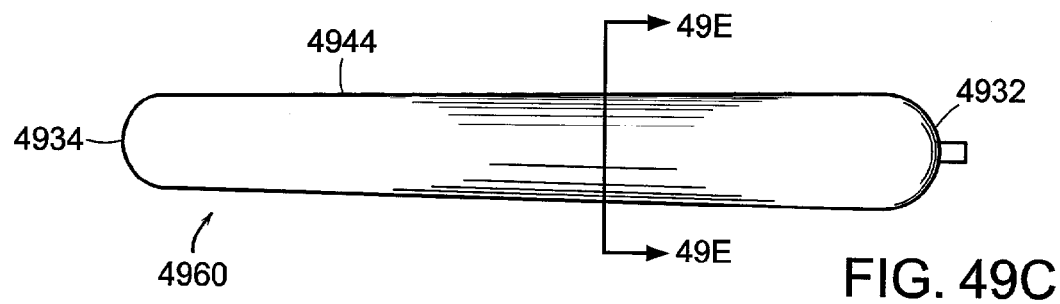
FIGS. 49C and 49D show side and anterior views, respectively, of the cuff shown in FIGS. 49A and 49B.
Figure 49D:
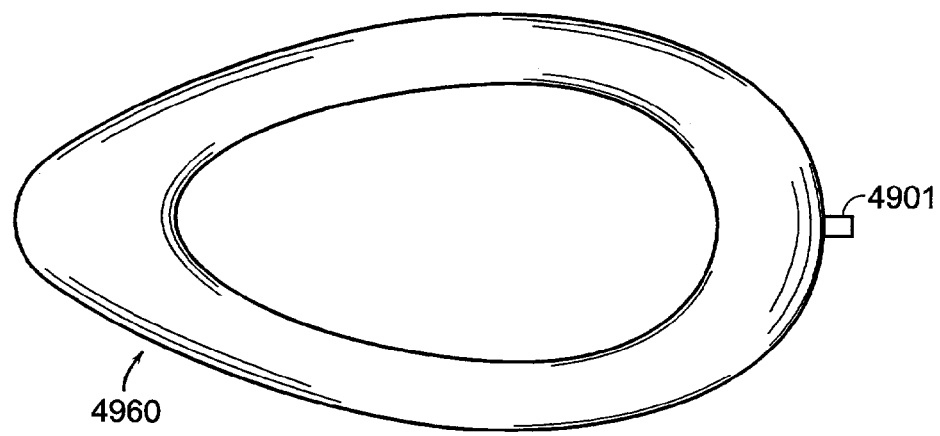
Figure 49E:
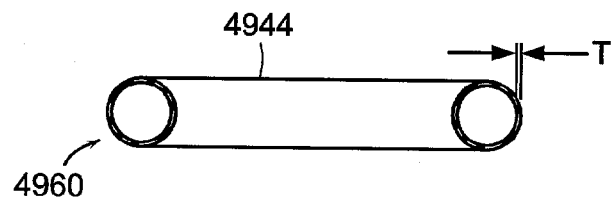
FIG. 49E shows a sectional view of the cuff shown in FIG. 49C taken in the direction of arrow 49E—49E.
Figure 49F:
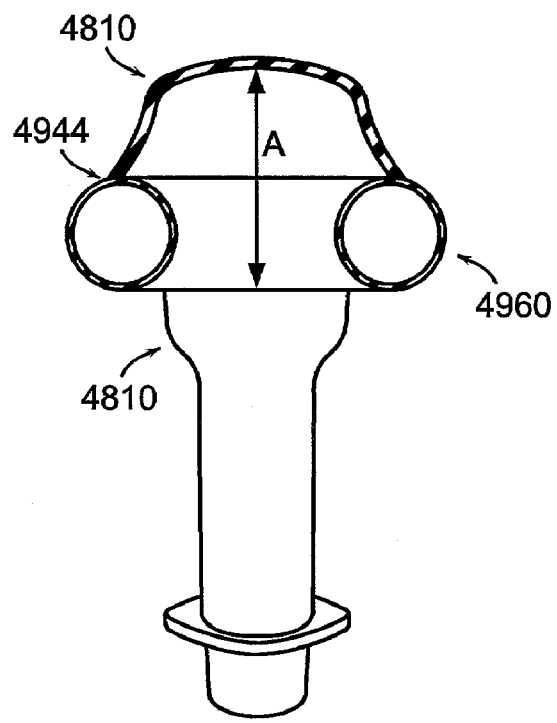
FIG. 49F shows a sectional view of the device shown in FIG. 49B taken in the direction of arrow 49F—49F.

FIGS. 49A and 49B show perspective anterior and side views, respectively, of yet another embodiment of a laryngeal mask airway device 4900 constructed according to the invention. Device 4900 includes an airway tube 4810, of the type shown in FIGS. 48A and 48B, and an inflatable cuff 4960. In this embodiment, the mask portion of the device is the cuff 4960. FIGS. 49C and 49D show side and anterior views, respectively, of cuff 4960. FIG. 49E shows a sectional view of cuff 4960 taken in the direction of arrow 49E—49E as shown in FIG. 49C. Finally, FIG. 49F shows a sectional view of device 4900 taken in the direction of arrow 49F—49F as shown in FIG. 49B.

As shown, cuff 4960 is characterized by an elliptical torus shape. The shape is that of a torus, or is toroidal, because the cross section of cuff 4960 at any point is generally circular (e.g., as shown in FIG. 49E). The shape is an elliptical torus because rather than being a perfect ring, or donut shape, the cuff is elongated so that the length of the cuff as measured in the proximal-to-distal direction (or the distance between the cuff's proximal end 4932 and its distal end 4934) is greater than the width of the cuff as measured in the left-to-right direction (e.g., as shown generally by the distance W1 as illustrated in FIG. 5E).

Cuff 4960 includes an inflation plug 4901 generally located at the cuff's proximal end 4932. In use, plug 4901 is coupled to an inflation line (not shown) for controlling inflation and deflation of cuff 4960.

Unlike the majority of cuffs and mask portions discussed above, cuff 4960 is normally not formed by rotational molding. Rather, cuff 4960 is normally formed by injection molding or blow molding a plastic such as PVC into the desired elliptical torus shape. The thickness T of the cuff wall, as shown in FIG. 49E, is preferably about 0.5–0.65 millimeters, and the material used to form the cuff is preferably characterized by a durometer of about 55 Shore A. It will be appreciated that many conventional laryngeal mask airway devices include an inflatable cuff similar to cuff 4960. It will also be appreciated that the preferred profile of the laryngeal side of cuff 4960 may be different than what is illustrated in FIGS. 49A and 49D. In particular, as discussed above, the preferred profile for the laryngeal side of cuff 4960 may be that of the "Classic" as shown generally in FIG. 14.

Generally, conventional laryngeal mask airway devices including a cuff similar to that of cuff 4960 also include a thin dome-shaped plastic skin arising from the inner perimeter of the torus. The skin is normally perforated to form three apertures separated by two aperture bars, and the aperture bars support the epiglottis and prevent the epiglottis from blocking the airway provided by the device. Such laryngeal mask airway devices generally also include a relatively stiff backplate which is attached to this dome-shape skin. Device 4900 includes neither the skin nor the separate backplate component generally used in those conventional laryngeal mask airway devices. In device 4900, the airway tube itself in effect forms a backplate by its prolongation adjacent to the pharyngeal surface of the cuff.

Figure 49G:
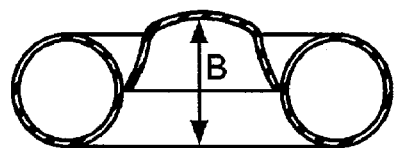
FIG. 49G shows a sectional view of a laryngeal mask airway device in which the backplate is attached at a equatorial location of the cuff.

As shown best in FIG. 49F, in device 4900 the laryngeal side of the backplate portion of the airway tube 4810 is attached to cuff 4960 at the pharyngeal side 4944 of the cuff. Attaching the airway tube 4810 to the pharyngeal side 4944 of the cuff rather than at an equatorial location (i.e., at the midpoint of the cuff as measured in the pharyngeal-to-laryngeal direction) effectively increases the depth of the bowl shaped aperture 4942 (as shown in FIG. 49A) defined by the cuff. The arrow A in FIG. 49F illustrates the depth of the bowl shaped aperture 4942 in device 4900. The arrow B in FIG. 49G illustrates how much shallower the bowl shaped aperture is in a conventional laryngeal mask airway device in which the backplate is attached to the cuff an equatorial location. Increasing the depth of bowl shaped aperture 4942 allows the anatomy of the larynx to extend further into the bowl 4942 when the device 4900 is in the fully inserted configuration and thereby increases the seal provided by the device.

One potential disadvantage of attaching the airway tube 4810 to the pharyngeal side 4944 of the cuff rather than at an equatorial location, is that structural support provided to the cuff is reduced and the cuff can become more susceptible to collapse in the presence of forces generated by the patient's anatomy in the direction of the arrows F as shown in FIG. 35B. However, this potential problem is circumvented by the use of tabs 4870 in the airway tube 4810. As with device 4800 (e.g., as shown in FIGS. 48C and 48D), in device 4900 the tabs 4870 extend into the bowl shaped aperture defined by the cuff 4960 and tend to prevent the cuff 4960 from collapsing in the presence of forces in the direction of the arrows F as shown in FIG. 35B. Also as with device 4800, airway tube 4810 may also include a reinforcing strut, or bar, 4870A which extends between and connects to both tabs 4870 for further increasing the resistance to collapse. It will be appreciated that device 4900 is relatively simple and inexpensive to construct and is another embodiment of a disposable laryngeal mask airway device.

Since certain changes may be made in the above apparatus without departing from the scope of the invention herein involved, it is intended that all matter contained in the above description or shown in the accompanying drawing shall be interpreted in an illustrative and not a limiting sense.

What is claimed is:

1. A laryngeal mask airway device, comprising a mask portion and an airway tube, the airway tube extending along a central axis from a proximal end to a distal end, the mask portion being attached to the airway tube near the distal end of the airway tube, the mask portion being insertable through the mouth of a patient to an inserted location within the patient, the mask portion forming a seal around the patient's glottic opening when the mask portion is in the inserted location, the proximal end of the tube being outside the patient's mouth when the mask portion is at the inserted location, the airway tube defining an internal passage, the internal passage extending from the proximal end of the airway tube to the mask portion, the internal passage defining one or more notches, at least one of the notches being disposed near the proximal end of the tube, each of the notches extending along at least a portion of the airway tube in a direction generally parallel to the central axis, the notches being configured to allow a cylindrical tube inserted into the proximal end of the airway tube to extend into the notches as the cylindrical tube is advanced through the airway tube.

2. A device according to claim 1, the airway tube including a curved central portion disposed between the proximal and distal ends, the central portion extending through part of the patient's natural upper airway when the mask portion is in the inserted location, the central portion defining an inner side and an outer side, one of the notches being defined in the outer side of the central portion.

3. A device according to claim 2, the airway tube including a proximal portion near the proximal end of the airway tube, two of the notches being defined in the proximal portion.

4. A device according to claim 1, the airway tube including a proximal portion near the proximal end of the airway tube, two of the notches being defined in the proximal portion.

5. A device according to claim 4, the airway tube including a curved central portion disposed between the proximal and distal ends, the central portion extending through part of the patient's natural upper airway when the mask portion is in the inserted location, the central portion defining an inner side and an outer side, one of the notches being defined in the outer side of the central portion.

6. A device according to claim 1, the device including a bar disposed in the airway tube near the distal end of the airway tube, at least one of the notches being defined by the bar.

7. A laryngeal mask airway device, comprising a mask portion and an airway tube, the airway tube extending along a central axis from a proximal end to a distal end, the mask portion being attached to the airway tube near the distal end of the airway tube, the mask portion being insertable through the mouth of a patient to an inserted location within the patient, the mask portion forming a seal around the patient's glottic opening when the mask portion is in the inserted location, the proximal end of the airway tube being near the mouth of the patient when the mask portion is at the inserted location, the airway tube defining an internal passage, the internal passage extending from the proximal end of the airway tube to the mask portion, the internal passage defining one or more notches, at least one of the notches being disposed near the proximal end of the tube, each of the notches extending along at least a portion of the airway tube in a direction generally parallel to the central axis, the notches being configured to allow a cylindrical tube inserted into the proximal end of the airway tube to extend into the notches as the cylindrical tube is advanced through the airway tube.

* * * * *